(12) United States Patent
Sun

(10) Patent No.: US 11,118,205 B2
(45) Date of Patent: Sep. 14, 2021

(54) METHOD FOR PRODUCING N-ACETYL-D-GLUCOSAMINE AND/OR D-GLUCOSAMINE SALT BY MICROBIAL FERMENTATION

(71) Applicant: Lan Sun, Jiangsu (CN)

(72) Inventor: Lan Sun, Jiangsu (CN)

( * ) Notice: Subject to any disclaimer, the term of this patent is extended or adjusted under 35 U.S.C. 154(b) by 0 days.

(21) Appl. No.: 16/091,714

(22) PCT Filed: Apr. 14, 2017

(86) PCT No.: PCT/CN2017/080652
§ 371 (c)(1),
(2) Date: Oct. 5, 2018

(87) PCT Pub. No.: WO2017/174039
PCT Pub. Date: Oct. 12, 2017

(65) Prior Publication Data
US 2019/0390238 A1    Dec. 26, 2019

(30) Foreign Application Priority Data

Apr. 5, 2016 (CN) .......................... 201610208203.9
Apr. 5, 2017 (CN) .......................... 201710217322.5

(51) Int. Cl.
| | | |
|---|---|---|
| *C12P 19/26* | (2006.01) | |
| *C12N 9/10* | (2006.01) | |
| *C12N 9/12* | (2006.01) | |
| *C12N 9/80* | (2006.01) | |
| *C12N 9/90* | (2006.01) | |
| *C12N 15/70* | (2006.01) | |
| *C12N 9/78* | (2006.01) | |
| *C12N 9/88* | (2006.01) | |
| *C12P 19/02* | (2006.01) | |
| *C12N 1/20* | (2006.01) | |
| *C12R 1/19* | (2006.01) | |

(52) U.S. Cl.
CPC ............ *C12P 19/26* (2013.01); *C12N 9/1029* (2013.01); *C12N 9/1205* (2013.01); *C12N 9/78* (2013.01); *C12N 9/80* (2013.01); *C12N 9/88* (2013.01); *C12N 9/90* (2013.01); *C12N 15/70* (2013.01); *C12P 19/02* (2013.01); *C12Y 203/01157* (2013.01); *C12Y 207/0106* (2013.01); *C12Y 305/01025* (2013.01); *C12Y 305/99006* (2013.01); *C12Y 401/03003* (2013.01); *C12Y 501/03009* (2013.01); *C12Y 501/03014* (2013.01); *C12Y 504/02001* (2013.01); *C12Y 504/0201* (2013.01); *C12N 1/205* (2021.05); *C12R 2001/19* (2021.05)

(58) Field of Classification Search
None
See application file for complete search history.

(56) References Cited

U.S. PATENT DOCUMENTS

2004/0091976 A1 * 5/2004 Deng .................... C12N 15/52
435/84

FOREIGN PATENT DOCUMENTS

| CN | 103060358 A | 4/2013 | |
|---|---|---|---|
| CN | 103602627 A | 2/2014 | |
| CN | 104988108 A | 10/2015 | |
| CN | 105039464 A | 11/2015 | |
| EP | 2970872 A1 | 1/2016 | |
| WO | 9830713 A1 | 7/1998 | |
| WO | WO-2014153253 A1 * | 9/2014 | ........... C12N 9/1051 |

OTHER PUBLICATIONS

Genbank AJN12189. GenBank2015. p. 1.*
International Search Report dated Aug. 23, 2017 from related PCT Application No. PCT/CN2017/080652.

* cited by examiner

*Primary Examiner* — Paul J Holland
(74) *Attorney, Agent, or Firm* — Grogan, Tuccillo & Vanderleeden, LLP

(57) ABSTRACT

The present invention discloses a process for producing N-acetyl-D-glucosamine and D-glucosamine salts by microbial fermentation. The invention includes a method to produce N-acetyl-D-glucosamine and/or D-glucosamine salts with higher efficiency and higher yield by increasing the effect of N-acetyl-D-aminomannose-6-phosphate epimerase in microorganisms.

8 Claims, 1 Drawing Sheet
Specification includes a Sequence Listing.

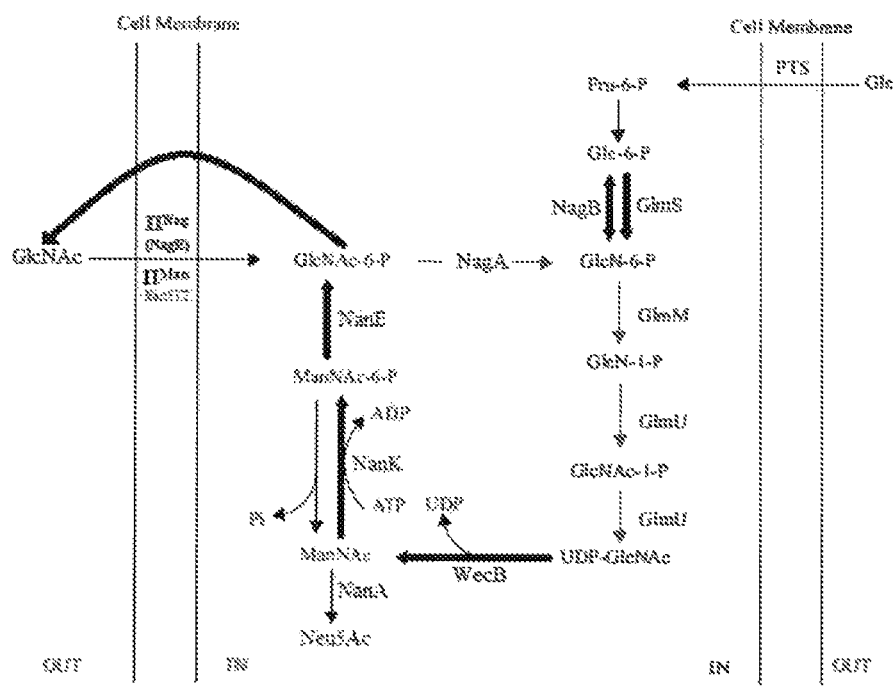

METHOD FOR PRODUCING N-ACETYL-D-GLUCOSAMINE AND/OR D-GLUCOSAMINE SALT BY MICROBIAL FERMENTATION

CROSS REFERENCE TO RELATED APPLICATIONS

This application is the National Stage of International Application No. PCT/CN2017/080652 filed Apr. 14, 2017 and claims benefit of Chinese Application No. 201610208203.9 filed on Apr. 5, 2016 and Chinese Application No. 201710217322.5 filed on Apr. 5, 2017.

SEQUENCE LISTING

The instant application contains a sequence listing which has been submitted in ASHII format via EFS-Web and hereby incorporated by reference in its entirety. Said ASCII copy, created on May 1, 2015 and is 18,532 bytes in size.

TECHNICAL FIELD

The invention belongs to the field of microbial fermentation. Specifically, the present invention relates to a method for the production of N-acetyl-D-glucosamine by microbial fermentation and the further preparation of D-glucosamine salts.

BACKGROUND

N-Acetyl-D-glucosamine (NAG or GlcNAc), also known as N-acetyl-glucosamine, N-acetylglucosamine, is the basic building block of many important polysaccharides in biological cells, having important physiological functions in living organisms. N-acetyl-D-glucosamine can be used clinically in: enhancing the function of the human immune system; inhibiting the growth of malignant tumors or fibroblast; effectively treating various inflammations; acting as a low-calorie sweetener for diabetic patients and food additives for infants and young children; etc. Hydrolyzed N-acetyl-D-glucosamine can be used to produce D-glucosamine hydrochloride, which can be used as anti-cancer, cancer prevention, blood lipid lowering, and blood pressure lowering food supplements. It is the third generation of health functional food additive in the current chitosan health food series. Additionally, N-acetyl-D-glucosamine is the main raw material for the synthesis of anti-cancer drug chlorozotocin in the pharmaceutical industry; as a biochemical reagent, it can also be used as an immunological adjuvant against bacterial infections and as an activator of human anti-influenza virus.

Around the world, there are a large number of patients suffering from various degrees of arthritis pain. In the United States alone, 33 million people suffer from osteoarthritis and joint pain, and more than 150 million people in China suffer from such. Because of the special effect of D-glucosamine products in the treatment and health care of arthritis and joint pain, it has been widely used and become a very important raw ingredient in medicines in foreign markets.

N-acetyl-D-glucosamine is thought to have a similar effect as D-glucosamine, and it is known that taking N-acetyl-D-glucosamine can induce the production of new cartilage and prevent the onset of osteoarthritis, or in some cases, it can be used to treat osteoarthritis. Since D-glucosamine has a bitter taste, while N-acetyl-D-glucosamine has a sweetness of 50% sucrose and is easily ingested, using N-acetyl-D-glucosamine as a substitute for D-glucosamine has attracted attention.

At present, the main source of glucosamine in China and abroad is based on biological extraction. The biological extraction is mainly obtained by extracting chitin or chitosan from shrimp and crab shells, and then prepared by hydrolyzing with concentrated hydrochloric acid, or by acid-base extracting with citric acid residue. The annual production is about 20,000 tons. However, when extracting from shrimp and crab shells, a large amount of waste residue and more than 100 tons of waste water will be produced for each ton of product obtained; when extracting with citric acid residue, 30-50 tons of waste acid residue will be produced for every ton of product obtained. It is a highly polluting process and has been banned in many places. Moreover, glucosamine extracted from the shells of aquatic products is not suitable for many patients who are allergic to aquatic products. People who are allergic to aquatic products may have serious allergic reactions and even life-threatening problems after using such glucosamine. In addition, the biological extraction and purification process is complex, and the product has a fishy smell and is unstable. Furthermore, due to environmental pollution, glucosamine extracted from shrimp and crab shells is inevitably contaminated by heavy metals.

Therefore, using biological extraction methods to produce glucosamine cannot meet people's needs in terms of quantity and quality, and thus, new alternative methods much be sought. If chemical synthesis is used to prepare, there exist three disadvantages: high production cost; serious environmental pollution; and safety hazards. This method is currently not used in China and abroad. In comparison, the production of glucosamine by microbial fermentation is a good way. The microbial fermentation method uses glucose and inorganic salts as raw materials, selects excellent strains for liquid fermentation, and directly produces glucosamine by separation, concentration and purification. There are no harmful gases produced during the production process. The glucosamine produced by the fermentation method has no fishy smell and the production is not restricted by resources. Moreover, the use of metabolic engineering to improve strains can produce high yields and has the potential for large industrial production. Therefore, the production of glucosamine by microbial fermentation has undergone a major revolution in the technical process. Instead of the traditional biological extraction, it not only has an advantage in cost reduction, but also has a certain environmental contribution in reducing the pollution of the three wastes.

Conventional methods for the production of N-acetyl-D-glucosamine by microbial fermentation include: a method involving the production of N-acetyl-D-glucosamine from chitin produced from shrimp shell material by an enzyme produced by a microorganism (for example, U.S. Pat. No. 5,998,173, "Process for producing N-acetyl-D-glucosamine"); a method of enzymatic hydrolysis by microorganisms (*Trichoderma*) or partial hydrolysis of acid to purify chitin from fungal residue (such as the residue of *Aspergillus nicoticus* used in citric acid fermentation) to produce N-A method of acetyl-D-glucosamine (for example, US20030073666A1, "N-acetyl-D-glucosamine and process for producing N-acetyl-D-glucosamine"); a method for producing N-acetyl-D-glucosamine by direct use of glucose as a carbon source by *Trichoderma* and not using carbon source from fungal residue or chitin and chitin oligosaccharide produced by shrimp shells (for example, US20110059489A1, "Method for fermentative production of N-acetyl-D-glucosamine by microorganism"); a method for the production of N-acetyl-D-glucosamine by culturing Chlorovirus infected *Chlorella* cells or recombinant *Escherichia coli* with a gene derived from Chlorovirus (for example, JP2004283144A, "Method for producing glucosamine and N-acetylglucosamine"); a method of fermentative production of D-glucosamine or N-acetyl-D-glucosamine using genetically modified microorganisms, particularly genetically modified *Escherichia coli* (for example, U.S. Pat. No. 6,372,457, "Process and materials for production of glucosamine"; WO2004/003175, "Process and materials for production of glucosamine and N-acetylglucosamine").

The use of microorganisms or enzymes produced by microorganisms to degrade chitin from crustaceans such as crabs and shrimp to produce N-acetyl-D-glucosamine is relatively traditional, and has problems such as low yield, high cost, and insufficient source of animals. The method for producing N-acetyl-D-glucosamine by culturing Chlorovirus infected *Chlorella* cells involves a step of crushing cells to obtain N-acetyl-D-glucosamine, which has problems such as complicated operation. The method of fermenting N-acetyl-glucosamine directly using glucose as a carbon source by *Trichoderma* has the advantage of not requiring the use of a carbon source such as chitin or chitin oligosaccharide produced from crustaceans or fungal residue, but Fungi such as *Trichoderma* has low fermentation temperature (27° C.), long time (10 days), and low yield (15 mg/ml), which has the disadvantages of long production cycle, high cost, easy contamination of bacteria, and severely limits the method in industrial application.

Obviously, the production of N-acetyl-D-glucosamine by genetically modified microorganisms is an important application method for large-scale industrial production in view of the growing market demand for glucosamine. New genetically modified microorganisms can be obtained in many ways, such as genetic recombination, gene transfer, gene mutation, gene deletion, gene overexpression, and metabolic pathway changes, etc.

Methods and materials for the production of D-glucosamine by microbial fermentation are disclosed in U.S. Pat. No. 6,372,457. The invention includes genetically modified microorganisms for use in the method of producing glucosamine of the invention, as well as recombinant nucleic acid molecules and proteins produced by the recombinant nucleic acid molecules. The genetically modified microorganism of the invention is mainly directed to a genetic modification capable of increasing the activity of glucosamine-6-phosphate synthase, including various gene mutations or amino acid deletions and substitutions. However, this patent does not direct to an increase or decrease in glucosamine-6-phosphate synthase activity by changes such as endogenous glucosamine-6-phosphate synthase gene promoter replacement or deletion. In addition, the patent mainly directs to the production of D-glucosamine by genetic modification of glucosamine-6-phosphate synthase, and does not direct to N-acetyl-D-glucosamine production. Moreover, since D-glucosamine is very unstable in the fermentation broth, the degradation products may be toxic to microorganisms. The production of D-glucosamine by genetic modification has a low yield and has practical limitations.

Biosynthesis methods for the production of D-glucosamine and N-acetyl-D-glucosamine are disclosed in WO2004/003175. The method directs to modifying the microorganism by fermenting genes to produce glucosamine and/or N-acetyl-D-glucosamine. The invention also discloses genetically modified microorganisms for the production of glucosamine and N-acetyl-D-glucosamine. Further, the invention also describes a method of recovering N-acetyl-D-glucosamine produced by a fermentation process, including a method of producing high-purity N-acetyl-D-glucosamine. The invention also discloses a process for producing D-glucosamine from N-acetyl-D-glucosamine. The genetically modified microorganism of the invention is primarily directed to a genetic modification that increases the activity of glucosamine-6-phosphate acetyltransferase. Yeast glucosamine-6-phosphate acetyltransferase gene (GNA1) expressed in *E. coli* can acetylate glucosamine-6-phosphate to acetylglucosamine-6-phosphate, which has been reported and confirmed in previous literature (Mio T1, Yamada-Okabe T, Arisawa M, Yamada-Okabe H: *Saccharomyces cerevisiae* GNA1, an essential gene encoding a novel acetyltransferase involved in UDP-N-acetylglucosamine synthesis, *J Biol Chem.*, 1999 Jan. 1; 274(1): 424-9.).

SUMMARY OF THE INVENTION

The present invention is directed to the metabolic pathway of N-acetyl-D-glucosamine, using a novel genetic modification method to transform microorganisms, and using the microorganism to produce N-acetyl-D-glucosamine (GlcNAc) and/or D-glucosamine salts with higher efficiency and higher yield.

Specifically, the present invention increases the action of N-acetyl-D-aminomannose-6-phosphate epimerase(NanE) in the microorganisms, enhances the conversion of N-acetyl-D-mannosamine-6-phosphate (ManNAc-6-P) to N-acetyl-D-glucosamine-6-phosphate (GlcNAc-6-P), which is excreted extracellularly to become N-acetyl-D-glucosamine (GlcNAc), thus allowing the microorganism to produce N-acetyl-D-glucosamine (GlcNAc) and/or D-glucosamine salts with higher efficiency and higher yield.

The present invention further relates to one or more of the following:

1. By increasing the effect of D-Glucosamine-6-phosphate deaminase (NagB) in the microorganisms, and simultaneously reducing the effect of Glucosamine-6-phosphate synthase (GlmS, also known as L-glutamine-6-phosphate fructose aminotransferase), to enhance the amination of glucose-6-phosphate (Glc-6-P) to D-glucosamine-6-phosphate (GlcN-6-P) in the microorganisms. The reaction catalyzed by D-glucosamine-6-phosphate deaminase (NagB) is reversible, and the reaction catalyzed by glucosamine-6-phosphate synthase (GlmS) is irreversible, but it has serious product inhibition problems. When the NagB-catalyzed reaction proceeds to the direction in which Glc-6-P produces GlcN-6-P, it has the same function as GlmS, and can replace GlmS, and has no product inhibition problem. By increasing the effect of NagB, accelerating the NagB catalytic reaction from Glc-6-P to GlcN-6-P, and preferably simultaneously reducing the effect of GlmS, it can attenuate the product inhibition problem of GlmS, and achieve the purpose of increasing GlcN-6-P production. This allows the microorganism to produce N-acetyl-D-glucosamine (GlcNAc) and/or D-glucosamine salts with higher efficiency and higher yield.

2. By increasing the effect of glucosamine-6-phosphate synthase (GlmS, also known as L-glutamine-6-phosphate fructose aminotransferase), and at the same time reducing the effect of D-Glucosamine-6-phosphate deaminase (NagB), to strengthen the amination of glucose-6-phosphate (Glc-6-P) to D-glucosamine-6-phosphate (GlcN-6-P) in the microorganisms. The reaction catalyzed by D-glucosamine-6-phosphate deaminase (NagB) is reversible. When the NagB-catalyzed reaction proceeds to the direction in which GlcN-6-P produces Glc-6-P, it functions opposite to GlmS, and will offset the effect of GlmS. Decreasing the effect of NagB, preventing the NagB catalytic reaction from proceeding to the production of GlcN-6-P to Glc-6-P, and simultaneously overexpressing GlmS, accelerating GlmS-catalyzed Glc-6-P amination to GlcN-6-P, to achieve the purpose increasing GlcN-6-P to allow the microorganism to produce N-acetyl-D-glucosamine (GlcNAc) and/or D-glucosamine salts with higher efficiency and higher yield.

3. By enhancing the effect of UDP-N-acetyl-D-glucosamine-2-epimerase, WecB) to increase the conversation of UDP-N-acetyl-D-glucosamine (UDP-GlcNAc) to N-acetyl-D-mannosamine (ManNAc) in the microorganism, thereby making the microorganism to produce N-acetyl-D-glucosamine (GlcNAc) and/or D-glucosamine salts with higher efficiency and higher yield.

4. By reducing the effect of an enzyme or protein in the microorganism associated with the re-intake of the target product into the cell or the degradation of the beneficial intermediate, and increasing the sugar conversion rate and the N-acetyl-D-glucosamine production in the microorganism, thereby allowing the microorganism to produce N-acetyl-D-glucosamine (GlcNAc) and/or D-glucosamine salts with higher efficiency and higher yields. This includes but not limited to one or more of the following:

(1) Decreasing the effect of mannose transporter EIIM, P/III$^{man}$ (Mannose transporter EIIM, P/III$^{Man}$, ManXYZ) in microorganisms to prevent hexose transport such as N-acetyl-D-glucosamine (GlcNAc) from being transported back into the cell for degradation.

(2) Reducing the effect of N-acetylneuraminic acid lyase (NanA) in microorganisms to prevent degradation of N-acetyl-D-mannosamine (ManNAc) in microorganisms.

(3) Reducing the effect of N-acetyl-glucoseamine-6-phosphate deacetylase (NagA) in microorganisms to prevent the conversion of N-acetyl-D-glucosamine-6-phosphate (GlcNAc-6-P) in microorganisms to D-glucosamine-6-phosphate (GlcN-6-P).

(4) Reducing the effect of N-acetyl-D-glucosamine specific enzyme II$^{Nag}$ (NagE) in microorganisms to prevent N-acetyl-D-glucosamine (GlcNAc) from being transported into the cells for degradation.

(5) Enhancing the effect of phosphoglucosamine mutase (GlmM) in microorganisms to increase the conversion of D-glucosamine-6-phosphate (GlcN-6-P) to D-glucosamine-1-phosphate (GlcN-1-P).

(6) Increasing the effect of bifunctional enzyme N-acetyl-D-glucosamine-1-phosphate uridine transferase (bifunctional N-acetyl glucosamine-1-phosphate uridyltransferase/glucosamine-1-phosphate acetyl transferase, GlmU) to increase the conversion of D-glucosamine-1-phosphate (GlcN-1-P) in microorganisms to N-acetyl-D-glucosamine-1-phosphate (GlcNAc-1-P), and the further conversion to UDP-N-acetyl-D-glucosamine (UDP-GlcNAc).

DETAILED DESCRIPTION OF THE INVENTION

According to one embodiment of this invention, the invention relates to a method for the production of N-acetyl-D-glucosamine (GlcNAc) and/or D-glucosamine salts by microbial fermentation. The method comprising:

A) Cultivating a microorganism in a fermentation medium, said microorganism comprising at least one genetic modification capable of increasing the effect of N-acetyl-D-aminomannose-6-phosphate epimerase (NanE) in the microorganism; and B) Collecting of N-acetyl-D-glucosamine (GlcNAc) produced from the cultivating step A).

Preferably, the method further comprises:

C) deacetylating from N-acetyl-D-glucosamine (GlcNAc) to obtain a D-glucosamine salt.

In the present invention, the genetic modification for increasing the effect of N-acetyl-D-aminomannose-6-phosphate epimerase (NanE) in a microorganism is selected from the group consisting of a) increasing the enzymatic activity of N-acetyl-D-aminomannose-6-phosphate epimerase (NanE) in a microorganism; and/or b) overexpressing the N-acetyl-D-aminomannose-6-phosphate epimerase (NanE) in the microorganism.

It will be understood by those skilled in the art that it is possible to enhance the effect of N-acetyl-D-aminomannose-6-phosphate epimerase (NanE) in microorganisms through screening gene mutations that encode N-acetyl-D-aminomannose-6-phosphate epimerase (NanE) with an increased enzyme activity. Screening of NanE gene mutations can be accomplished by error-prone PCR techniques to obtain high frequency mutant genes. It is also possible to enhance the effect of N-acetyl-D-aminomannose-6-phosphate epimerase (NanE) in microorganisms by increasing the number of copies of the gene or replacing the native promoter with a promoter having a higher expression level to overexpress N-acetyl-D-aminomannose-6-phosphate epimerase (NanE). In a specific embodiment, the microorganism is transformed with at least one recombinant nucleic acid molecule comprising at least one genetic modification that enhances the effect of N-acetyl-D-aminomannose-6-phosphate epimerase (NanE) in the microorganism.

In a preferred embodiment, the microorganism is transformed with at least one recombinant nucleic acid molecule comprising a nucleic acid sequence encoding N-acetyl-D-aminomannose-6-phosphate epimerase (NanE).

In one aspect, the nucleic acid sequence encoding N-acetyl-D-aminomannose-6-phosphate epimerase (NanE) comprises at least one genetic modification that increases the enzymatic activity of N-acetyl-D-aminomannose-6-phosphate epimerase (NanE). Preferably, the genetic modification comprises one or two of the substitutions at positions corresponding to the amino acid sequence of SEQ ID NO: 17: the 133th cysteine is replaced by arginine and the 187th tyrosine is replaced by histidine. Further preferably, the nucleic acid sequence encoding the N-acetyl-D-aminomannose-6-phosphate epimerase (NanE) is SEQ ID NO: 26; the amino acid sequence of N-acetyl-D-aminomannose-6-phosphate epimerase (NanE) is SEQ ID NO:27.

In another aspect, the amino acid sequence of the N-acetyl-D-aminomannose-6-phosphate epimerase (NanE) has at least about 30% identity of the amino acid sequence of SEQ ID NO:17, preferably at least about 50% identity, further preferably at least about 70% identify, further preferably at least about 80% identity, still more preferably at least about 90% identity, and most preferably at least about 95% identity of amino acid sequence of SEQ ID NO: 17, wherein said N-acetyl-D-aminomannose-6-phosphate epimerase (NanE) has enzymatic activity.

In another aspect, the N-acetyl-D-aminomannose-6-phosphate epimerase (NanE) has the amino acid sequence of SEQ ID NO: 17.

In another aspect, the gene copy number of the gene encoding the N-acetyl-D-aminomannose-6-phosphate epimerase (NanE) is increased in the recombinant nucleic acid molecule.

In another aspect, the recombinant nucleic acid molecule comprises an endogenous native promoter, a promoter having a higher expression level than the endogenous native promoter, an enhancer, a fusion sequence, and the like. Preferably, the recombinant nucleic acid molecule comprises a promoter having a higher expression level than the endogenous natural promoter, such as an HCE promoter, a gap promoter, a trc promoter, a T7 promoter, etc.; more preferably, the recombinant nucleic acid molecule comprises a trc promoter. The trc promoter is a split promoter of the trp promoter and the lac promoter, which has higher transcription efficiency than trp and has strong promoter properties regulated by lacI repressor.

In the present invention, the recombinant nucleic acid molecule transformed into a microorganism is selected from the group consisting of a free form (i.e., a recombinant nucleic acid molecule is loaded into a plasmid) and an integrated type (i.e., a recombinant nucleic acid molecule is integrated into the genome of the microorganism). Preferably, the recombinant nucleic acid molecule is integrated into the genome of the microorganism.

In another preferred embodiment, the microorganism comprises at least one genetic modification of an endogenous native promoter of a gene encoding N-acetyl-D-aminomannose-6-phosphate epimerase (NanE). Preferably, the endogenous native promoter of the gene encoding N-acetyl-D-aminomannose-6-phosphate epimerase (NanE) is replaced by a promoter with a higher expression level, such as the HCE promoter, the gap promoter, The trc promoter, the T7 promoter and the like; more preferably, the endogenous natural promoter of the gene encoding N-acetyl-D-aminomannose-6-phosphate epimerase (NanE) is replaced by the trc promoter.

According to a preferred embodiment of the invention, the microorganism further comprises one or more of the following genetic modifications:

(1) Comprising at least one genetic modification capable of enhancing the effect of D-glucosamine-6-phosphate deaminase (NagB) in a microorganism, preferably comprising at least one genetic modification capable of reducing the effect of glucosamine-6-phosphate synthase (GlmS);

(2) Comprising at least one genetic modification capable of increasing the effect of glucosamine-6-phosphate synthase (GlmS) in the microorganism, and at the same time comprising at least one genetic modification capable of reducing the effect of D-glucosamine-6-phosphate deaminase (NagB); and (3) Comprising at least one genetic modification capable of enhancing the effect of UDP-N-acetyl-D-glucosamine-2-epimerase (WecB) in microorganisms.

In the above aspect (1), the genetic modification for enhancing the effect of D-glucosamine-6-phosphate deaminase (NagB) in the microorganism is selected from the group consisting of a) increasing the enzymatic activity of D-glucosamine-6-phosphate deaminase (NagB) in the microorganism; and/or b) overexpressing the D-glucosamine-6-phosphate deaminase (NagB) in the microorganism.

It will be understood by those skilled in the art that enhancing the effect of D-glucosamine-6-phosphate deaminase (NagB) in microorganisms can be achieved through screening gene mutations that encode D-glucosamine-6-phosphate deaminase (NagB) with an increased enzyme activity. Screening for NagB gene mutations can be accomplished by error-prone PCR techniques to obtain high frequency mutant genes. Enhancing the effect of D-glucosamine-6-phosphate deaminase (NagB) in microorganisms can also be achieved by overexpressing D-glucosamine-6-phosphate deaminase (NagB) through methods such as increasing the gene copy number and replacing a promoter with a higher expression level than the native promoter. In a specific embodiment, the microorganism is transformed with at least one recombinant nucleic acid molecule comprising at least one genetic modification that enhances the effect of D-glucosamine-6-phosphate deaminase (NagB) in the microorganism.

In a preferred embodiment, the microorganism is transformed with at least one recombinant nucleic acid molecule comprising at least one nucleic acid sequence encoding D-glucosamine-6-phosphate deaminase (NagB).

In one aspect, the nucleic acid sequence encoding D-glucosamine-6-phosphate deaminase (NagB) contains at least one genetic modification that increases the enzymatic activity of D-glucosamine-6-phosphate deaminase (NagB).

In another aspect, the gene copy number of the gene encoding D-glucosamine-6-phosphate deaminase (NagB) is increased in the recombinant nucleic acid molecule.

In another aspect, the recombinant nucleic acid molecule comprises an endogenous native promoter, a promoter having a higher expression level than the endogenous native promoter, an enhancer, a fusion sequence, and the like. Preferably, the recombinant nucleic acid molecule comprises a promoter having a higher expression level than the endogenous natural promoter, such as an HCE promoter, a gap promoter, a trc promoter, a T7 promoter, etc.; more preferably, the recombinant nucleic acid molecule comprises a trc promoter.

In the present invention, the recombinant nucleic acid molecule transformed into a microorganism is selected from the group consisting of a free form (i.e., a recombinant nucleic acid molecule is loaded into a plasmid) and an integrated type (i.e., a recombinant nucleic acid molecule is integrated into the genome of the microorganism). Preferably, the recombinant nucleic acid molecule is integrated into the genome of the microorganism.

In another preferred embodiment, the microorganism comprises at least one genetic modification of an endogenous native promoter of a gene encoding D-glucosamine-6-phosphate deaminase (NagB). Preferably, the endogenous native promoter of the gene encoding D-glucosamine-6-phosphate deaminase (NagB) is replaced by a promoter with a higher expression level, such as the HCE promoter, the gap promoter, the trc promoter, The T7 promoter or the like; more preferably, the endogenous natural promoter of the gene encoding D-glucosamine-6-phosphate deaminase (NagB) is replaced by the trc promoter.

In the present invention, the genetic modification for reducing the effect of glucosamine-6-phosphate synthase (GlmS) in the microorganism is selected from a) a decrease in the enzymatic activity of glucosamine-6-phosphate synthase (GlmS) in the microorganism; and/or b) a reduced expression of glucosamine-6-phosphate synthase (GlmS) in microorganisms, including but not limited to: partial or complete deletion or partial or complete inactivation of the endogenous genes encoding glucosamine-6-phosphate synthase (GlmS) in microorganisms, and/or partial or complete deletion, or partial or complete inactivation of an endogenous natural promoter encoding a glucosamine-6-phosphate synthase (GlmS) gene in a microorganism. Preferably, the genetic modification reducing the effect of glucosamine-6-phosphate synthase (GlmS) in the microorganism is the complete deletion of the endogenous natural promoter encoding the glucosamine-6-phosphate synthase (GlmS) gene in the microorganism.

In a specific embodiment, the microorganism is transformed with at least one recombinant nucleic acid molecule comprising at least one genetic modification that reduces the effect of glucosamine-6-phosphate synthase (GlmS) in the microorganism.

In the above aspect (2), the genetic modification for increasing the effect of glucosamine-6-phosphate synthase (GlmS) in the microorganism is selected from a) an increase in the enzymatic activity of glucosamine-6-phosphate synthase (GlmS) in the microorganism; and/or b) overexpression of glucosamine-6-phosphate synthase (GlmS) in the microorganism.

It will be understood by those skilled in the art that enhancing the effect of glucosamine-6-phosphate synthase (GlmS) in microorganisms can be achieved by screening gene mutations that encode glucosamine-6-phosphate synthase (GlmS) with an increased enzyme activity. Screening for NagB gene mutations can be accomplished by error-prone PCR techniques to obtain high frequency mutant genes. Enhancing the effect of glucosamine-6-phosphate synthase (GlmS) in microorganisms can also be achieved by overexpressing glucosamine-6-phosophate synthases (GlmS) through increasing its gene copy number and replacing a promoter with a higher expression level than the native promoter. In a specific embodiment, the microorganism is transformed with at least one recombinant nucleic acid molecule comprising at least one genetic modification that enhances the action of glucosamine-6-phosphate synthase (GlmS) in the microorganism.

In a preferred embodiment, the microorganism is transformed with at least one recombinant nucleic acid molecule comprising a nucleic acid sequence encoding glucosamine-6-phosphate synthase (GlmS).

In one aspect, the nucleic acid sequence encoding glucosamine-6-phosphate synthase (GlmS) comprises at least one genetic modification that increases the enzymatic activity of glucosamine-6-phosphate synthase (GlmS).

In another aspect, the gene copy number of the gene encoding the glucosamine-6-phosphate synthase (GlmS) is increased in the recombinant nucleic acid molecule.

In another aspect, the recombinant nucleic acid molecule comprises an endogenous native promoter, a promoter having a higher expression level than the endogenous native promoter, an enhancer, a fusion sequence, and the like. Preferably, the recombinant nucleic acid molecule comprises a promoter having a higher expression level than the endogenous natural promoter, such as an HCE promoter, a gap promoter, a trc promoter, a T7 promoter, etc.; more preferably, the recombinant nucleic acid molecule comprises a trc promoter.

In the present invention, the recombinant nucleic acid molecule transformed into a microorganism is selected from the group consisting of a free form (i.e., a recombinant nucleic acid molecule is loaded into a plasmid) and an integrated type (i.e., a recombinant nucleic acid molecule is integrated into the genome of the microorganism). Preferably, the recombinant nucleic acid molecule is integrated into the genome of the microorganism.

In another preferred embodiment, the microorganism comprises at least one genetic modification of an endogenous native promoter of a gene encoding glucosamine-6-phosphate synthase (GlmS). Preferably, the endogenous native promoter of the gene encoding glucosamine-6-phosphate synthase (GlmS) is replaced by a promoter with a higher expression level, such as the HCE promoter, the gap promoter, the trc promoter, the T7 promoter, etc. More preferably, the endogenous native promoter of the gene encoding glucosamine-6-phosphate synthase (GlmS) is replaced by the trc promoter.

In the present invention, the genetic modification that reduces the effect of D-glucosamine-6-phosphate deaminase (NagB) in the microorganism is selected from a) decreasing the enzymatic activity of D-glucosamine-6-phosphate deaminase (NagB) in the microorganism; and/or b) reducing the expression of D-glucosamine-6-phosphate deaminase (NagB) in the microorganism, including but not limited to: partial or complete deletion or partial or complete inactivation of the endogenous gene encoding D-glucosamine-6-phosphate deaminase (NagB) in the microorganism, and/or partial or complete deletion or partial or complete inactivation of the endogenous natural promoter of gene encoding D-glucosamine-6-phosphate deaminase (NagB) in the microorganism. Preferably, the genetic modification that reduces the effect of D-glucosamine-6-phosphate deaminase (NagB) in the microorganism is the complete missing, that is, deletion of the endogenous natural promoter of D-glucosamine-6-phosphate deaminase (NagB) gene in the microorganism.

In a specific embodiment, the microorganism is transformed with at least one recombinant nucleic acid molecule comprising at least one genetic modification that reduces the effect of D-glucosamine-6-phosphate deaminase (NagB) in the microorganism.

In the above aspect (3), the genetic modification for enhancing the effect of UDP-N-acetyl-D-glucosamine-2-epimerase (WecB) in the microorganism is selected from the group consisting of a) increasing the enzymatic activity of UDP-N-acetyl-D-glucosamine-2-epimerase (WecB) in the microorganism, and/or b) overexpressing UDP-N-acetyl-D-glucosamine-2-epimerase (WecB) in the microorganism.

It will be understood by those skilled in the art that enhancing the effect of UDP-N-acetyl-D-glucosamine-2-epimerase (WecB) in the microorganisms can be achieved by screening gene mutations that encode UDP-N-acetyl-D-glucosamine-2-epimerase (WecB) with an increased enzyme activity. Screening for WecB gene mutations can be accomplished by error-prone PCR techniques to obtain high frequency mutant genes. Enhancing the effect of UDP-N-acetyl-D-glucosamine-2-epimerase (WecB) in microorganisms can also be achieved by increasing the number of copies of the gene or replacing the native promoter with a promoter having a higher expression level than the native promoter to overexpress UDP-N-acetyl-D-glucosamine-2-epimerase (WecB). In a specific embodiment, the microorganism is transformed with at least one recombinant nucleic acid molecule comprising at least one genetic modification that enhances the effect of UDP-N-acetyl-D-glucosamine-2-epimerase (WecB) in the microorganism.

In a preferred embodiment, the microorganism is transformed with at least one recombinant nucleic acid molecule comprising a nucleic acid sequence encoding UDP-N-acetyl-D-glucosamine-2-epimerase (WecB).

In one aspect, the nucleic acid sequence encoding UDP-N-acetyl-D-glucosamine-2-epimerase (WecB) contains at least one genetic modification that increases the enzymatic activity of UDP-N-acetyl-D-glucosamine-2-epimerase (WecB); further preferably, the genetic modification comprises one or more of the substitutions at positions corresponding to the amino acid sequence of SEQ ID NO: 43: the 34th cysteine is replaced by serine, the 145th histidine is replaced by aspartic acid, the 226th cysteine is replaced by phenylalanine, and the 245th valine is replaced by glycine; more preferably, the nucleic acid sequence encoding D-glucosamine-2-epimerase (WecB) is SEQ ID NO: 49; the amino acid sequence of the UDP-N-acetyl-D-glucosamine-2-epimerase (WecB) is SEQ ID NO: 50.

In another aspect, the amino acid sequence of the UDP-N-acetyl-D-glucosamine-2-epimerase (WecB) has at least about 30% identity of the amino acid sequence of SEQ ID NO:43; preferably at least about 50% identity; further preferably at least about 700/% identity; further preferably at least about 80% identity; still more preferably at least about 90% identity; and most preferably at least about 95% identity, wherein said UDP-N-acetyl-D-glucosamine-2-epimerase (WecB) has enzymatic activity.

In another aspect, the amino acid sequence of UDP-N-acetyl-D-glucosamine-2-epimerase (WecB) has the amino acid sequence of SEQ ID NO:43.

In another aspect, the gene copy number of the gene encoding UDP-N-acetyl-D-glucosamine-2-epimerase (WecB) is increased in the recombinant nucleic acid molecule.

In another aspect, the recombinant nucleic acid molecule comprises an endogenous native promoter, a promoter having a higher expression level than the endogenous native promoter, an enhancer, a fusion sequence, and the like. Preferably, the recombinant nucleic acid molecule comprises a promoter having a higher expression level than the endogenous natural promoter, such as an HCE promoter, a gap promoter, a trc promoter, a T7 promoter, etc.; more preferably, the recombinant nucleic acid molecule comprises a trc promoter.

In the present invention, the recombinant nucleic acid molecule transformed into a microorganism is selected from the group consisting of a free form (i.e., a recombinant nucleic acid molecule is loaded into a plasmid) and an integrated type (i.e., a recombinant nucleic acid molecule is integrated into the genome of the microorganism). Preferably, the recombinant nucleic acid molecule is integrated into the genome of the microorganism.

In another preferred embodiment, the microorganism comprises at least one genetic modification of an endogenous native promoter of a gene encoding UDP-N-acetyl-D-glucosamine-2-epimerase (WecB). Preferably, the endogenous native promoter of the gene encoding UDP-N-acetyl-D-glucosamine-2-epimerase (WecB) is replaced by a promoter with a higher expression level, such as the HCE promoter, the gap promoter, the trc promoter, the T7 promoter and the like; more preferably, the endogenous natural promoter of the gene encoding UDP-N-acetyl-D-glucosamine-2-epimerase (WecB) is replaced by the trc promoter.

According to a preferred embodiment of the invention, the microorganism further comprises one or more of the following genetic modifications:
  (1) Comprising at least one genetic modification capable of reducing the effect of the mannose transporter EIIM, P/III$^{man}$ (ManXYZ) in the microorganism;
  (2) Comprising at least one genetic modification capable of reducing the effect of N-acetylneuraminic acid lyase (NanA) in the microorganism;
  (3) Comprising at least one genetic modification capable of reducing the effect of N-acetyl-D-glucosamine-6-phosphate deacetylase (NagA) in the microorganism;
  (4) Comprising at least one genetic modification capable of reducing the effect of the N-acetyl-D-glucosamine specific enzyme II$^{Nag}$ (NagE) in the microorganism;
  (5) Comprising at least one genetic modification capable of increasing the effect of a phosphoglucosamine mutase (GlmM) in the microorganism;
  (6) Comprising at least one genetic modification capable of enhancing the effect of the bifunctional enzyme N-acetyl-D-glucosamine-1-phosphate uridine acyltransferase (GlmU) in the microorganism.

In the above aspect (1), the genetic modification of reducing the effect of the mannose transporter EIIM, P/III$^{man}$ (ManXYZ) in the microorganism includes, but is not limited to, partial or complete deletion, or partial or complete inactivation of the endogenous gene encoding the mannose transporter EIIM, P/III$^{man}$ (ManXYZ) in the microorganism, and/or partial or complete deletion, or partial or complete inactivation of the endogenous natural promoter of endogenous gene encoding the mannose transporter EIIM, P/III$^{man}$ (ManXYZ) in the microorganism. Preferably, the genetic modification of reducing the effect of the mannose transporter EIIM, P/III$^{man}$ (ManXYZ) in the microorganism is the complete missing, i.e., deletion of the endogenous gene encoding the mannose transporter EIIM, P/III$^{man}$ (ManXYZ) in the microorganism. In a specific embodiment, the microorganism is transformed with at least one recombinant nucleic acid molecule comprising at least one genetic modification that reduces the effect of the mannose transporter EIIM, P/III$^{man}$ (ManXYZ) in the microorganism.

In the above aspect (2), the genetic modification for reducing the effect of N-acetylneuraminic acid lyase (NanA) in the microorganism includes, but is not limited to, partial or complete deletion, or partial or complete inactivation of the endogenous gene encoding N-acetylneuraminic acid lyase (NanA) in the microorganism, and/or partial or complete deletion, or partial or complete inactivation of the endogenous natural promoter of the gene encoding N-acetylneuraminic acid lyase (NanA) in the microorganism. Preferably, the genetic modification that reduces the effect of N-acetylneuraminic acid lyase (NanA) in the microorganism is the complete missing, i.e., deletion of the endogenous gene encoding the N-acetylneuraminic acid lyase (NanA). In a specific embodiment, the microorganism is transformed with at least one recombinant nucleic acid molecule comprising at least one genetic modification that reduces the effect of N-acetylneuraminic acid lyase (NanA) in the microorganism.

In the above aspect (3), the genetic modifications for reducing the effect of N-acetyl-D-glucosamine-6-phosphate deacetylase (NagA) in the microorganism includes, but is not limited to, partial or complete deletion, or partial or complete inactivation of the endogenous gene encoding the N-acetyl-D-amino group in the microorganism, and/or partial or complete deletion, or partial or complete inactivation of the endogenous natural promoter of the gene encoding glucose-6-phosphate deacetylase (NagA) in the microorganism. Preferably, the genetic modification that reduces the effect of N-acetyl-D-glucosamine-6-phosphate deacetylase (NagA) in the microorganism is the complete missing, i.e., deletion of the endogenous gene encoding N-acetyl-D- glucosamine-6-phosphate deacetylase (NagA) in the microorganism. In a specific embodiment, the microorganism is transformed with at least one recombinant nucleic acid molecule comprising at least one genetic modification that reduces the effect of N-acetyl-D-glucosamine-6-phosphate deacetylase (NagA) in the microorganism.

In the above aspect (4), the genetic modification for reducing the effect of the N-acetyl-D-glucosamine specific enzyme II$^{Nag}$ (NagE) in the microorganism includes, but is not limited to, partial or complete deletion, or partial or complete inactivation of the endogenous gene encoding N-acetyl-D-glucosamine specific enzyme II$^{Nag}$ (NagE) in the microorganism. and/or partial or complete deletion, or partial or complete inactivation of the endogenous natural promoter of the gene encoding N-acetyl-D-glucosamine specific enzyme II$^{Nag}$ (NagE) in the microorganism. Preferably, the genetic modification to reduce the effect of the N-acetyl-D-glucosamine specific enzyme II$^{Nag}$ (NagE) in the microorganism is a complete missing, i.e., deletion of the endogenous gene encoding N-acetyl-D-glucosamine specific enzyme II$^{Nag}$ (NagE) in the microorganism. In a specific embodiment, the microorganism is transformed with at least one recombinant nucleic acid molecule comprising at least one genetic modification that reduces the effect of the N-acetyl-D-glucosamine specific enzyme II$^{Nag}$ (NagE) in the microorganism.

In the above aspect (5), the genetic modification for increasing the effect of the phosphoglucosamine mutase (GlmM) in the microorganism is selected from a) increasing the enzymatic activity of the phosphoglucosamine mutase (GlmM) in the microorganism; and/or b) overexpressing phosphoglucosamine mutase (GlmM) in the microorganism.

It will be understood by those skilled in the art that enhancing the effect of phosphoglucosamine mutase (GlmM) in a microorganism can be achieved by screening for gene mutations that encode phosphoglucosamine mutase (GlmM) with an increased enzymatic acitvity. Screening of GlmM gene mutations can be accomplished by error-prone PCR techniques to obtain high frequency mutant genes. Enhance the effect of phosphoglucosamine mutase (GlmM) in microorganisms can also be achieved by overexpressing phosphoglucosamine mutase by increasing its gene copy number and replacing a promoter with a higher expression level than the native promoter. In a specific embodiment, the microorganism is transformed with at least one recombinant nucleic acid molecule comprising at least one genetic modification that enhances the effect of phosphoglucosamine mutase (GlmM) in the microorganism.

In a preferred embodiment, the microorganism is transformed with at least one recombinant nucleic acid molecule comprising a nucleic acid sequence encoding a phosphoglucosamine mutase (GlmM).

In one aspect, the nucleic acid sequence encoding a phosphoglucosamine mutase (GlmM) comprises at least one genetic modification that increases the enzymatic activity of a phosphoglucosamine mutase (GlmM).

In another aspect, the gene copy number of the gene encoding the phosphoglucosamine mutase (GlmM) is increased in the recombinant nucleic acid molecule.

In another aspect, the recombinant nucleic acid molecule comprises an endogenous native promoter, a promoter having a higher expression level than the endogenous native promoter, an enhancer, a fusion sequence, and the like. Preferably, the recombinant nucleic acid molecule comprises a promoter having a higher expression level than the endogenous natural promoter, such as an HCE promoter, a gap promoter, a trc promoter, a T7 promoter, etc.; more preferably, the recombinant nucleic acid molecule comprises a trc promoter.

In the present invention, the recombinant nucleic acid molecule transformed into a microorganism is selected from the group consisting of a free form (i.e., a recombinant nucleic acid molecule is loaded into a plasmid) and an integrated type (i.e., a recombinant nucleic acid molecule is integrated into the genome of the microorganism). Preferably, the recombinant nucleic acid molecule is integrated into the genome of the microorganism.

In another preferred embodiment, the microorganism comprises at least one genetic modification of an endogenous native promoter of a gene encoding a phosphoglucosamine mutase (GlmM). Preferably, the endogenous native promoter encoding the gene for phosphoglucosamine mutase (GlmM) is replaced by a promoter with a higher expression level, such as the HCE promoter, gap promoter, trc promoter, T7 promoter, etc. More preferably, the endogenous native promoter of the gene encoding the phosphoglucosamine mutase (GlmM) is replaced by the trc promoter.

In the above aspect (6), the genetic modification for enhancing the effect of the bifunctional enzyme N-acetyl-D-glucosamine-1-phosphate uridine acyltransferase (GlmU) in the microorganism is selected from a) increasing the enzymatic activity of bifunctional enzyme N-acetyl-D-glucosamine-1-phosphate uridine acyltransferase (GlmU); and/or b) overexpressing bifunctional enzyme N-acetyl-D-glucosamine-1-phosphate uridine acyltransferase (GlmU) in microorganisms.

It will be understood by those skilled in the art that enhancing the effect of bifunctional enzyme N-acetyl-D-glucosamine-1-phosphate uridine acyltransferase (GlmU) in microorganisms can be achieved by screening gene mutations that encode bifunctional enzyme N-acetyl-D-glucosamine-1-phosphate uridine acyltransferase (GlmU) with an increased enzymatic activity. Screening of the GlmU gene mutations can be accomplished by error-prone PCR techniques to obtain high frequency mutant genes. Increasing the effect of the bifunctional enzyme N-acetyl-D-glucosamine-1-phosphate uridine acyltransferase (GlmU) in microorganisms can also be achieved by overexpressing the bifunctional enzyme N-acetyl-D-glucosamine-1-phosphate uridine acyltransferase (GlmU) through increasing the gene copy number and replacing the natural promoter with a promoter with a higher expression level. In a specific embodiment, the microorganism comprises at least one genetically modified recombinant nucleic acid comprising at least one genetic modification that enhances the effect of the bifunctional enzyme N-acetyl-D-glucosamine-1-phosphate uridine acyltransferase (GlmU) in the microorganism.

In a preferred embodiment, the microorganism is transformed with at least one recombinant nucleic acid molecule comprising a nucleic acid sequence encoding the bifunctional enzyme N-acetyl-D-glucosamine-1-phosphate uridine acyltransferase (GlmU).

In one aspect, the nucleic acid sequence encoding the bifunctional enzyme N-acetyl-D-glucosamine-1-phosphate uridine acyltransferase (GlmU) comprises at least one genetic modification that enhances the effect of the enzymatic activity of the bifunctional enzyme N-acetyl-D-glucosamine-1-phosphouridine syltransferase (GlmU).

In another aspect, the gene copy number of the gene encoding the bifunctional enzyme N-acetyl-D-glucosamine-1-phosphate uridine acyltransferase (GlmU) is increased in the recombinant nucleic acid molecule.

In another aspect, the recombinant nucleic acid molecule comprises an endogenous native promoter, a promoter having a higher expression level than the endogenous native promoter, an enhancer, a fusion sequence, and the like. Preferably, the recombinant nucleic acid molecule comprises a promoter having a higher expression level than the endogenous natural promoter, such as an HCE promoter, a gap promoter, a trc promoter, a T7 promoter, etc.; more preferably, the recombinant nucleic acid molecule comprises a trc promoter.

In the present invention, the recombinant nucleic acid molecule transformed into a microorganism selected from the group consisting of a free form (i.e., a recombinant nucleic acid molecule is loaded into a plasmid) and an integrated type (i.e., a recombinant nucleic acid molecule is integrated into the genome of the microorganism). Preferably, the recombinant nucleic acid molecule is integrated into the genome of the microorganism.

In another preferred embodiment, the microorganism comprises at least one genetic modification of the endogenous natural promoter of the gene encoding the bifunctional enzyme N-acetyl-D-glucosamine-1-phosphate uridyltransferase (GlmU). Preferably, the endogenous native promoter of the gene encoding the bifunctional enzyme N-acetyl-D-glucosamine-1-phosphate uridine acyltransferase (GlmU) is replaced by a promoter with a higher expression level, such as the HCE promoter, a gap promoter, a trc promoter, a T7 promoter, etc.; more preferably, the endogenous natural promoter of the gene encoding the bifunctional enzyme N-acetyl-D-glucosamine-1-phosphate uridine acyltransferase (GlmU) is replaced by the trc promoter.

The invention further relates to the following preferred embodiments:

1. According to a preferred embodiment of the invention, the invention relates to a process for the production of N-acetyl-D-glucosamine (GlcNAc) and/or D-glucosamine salts by microbial fermentation, the process comprising:
   A.) Cultivating a microorganism in a fermentation medium, the microorganism comprises: at least one genetic modification capable of increasing the effect of N-acetyl-D-aminomannose-6-phosphate epimerase (NanE) in the microorganism; and at least one genetic modification that enhances the effect of D-glucosamine-6-phosphate deaminase (NagB) in the microorganism; and
   B.) Collecting the N-acetyl-D-glucosamine (GlcNAc) produced from the cultivating step A).

Preferably, the microorganism further comprises at least one genetic modification that reduces the effect of glucosamine-6-phosphate synthase (GlmS).

2. According to another preferred embodiment of the invention, the invention relates to a process for the production of N-acetyl-D-glucosamine (GlcNAc) and/or D-glucosamine salts by microbial fermentation, the process comprising:
   A.) Cultivating a microorganism in a fermentation medium, the microorganism comprises: at least one genetic modification capable of enhancing the effect of N-acetyl-D-aminomannose-6-phosphate epimerase (NanE) in the microorganism; at least one genetic modification that enhances the effect of glucosamine-6-phosphate synthase (GlmS) in the microorganism; and at least one genetic modification that reduces the effect of D-glucosamine-6-phosphate deaminase (NagB); and
   B.) Collecting the N-acetyl-D-glucosamine (GlcNAc) produced from the cultivating step A).

3. According to another preferred embodiment of the invention, the invention relates to a process for the production of N-acetyl-D-glucosamine (GlcNAc) and/or D-glucosamine salts by microbial fermentation, the process comprising:
   A.) Cultivating a microorganism in a fermentation medium, the microorganism comprises: at least one genetic modification capable of increasing the effect of N-acetyl-D-aminomannose-6-phosphate epimerase (NanE) in the microorganism; and at least one genetic modification that enhances the effect of UDP-N-acetyl-D-glucosamine-2-epimerase (WecB) in microorganisms; and
   B.) Collecting of N-acetyl-D-glucosamine (GlcNAc) produced from the cultivating step A).

4. According to another preferred embodiment of the invention, the invention relates to a process for the production of N-acetyl-D-glucosamine (GlcNAc) and/or D-glucosamine salts by microbial fermentation, the process comprising:
   A.) Cultivating a microorganism in a fermentation medium, the microorganism comprises: at least one genetic modification capable of enhancing the effect of N-acetyl-D-aminomannose-6-phosphate epimerase (NanE) in the microorganism; at least one genetic modification capable of enhancing the effect of D-glucosamine-6-phosphate deaminase (NagB) in the microorganism; and at least one genetic modification capable of enhancing the effect of UDP-N-acetyl-D-glucosamine-2-epimerase (WecB) in the microorganism; and
   B.) Collecting of N-acetyl-D-glucosamine (GlcNAc) produced from the cultivating step A).

Preferably, the microorganism further comprises at least one genetic modification that reduces the effect of glucosamine-6-phosphate synthase (GlmS).

5. According to another preferred embodiment of the invention, the invention relates to a process for the production of N-acetyl-D-glucosamine (GlcNAc) and/or D-glucosamine salts by microbial fermentation, the process comprising:
   A.) Cultivating a microorganism in a fermentation medium, the microorganism comprises: at least one genetic modification capable of enhancing the effect of N-acetyl-D-aminomannose-6-phosphate epimerase (NanE) in the microorganism; at least one genetic modification capable of increasing the effect of glucosamine-6-phosphate synthase (GlmS) in the microorganism; at least one genetic modification that reduces the effect of D-glucosamine-6-phosphate deaminase (NagB); and at least one genetic modification capable of enhancing the effect of UDP-N-acetyl-D-glucosamine-2-epimerase (WecB) in the microorganism; and
   B.) Collecting of N-acetyl-D-glucosamine (GlcNAc) produced from the cultivating step A).

The preferred embodiments of the above further comprises: C) deacetylating N-acetyl-D-glucosamine (GlcNAc) to produce D-glucosamine salts.

In the preferred embodiments of the above, the microorganism further comprises: at least one genetic modification capable of reducing the effect of the mannose transporter EIIM, P/III$^{man}$ (ManXYZ) in the microorganism; at least one genetic modification capable of reducing the effect of N-acetylneuraminic acid lyase (NanA) in the microorganism; at least one genetic modification that reduces the effect of N-acetyl-D-glucosamine-6-phosphate deacetylase (NagA) in the microorganism; and at least one genetic modification that reduces the effect of N-acetyl-D-glucosamine specific enzyme II$^{Nag}$ (NagE) in the microorganism.

In one aspect of any of the above embodiments, the expression of any of the recombinant nucleic acid molecules described above is inducible, including, but not limited to, induced by lactose, for example, by adding lactose or the like to the culture broth to achieve lactose induced expression.

Those skilled in the art will appreciate that various conventional fermentation media known in the art can be used in the present invention. In one aspect, the fermentation medium comprises a source of carbon. In another aspect, the fermentation medium comprises a source of nitrogen. In another aspect, the fermentation medium comprises a source of carbon and a source of nitrogen. In another aspect, the fermentation medium comprises a carbon source, a nitrogen source, and an inorganic salt.

Those skilled in the art will appreciate that a variety of carbon sources known in the art can be used in the present invention, including organic carbon sources and/or inorganic carbon sources. Preferably, the carbon source is selected from one or more of the group consisting of glucose, fructose, sucrose, galactose, dextrin, glycerin, starch, syrup, and molasses. Preferably, the concentration of the carbon source is maintained at from about 0.1% to about 5%. Those skilled in the art will appreciate that a variety of nitrogen sources known in the art can be used in the present invention, including organic nitrogen sources and/or inorganic nitrogen sources. Preferably, the nitrogen source is selected from one or more of the group consisting of ammonia, ammonium chloride, ammonium sulfate, ammonium nitrate, ammonium acetate, sodium nitrate, urea, yeast extract, meat extract, peptone, fish meal, soy flour, malt, corn syrup and cottonseed powder.

Preferably, the present invention utilizes a fed fermentation process. According to one aspect of the invention, the supplemental sugar solution comprises glucose and ribose. Preferably, the glucose concentration is from 10% to 85% (w/v), the ribose concentration is from 0.5% to 15% (w/v); further preferably, the glucose concentration is 55%-75% (w/v), ribose concentration is 5%-7% (w/v). According to another aspect of the invention, the supplemental sugar solution comprises glucose and gluconate. Preferably, the glucose concentration is 10%-85% (w/v), the gluconate concentration is 0.5%-15% (w/v); further preferably, the glucose concentration is 55%-75% (w/v), the gluconate concentration is 2%-3% (w/v). According to another aspect of the invention, the supplemental sugar solution comprises glucose, ribose and gluconate, and preferably having a glucose concentration of 10%-85% (w/v), a ribose concentration of 0.5. %-15% (w/v), and a gluconate concentration of 0.5%-15% (w/v); further preferably, the glucose concentration is 55%-75% (w/v), the ribose concentration is 5%-7% (w/v), and the gluconate concentration is 2%-3% (w/v). Preferably, the gluconate is sodium gluconate.

In a preferred embodiment, the culturing step is carried out at a temperature of from about 20° C. to about 45° C., and more preferably, the culturing step is carried out at a temperature of from about 33° C. to about 37° C.

In a preferred embodiment, the culturing step is carried out at a pH of from about 4.5 to about pH 8.5. In one aspect, the culturing step is performed at about pH 6.7 to about pH7.2.

Those skilled in the art will appreciate that N-acetyl-D-glucosamine (GlcNAc) can be collected in the present invention using various conventional methods known in the art. Preferably, N-acetyl-D-glucosamine can be collected from the extracellular product in the fermentation medium. Further preferably, the collecting step comprises the step of: (a) precipitating N-acetyl-D-glucosamine from the fermentation broth after removing microorganisms; (b) crystallizing N-acetyl-D-Glucosamine from the fermentation broth after removing microorganisms.

According to the invention, the collecting step further comprises the step of decolorizing the fermentation broth. The decolorizing step may be performed include, but is not limited to, prior to precipitation or crystallization of the fermentation broth, or after one or more precipitation or crystallization re-dissolution of the fermentation broth; decolorization includes activated carbon treatment and/or chromatographic decolorization. The chromatographic decolorization comprises the step of contacting the fermentation broth with an ion exchange resin; the ion exchange resin includes but not limited to an anion exchange resin and/or a cation exchange resin, for example, contacting the fermentation broth with a mixed bed of anion and cation exchange resin.

According to the present invention, D-glucosamine salts can be obtained by deacetylating N-acetyl-D-glucosamine. The salts include but not limited to hydrochloride acid salts, sulfates, sodium salts, phosphates, hydrogen sulfates and the like. For example, the N-acetyl-D-glucosamine can be deacetylated under acidic and heated conditions to obtain a D-glucosamine salt. Preferably, hydrolyzing N-acetyl-D-glucosamine to deacetylation in a 300/% to 37% hydrochloric acid solution at 60° C. to 90° C. to obtain D-glucosamine salts; also hydrolyzing N-acetyl-D-glucosamine under the action of UDP-3-ON-acetylglucosamine deacetylase to obtain D-glucosamine, and further into salts.

According to another embodiment of the present invention, the present invention relates to a microorganism comprising at least one genetic modification capable of enhancing the effect of N-acetyl-D-aminomannose-6-phosphate epimerase (NanE) in a microorganism. This genetic modification has been described above in detail.

According to a preferred embodiment of the invention, the microorganism further comprises one or more of the following genetic modifications:

(1) Comprising at least one genetic modification capable of enhancing the effect of D-glucosamine-6-phosphate deaminase (NagB) in a microorganism, preferably comprising at the same time at least one genetic modification capable of reducing the effect of glucosamine-6-phosphate synthase (GlmS);

(2) Comprising at least one genetic modification capable of increasing the effect of glucosamine-6-phosphate synthase (GlmS) in the microorganism, and at the same time comprising at least one genetic modification capable of reducing the effect of D-glucosamine-6-phosphate deaminase (NagB);

(3) Comprising at least one genetic modification capable of enhancing the effect of UDP-N-acetyl-D-glucosamine-2-epimerase (WecB) in the microorganism. These genetic modifications have been described above in detail.

According to a preferred embodiment of the invention, the microorganism further comprises one or more of the following genetic modifications:

(1) At least one genetic modification capable of reducing the effect of the mannose transporter EIIM, P/III$^{man}$ (ManXYZ) in the microorganism;
(2) At least one genetic modification capable of reducing the effect of N-acetylneuraminic acid lyase (NanA) in the microorganism;
(3) At least one genetic modification capable of reducing the effect of N-acetyl-D-glucosamine-6-phosphate deacetylase (NagA) in the microorganism;
(4) At least one genetic modification capable of reducing the effect of the N-acetyl-D-glucosamine specific enzyme II$^{Nag}$ (NagE) in the microorganism;
(5) At least one genetic modification capable of increasing the effect of a phosphoglucosamine mutase (GlmM) in the microorganism;
(6) At least one genetic modification capable of enhancing the effect of the bifunctional enzyme N-acetyl-D-glucosamine-1-phosphate uridine acyltransferase (GlmU) in the microorganism. These genetic modifications have been described above in detail.

The invention further relates to the following preferred embodiments:

1. According to a preferred embodiment of the invention, the invention relates to a microorganism comprising: at least one genetic modification capable of enhancing the effect of N-acetyl-D-aminomannose-6-phosphate epimerase (NanE) in the microorganism; and at least one genetic modification capable of enhancing the action of D-glucosamine-6-phosphate deaminase (NagB) in the microorganism.

Preferably, the microorganism further comprises at least one genetic modification that reduces the effect of glucosamine-6-phosphate synthase (GlmS).

2. According to another preferred embodiment of the present invention, the present invention relates to a microorganism comprising: at least one genetic modification capable of increasing the effect of N-acetyl-D-aminomannose-6-phosphate epimerase (NanE) in the microorganism; at least one genetic modification that increases the effect of glucosamine-6-phosphate synthase (GlmS) in the microorganism; and at least one genetic modification that reduces the effect of D-glucosamine-6-phosphate deaminase (NagB).

3. According to a preferred embodiment of the invention, the invention relates to a microorganism comprising: at least one genetic modification capable of enhancing the effect of N-acetyl-D-aminomannose-6-phosphate epimerase (NanE) in the microorganism; and at least one genetic modification capable of enhancing the effect of UDP-N-acetyl-D-glucosamine-2-epimerase (WecB) in the microorganism.

4. According to another preferred embodiment of the present invention, the present invention relates to a microorganism comprising: at least one genetic modification capable of increasing the effect of N-acetyl-D-aminomannose-6-phosphate epimerase (NanE) in the microorganism; at least one genetic modification that enhances the effect of D-glucosamine-6-phosphate deaminase (NagB) in the microorganism; and at least one genetic modification that increases the effect of UDP-N-acetyl-D-glucosamine-2-epimerase (WecB) in the microorganism.

Preferably, the microorganism further comprises at least one genetic modification that reduces the effect of glucosamine-6-phosphate synthase (GlmS).

5. According to another preferred embodiment of the present invention, the present invention relates to a microorganism comprising: at least one genetic modification capable of increasing the effect of N-acetyl-D-aminomannose-6-phosphate epimerase (NanE) in the microorganism; at least one genetic modification that enhances the effect of glucosamine-6-phosphate synthase (GlmS) in the microorganism; at least one genetic modification that reduces the effect of D-glucosamine-6-phosphate deaminase (NagB); and at least one genetic modification that enhances the effect of UDP-N-acetyl-D-glucosamine-2-epimerase (WecB) in the microorganism.

In the preferred embodiments of the above, the microorganism further comprises: at least one genetic modification capable of reducing the effect of the mannose transporter EIIM, P/III$^{man}$(ManXYZ) in the microorganism; at least one genetic modification capable of reducing the effect of N-acetylneuramin acid lyase (NanA) in the microorganism; at least one genetic modification that reduces the effect of N-acetyl-D-glucosamine-6-phosphate deacetylase (NagA) in the microorganism; and at least one genetic modification that reduces the effect of N-acetyl-D-glucosamine specific enzyme II$^{Nag}$ (NagE) in the microorganism.

According to another embodiment of the present invention, the present invention relates to an N-acetyl-D-aminomannose-6-phosphate epimerase (NanE) having a higher enzymatic activity and having the amino acid sequence of SEQ ID NO: 27. The present invention further relates to a nucleic acid molecule encoding the above N-acetyl-D-aminomannose-6-phosphate epimerase (NanE) and having the nucleic acid sequence of SEQ ID NO: 26. The invention further relates to a vector comprising the above nucleic acid molecule. The invention further relates to a microorganism comprising the above vector. The invention further relates to a microorganism comprising the above nucleic acid molecule in the genome.

In the present invention, the microorganism may be any microorganism (e.g., bacteria, protist, algae, fungus or other microorganisms). In a preferred embodiment, the microorganism includes, but not limited to, bacteria, yeast or fungi. Preferably, the microorganism is selected from the group consisting of bacteria or yeast. Further preferably, the bacterium includes, but not limited to, a bacterium selected from the group consisting of *Escherichia, Bacillus, Lactobacillus, Pseudomonas,* or *Streptomyces*. More preferably, the bacterium includes, but not limited to, a bacterium selected from the group consisting of *Escherichia coli, Bacillus subtilis, Bacillus licheniformis, Lactobacillus brevis, Pseudomonas aeruginosa* or a species of *Streptomyces lividans*. Further preferably, the yeast includes, but not limited to, a yeast selected from the group consisting of *Saccharomyces, Schizosaccharomyces, Candida, Hansenula, Pichia, Kluveromyces* and *Phaffia*; more preferably, the yeast includes, but not limited to, *Saccharomyce scerevisiae, Schizosaccharo mycespombe, Candida albicans, Hansenulapolymorpha, Pichia pastoris, Pichia canadensis, Kluyveromyces marxianus* or *Phaffia rohodozyma*. Preferably, the microorganism is a fungus; further preferably, the fungus includes, but not limited to, a fungus selected from the group consisting of *Aspergillus, Absidia, Rhizopus, Chrysosporium, Neurospora* or *Trichoderma*; more preferably, the fungus includes, but not limited to, a fungus selected from the group consisting of *Aspergillus niger, Aspergillus nidulans, Absidia coerulea, Rhizopus oryzae, Chrysosporium lucknowense, Neurospora crassa, Neurospora intermedia* or *Trichoderma reesei*. Particularly preferably, the *E. coli* strains include K-12, B and W, and most preferably K-12. Although *E. coli* is a preferred microorganism and is used as an example of various embodiments of the present invention, it is understood that any other microorganism can be used in the present invention to produce N-acetyl-D-glucosamine, and can be genetically modified to increase the yield of N-acetyl-D-glucosamine. The microorganism used in the present invention may also be referred to as a production organism.

In the present invention, the term N-acetyl-D-glucosamine may be referred to as 2-acetamido-2-deoxy-D-glucose. The terms N-acetyl-D-glucosamine, N-acetyl-D-glucosamine-6-phosphate and N-acetyl-D-glucosamine-1-phosphate can be abbreviated as GlcNAc, GlcNAc-6-P and GlcNAc-1-P, respectively. N-acetyl-D-glucosamine is also abbreviated as NAG. Similar to N-acetyl-D-glucosamine and derivatives, the terms D-glucosamine, D-glucosamine-6-phosphate and D-glucosamine-1-phosphate can be abbreviated as GlcN, GlcN-6-P and GlcN-1-P, respectively. Similarly, the terms N-acetyl-D-aminomannose, N-acetyl-D-aminomannose-6-phosphate, glucose, glucose-6-phosphate, fructose-6-phosphate can be abbreviated as ManNAc, ManNAc-6-P, Glc, Glc-6-P, and Fru-6-P, respectively.

The term "increasing/enhancing the effect of" an enzyme in a microorganism means that the activity of the enzyme in the microorganism is increased and/or the enzyme is over-expressed, thereby increasing the amount of product produced by the substrate catalyzed by the enzyme in the microorganism.

The term "reducing the effect of" an enzyme in a microorganism means that the activity of the enzyme in the microorganism is reduced and/or the expression of the enzyme is reduced, thereby reducing the amount of product produced by the substrate catalyzed by the enzyme in the microorganism.

The term "increased/enhanced enzyme/enzymatic activity" refers to an increased ability of an enzyme to catalyze a certain chemical reaction. It covers an increase in the ability of the enzyme to self-catalyze a chemical reaction in the event that the enzyme is inhibited by the product and there is no change in the enzyme substrate affinity, and/or an increased ability of an enzyme to catalyze a chemical reaction due to the decreased inhibition of the enzyme products and/or increased enzyme substrate affinity. The term decreased enzyme/enzymatic activity means that the activity of enzyme in a catalytic reaction is reduced by the specific inhibition of its end product. The term increased enzyme substrate affinity refers to an increase in the affinity of the enzyme to the substrate being catalyzed.

FIG. 1 illustrates, in the case of *E. coli*, the main aspects of the genetic modification of the amino sugar metabolic pathway disclosed in the present invention for the large-scale production of N-acetyl-D-glucosamine. With respect to FIG. 1, the bold arrows indicate the production and/or increase of metabolic flow through the genetic modifications disclosed in the present invention. FIG. 1 discloses several different methods for synthesizing N-acetyl-D-glucosamine, including modifications to NanE, which may further include modifications to NagB, GlmS, WecB, or a combination thereof, and may further include modifications to ManXYZ, NanA, NagA, NagE, GlmM, GlmU, or a combination thereof. Those skilled in the art will appreciate that other microorganisms have similar pathways for sugar metabolism, and that genes and proteins in such pathways have similar structures and functions. Thus, the invention discussed herein is equally applicable to other microorganisms other than *E. coli*, and other microorganisms are expressly included in the present invention.

Enzymes having the same biological activity are known in the art to have different names depending on which microorganism the enzyme is derived from. The following are alternative names for many of the enzymes referred to herein and specific gene names encoding such enzymes from certain organisms. The names of these enzymes may be used interchangeably or, if appropriate, for a given sequence or organism, but the present invention is intended to include enzymes of specific functions from any organism.

For example, an enzyme generally referred to herein as "N-acetyl-D-aminomannose kinase" catalyzes the phosphorylation of N-acetyl-D-aminomannose to N-acetyl-D-aminomannose-6-P. N-acetyl-D-aminomannose kinase from *E. coli* is generally referred to as NanK. N-acetyl-D-aminomannose kinases from various organisms are well known in the art and can be used in the genetic engineering strategies of the present invention.

The enzyme generally referred to herein as "N-acetyl-D-aminomannose-6-P epimerase" catalyzes the conversion of N-acetyl-D-aminomannose-6-P to N-acetyl-D-glucosamine-6-P. The N-acetyl-D-aminomannose-6-P epimerase from *E. coli* is generally referred to as NanE. N-acetyl-D-aminomannose-6-P epimerases from various organisms are well known in the art and can be used in the genetic engineering strategies of the present invention. For example, it is described herein that N-acetyl-D-aminomannose-6-P epimerase from *E. coli* has the amino acid sequence represented by SEQ ID NO: 17 and is encoded by the nucleic acid sequence represented by SEQ ID NO: 16.

An enzyme generally referred to herein as "UDP-N-acetyl-D-glucosamine-2-epimerase" catalyzes the conversion of UDP-N-acetyl-D-glucosamine to N-acetyl-D-aminomannose. UDP-N-acetyl-D-glucosamine-2-epimerase from *E. coli* is generally referred to as WecB. UDP-N-acetyl-D-glucosamine-2-epimerases from various organisms are well known in the art and can be used in the genetic engineering strategies of the present invention. For example, it is described herein that UDP-N-acetyl-D-glucosamine-2-epimerase from *E. coli* has the amino acid sequence represented by SEQ ID NO: 43 and is encoded by the nucleic acid sequence represented by SEQ ID NO: 42.

An enzyme generally referred to herein as "D-glucosamine-6-phosphate deaminase" catalyzes the reversible reaction of D-glucosamine-6-phosphate with water to form glucose-6-phosphate and ammonium. The enzyme is also known as D-glucosamine-6-phosphate epimerase, GlcN6P deaminase, D-glucosamine epimerase, D-glucosamine epimerase, D-glucosamine phosphate deaminase and 2-Amino-2-deoxy-D-glucose-6-phosphate ethyl ketone alcohol epimerase (deamination). D-glucosamine-6-phosphate deaminase from various organisms is well known in the art and can be used in the genetic engineering strategies of the present invention. In *E. coli* and other bacteria, the enzyme is generally referred to as NagB.

An enzyme generally referred to herein as "D-glucosamine-6-phosphate synthase" catalyzes the formation of D-glucosamine-6-phosphate and glutamic acid from glucose-6-phosphate and glutamine. The enzyme is also called D-glucosamine-fructose-6-phosphate aminotransferase (isomerization), hexose phosphate aminotransferase, D-fructose-6-phosphate transamidase, D-glucosamine-6-phosphate epimerase (formation of glutamine), L-glutamine-fructose-6-phosphate transamidase and GlcN6P synthase. D-glucosamine-6-phosphate synthase from various organisms is well known in the art and can be used in the genetic engineering strategies of the present invention.

D-glucosamine-6-phosphate synthase from *E. coli* and other bacteria is generally referred to as GlmS.

An enzyme generally referred to herein as "N-acetyl-D-glucosamine-6-phosphate deacetylase" hydrolyzes N-acetyl-D-glucosamine-6-phosphate to D-glucosamine-6-phosphate and acetate. N-acetyl-D-glucosamine-6-phosphate deacetylases from various organisms are well known in the art and can be used in the genetic engineering strategies of the present invention. For example, it is described herein as NagA from *E. coli*.

An enzyme generally referred to herein as "N-acetylneuraminic lyase" catalyzes the degradation of N-acetyl-D-aminomannose to N-acetylneuraminic acid. N-acetylneuraminic lyases from various organisms are well known in the art and can be used in the genetic engineering strategies of the present invention. For example, the N-acetylneuraminic acid lyase from *E. coli* is described herein as NanA.

An enzyme generally referred to herein as "phosphoglucosamine mutase" catalyzes the conversion of D-glucosamine-6-phosphate to D-glucosamine-1-phosphate. Phospho-D-glucosamine mutases from various organisms are well known in the art and can be used in the genetic engineering strategies of the present invention. The phosphoglucosamine mutase in *E. coli* and other bacteria is generally referred to as GlmM.

An enzyme generally referred to herein as "D-glucosamine-1-phosphate N-acetyltransferase" converts D-glucosamine-1-phosphate and acetyl-CoA to N-acetyl-D-glucosamine-1-phosphate, and release the CoA. As a bifunctional enzyme, it also functions as N-acetyl-D-glucosamine-1-phosphate uridine acyltransferase, also known as UDP-N-acetyl-D-glucosamine pyrophosphorylase, UDP-N-acetyl-D-glucosamine diphosphorylase, and it further converts N-acetyl-D-glucosamine-1-phosphate to UDP-N-acetyl-D-glucosamine. D-glucosamine-1-phosphate N-acetyltransferase and N-acetyl-D-glucosamine-1-phosphate uridine acyltransferase from various organisms are well known in the art and can be used in the genetic engineering strategies of the present invention. This enzyme is called GlmU in *E. coli* and other bacteria.

The "Trc Promoter" is cleverly designed for prokaryotic expression, such as the *E. coli* expression system. The Trc promoter is well known in the art and can be used in the genetic engineering strategy of the present invention. For example, the Trc promoter described herein has the nucleotide sequence represented by SEQ ID NO: 28.

As disclosed in the WO2004/003175 invention, D-glucosamine is extremely unstable in the general pH range used for *E. coli* growth. D-glucosamine and/or its degradation products have toxic effects on the strain. Toxicity is observed even when D-glucosamine having a concentration as low as 20 g/L is pre-insulated for 3.5 hours in the medium (pH 7.0) prior to cell seeding. Toxicity is at least in part due to D-glucosamine degradation products in the medium with a starting pH of 7.0. GlcN is more stable at lower pH conditions and D-glucosamine does not degrade at pH 4.7 or below. However, *E. coli* grows slowly at pH conditions below 6-7. Therefore, the production of D-glucosamine in a fermenter at a relatively low pH is difficult to implement.

According to the present invention, D-glucosamine-6-P (GlcN-6-P) is catalyzed inside the cell by GlmM and GlmU to UDP-N-acetyl-D-glucosamine (UDP-GlcNAc), which is then catalyzed by UDP-N-Acetyl-glucosamine-2-epimerase (WecB) to N-acetyl-D-aminomannose (ManNAc), and through overexpression of NanE, ManNAc is further converted to N-acetyl-D-glucosamine-6-phosphate (GlcNAc-6-P), which is phosphorylated by phosphatase, and excreted out of the cell to become N-acetyl-D-glucosamine (GlcNAc). The method of the present invention avoids the formation of D-glucosamine, thereby avoiding the toxic effects of D-glucosamine and/or its degradation products on the strain.

Therefore, the present invention has the beneficial effects that it proves that the completely natural N-acetyl-D-glucosamine can be directly produced by the microbial fermentation method; the new production method has no risk of heavy metal pollution, no risk of antibiotics and drug residues, and production is not affected by raw material supply, and can achieve long-term stable production with high yield and low cost; N-acetyl-D-glucosamine and D-glucosamine products produced therefore have no animal origin and do not use chitin from shrimp shell; the method utilizes fermentation with carbon sources such as glucose, and is a vegetarian product, and has no allergic source of aquatic products.

The entire disclosures and references cited or described herein are hereby incorporated by reference.

BRIEF DESCRIPTION OF THE DRAWINGS

FIG. 1 illustrates the scheme of N-acetyl-D-glucosamine biosynthesis pathway and metabolic engineering strategy in *Escherichia coli*.

DETAILED DESCRIPTION OF THE PREFERRED EMBODIMENTS

The invention will be further described in detail below with reference to specific embodiments. The following examples are merely illustrative of the invention and are not to be construed as limiting the scope of the invention. The technology implemented based on the present invention is intended to be within the scope of the present invention.

The starting materials and reagents used in the examples are commercially available unless otherwise stated.

The following is a catalog of various genetically modified microorganisms relating to and/or described in the present invention.

| Strain Number | Genotype Description | Note |
|---|---|---|
| AT-001 | ATCC 27325, F-IN(rrnD-rrnE)1 lambda-, the primary culture derivative strains of *E coli* K-12 | Parent strain of engineered bacteria, from American Type Culture Collection (ATCC) |
| AT-002-01 | AT-001, ΔmanXYZ::fKanrf | Example 1 |
| AT-002-02 | AT-001, ΔmanXYZ | Example 1 |
| AT-003-01 | AT-002-02, ΔnanA::fKanrf | Example 1 |
| AT-003-02 | AT-002-02, ΔnanA | Example 1 |
| AT-004-01 | AT-003-02, ΔnagA::fKanrf | Example 1 |
| AT-004-02 | AT-003-02, ΔnagA | Example 1 |
| AT-005-01 | AT-004-02, ΔnagE::fKanrf | Example 1 |
| AT-005-02 | AT-004-02, ΔnagE | Example 1 |
| AT-030-01 | AT-004-02, ΔnagE::pTrc-nanE-fKanrf | Example 2 |
| AT-030-02 | AT-004-02, ΔnagE::pTrc-nanE | Example 2 |
| AT-031-01 | AT-004-02, ΔnagE::pTrc-nanEM-fKanrf | Example 3 |
| AT-031-02 | AT-004-02, ΔnagE::pTrc-nanEM | Example 3 |
| AT-032 | AT-031-02, ΔnagB promotor::Trc promoter | Example 4 |
| AT-033 | AT-032, ΔglmS promotor | Example 4 |
| AT-034 | AT-031-02, ΔglmS promotor::Trc promoter | Example 4 |

-continued

| Strain Number | Genotype Description | Note |
|---|---|---|
| AT-035 | AT-034, ΔnagB promotor | Example 4 |
| AT-036 | AT-031-02, wecB/pTrc99A | Example 5 |
| AT-037 | AT-031-02, ΔwecB promotor::Trc promoter | Example 5 |
| AT-038 | AT-033, wecB/pTrc99A | Example 6 |
| AT-039 | AT-033, ΔwecB promotor::Trc promoter | Example 6 |
| AT-040 | AT-035, wecB/pTrc99A | Example 6 |
| AT-041 | AT-035, ΔwecB promotor::Trc promoter | Example 6 |
| AT-042-01 | AT-004-02, ΔnagE::pTrc-wecB-fKanrf | Example 9 |
| AT-042-02 | AT-004-02, ΔnagE::pTrc-wecB | Example 9 |
| AT-043-01 | AT-004-02, ΔnagE::pTrc-wecBM-fKanrf | Example 9 |
| AT-043-02 | AT-004-02, ΔnagE::pTrc-wecBM | Example 9 |

Example 1

This example describes the construction of an *E. coli* mutant that blocks the metabolic pathway associated with the uptake of N-acetyl-D-glucosamine and the degradation of beneficial intermediates.

The parent strain of the production strain was AT-001 (*Escherichia coli* ATCC 27325), belonging to the *E. coli* K-12 derivative, and came from the American Type Culture Collection.

Blocking the N-acetyl-D-glucosamine uptake and degradation of intermediate metabolites by the strain can reduce the loss in the metabolic process and increase the accumulation of the target product (N-acetyl-D-glucosamine).

Construction of this mutant host strain can be achieved by completely or partially deleting the manXYZ, nanA, nagA and nagE gene sequences on its chromosomal genome to disable their functions, and thus cause the accumulation of N-acetyl-D-glucosamine.

The deletion of the gene sequence on the chromosome can be done using Red recombination technology. Red recombination is a DNA homologous recombination technique mediated by the lambda phage Red operon and the Rac phage RecE/RecT system. By this technique, it is possible to easily and rapidly perform various modifications such as insertion, knockout, and mutation in any large DNA molecules. Simply stated, the Red Recombination Technology is: the pKD46 plasmid carrying the recombinase gene is first transferred into the cells, and then the linear DNA segment for targeting is prepared by electroporation, and the positive clones are screened, finally, the resistance genes in the recombinant strain are eliminated.

The following describes the specific operation procedures:

1. Deletion of the manXYZ Gene Sequence

The mannose transporter EIIM, P/III$^{man}$ (mannose transporter EIIM, P/III$^{Man}$, ManXYZ) can be used as a second transporter protein of N-acetyl-D-glucosamine, which can transport hexoses such as N-acetyl-D-glucosamine into the cells, thus the target product excreted and accumulated outside the cells can be transported back for intracellular degradation. Deletion of the manXYZ gene sequence prevents extracellular N-acetyl-D-glucosamine from being transported back into the cell for degradation.

(1) Preparation of a Linear DNA Full-Length PCR Fragment for Red Recombination Targeting 1) PCR Amplification of fKanrf Segments The fKanrf segment, that is, the FRT-Kanr-FRT segment, refers to a FRT site base sequence for specific recognition by FLP recombinase, mounted at both ends of the kanamycin resistance gene (Kanr).

Design of Primers: forward primer (mfKanf-F) SEQ ID No: 1, and reverse primer (mfKanf-R) SEQ ID No: 2.

Template: pPic9K.

PCR reaction conditions: first step: denaturation at 94° C. for 1 min; second step: incubation at 94° C. for 30 s, at 55° C. for 30 s, at 72° C. for 40 s, and carrying out 30 cycles; third step: extension at 72° C. for 10 min.

fKanrf size: 1.28 kb. Its nucleotide sequence is SEQ ID No: 3.

The PCR product was separated by 1% agarose gel electrophoresis and purified to recover the segment.

2) PCR Amplification of Full-Length Linear DNA Segments for Red Recombination Targeting Design of a homology arm primer: according to the manXYZ sequence of SEQ ID No:4, designing a homologous arm forward primer with the manXYZ sequence deleted (manXYZKO-F) and having the sequence of SEQ ID No: 5, and reverse primer (manXYZKO-R) having the sequence of SEQ ID No: 6.

Template: Amplified FKANRF PCR segment.

PCR reaction conditions: the first step: denaturation at 94° C. for 1 min; the second step: incubation at 94° C. for 30 s, at 55° C. for 30 s, at 72° C. for 40 s, and carrying out for 30 cycles; the third Step: extension at 72° C. for 10 min.

Amplification Product: Homologous arm+fkanrf+homologous arm.

The PCR products were separated by agarose gel electrophoresis and purified and recovered to obtain 100 ng/μl linear DNA full-length PCR segment for Red recombinant targeting.

(2) Red Recombination Operation

First, the pKD46 vector was introduced into the AT-001 strain of *E. coli*. Then, a linear DNA segment for targeting was prepared by electroporation, and positive clones were selected. Finally, the resistance genes were removed.

1) Transformation of pKD46 Plasmid

The pKD46 vector is a plasmid carrying the gene for expression of the Red recombinase, which expresses the three gene segments of Exo, Bet and Gam. The three genes are placed under the arabinose promoter and can be expressed in a large amount by L-arabinose induction. In order to achieve the purpose of modifying the target gene on the chromosome by Red recombination, it is necessary to transform the pKD46 plasmid into *E. coli*.

① Preparation of Competence:

First, *Escherichia coli* ATCC 27325 stock solution stored at −20° C. was inoculated in 10 ml of LB liquid medium in a ration of 1:50-100, and shake-cultured at 37° C. and 225 rpm for 2-3 hours. The culture solution was further added to a 10 ml centrifuge tube, centrifuged at 4000 g×5 min, the supernatant was discarded, and the solution was suspended with 5 ml of 0.1M CaCl$_2$ on an ice bath of for 5 min. Finally, centrifuged at 4000 g×5 min, the supernatant was discarded, and the solution was suspended with 5 ml 0.1M CaCl$_2$ on an ice bath. It was allowed to stand at −4° C. for 12 hours and naturally settled. Preparation of 0.1M CaCl$_2$: using anhydrous CaCl$_2$ to make 1M CaCl$_2$), autoclaved with a vapor pressure of 15 lbf/in$^2$ for 20 min, and 1.5 ml of the mixture was packaged and stored at −20° C.; for use, allowed to thaw, and then diluted in a ratio of 1:10 to make 0.1M CaCl$_2$ solution.

② Plasmid transformation: 250 μl of the naturally-precipitated bacterial solution were taken, and 5 μl of pKD46 plasmid was added and cultured at −4° C. for 30 min. Then, it was heated on a 42° C. water bath for 1.5 min, and 0.7 ml of SOC medium was added, and the mixture was shaken at 30° C. for 2 hours. 0.2 ml of bacterial solution was transferred and smeared on a penicillin plate. Incubated overnight (12-16 hours) at 30° C. Monoclones were picked and cultured in 5 ml of LB liquid medium, and plasmid was extracted for identification. Positive strains were preserved for use.

2) Electrotransform the Prepared Linear DNA Segment for Targeting, and Screen for Positive Clones ① Preparation of Electrotransform Competence:

AT-001 strain of *Escherichia coli* ATCC 27325 containing pKD46 was inoculated into a test tube containing ampicillin (Amp) LB medium, shake-cultured at 250 rpm overnight, and inoculated in a ratio of 1% into LB medium containing Amp the next day, then cultured at 30° C. When $OD_{600}$ reached about 0.2, added 0.2% L-arabinose and induced at 30° C. for 35 minutes until $OD_{600}$ reached about 0.4. The solution was cooled on an ice bath, then washed once with ultrapure water, washed twice with 10% glycerol, and finally resuspended with 10% glycerol. The amount of glycerin used was to produce a final concentration of the bacterial solution concentrated by 500-1000 folds.

② Transformation by Electric Shock:

took out the 2 mm electrotransformation cup from 70% ethanol, washed twice with sterile ultrapure water, and irradiated with ultraviolet light for 30 minutes. It was pre-cooled for 30 minutes at 4° C. 90 μl of the final resuspended cells were taken and transferred to a pre-cooled centrifuge tube, and added 5 μl (more than 100 ng) of the full-length PCR segment (linear DNA) obtained in step (1), gently suction mixed with a gun, and ice bathed for 30 minutes. Electrotransformation parameters: 2500V, 200Ω, 25 μF.

③ Resuscitation and Screening Positive Clones:

1 ml of LB liquid medium was added, and cultured at 37° C. and 100 rpm for 1 hour. Then, one kanamycin (Kan) plate was coated with every 200 μl, five plates in total. The coating was even and allowed to dry. The plates were incubated at 30° C. for 24 hours. Clones grown under resistance to kanamycin were picked for PCR identification and positive clones were screened.

The obtained strain number: AT-002-01 (AT-001, ΔmanXYZ:: fKanrf).

Removal of the Resistance Gene

To facilitate subsequent work, the resistance gene in the obtained strain (positive clones) may be removed. Removal of the resistance gene may be accomplished by pCP20 plasmid. pCP20 is a plasmid with ampicillin and chloramphenicol resistance genes, and may express FLP recombinase after thermal induction, the FLP recombinase may specifically identify FRT sites. The sequence between FRT sites may be deleted by recombination, and only one FRT site is retained.

pCP20 was introduced into the above kanamycin-resistant clones, cultured at 30° C. for 8 h, then increased to 42° C. and cultured overnight, and thermally induced to express FLP recombinase; the plasmids were lost gradually. Inoculating loop was dipped with bacterial suspension and streaked the plate of antibiotics-free culture medium, grown monoclones were picked up and dotted on the kanamycin-resistant plate; those that did not grow were clones of which the kanamycin resistance gene had been removed by FLP recombination. Carried out PCR with identification primer to identify clones losing kanamycin resistance.

The obtained strain number: AT-002-02 (AT-001, ΔmanXYZ).

2. Deletion of nanA Gene Sequence

N-Acetylneuraminate lyase (NanA) can degrade N-Acetyl-D-Mannosamine (ManNAc) in microorganism to produce N-Acetyl-D-Neuraminic Acid (Neu5Ac). Deletion of the nanA gene sequence in nanKETA operon may block degradation of N-Acetyl-D-Mannosamine (ManNAc) into N-Acetyl-D-Neuraminic Acid (Neu5Ac).

(1) Preparation of Linear DNA Full-length PCR Segment for Red Recombination Targeting Design of Homologous Arm Primer: According to the nanA sequence of SEQ ID No:7 in the former segment of nanE-nanK, the homologous arm primers for deletion of nanA sequence were designed: Forward primer (nanAKO-F) SEQ ID No: 8 and reverse primer (nanAKO-R) SEQ ID No: 9.

Template: Amplification of fKanrfPCR Segment.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product: Homologous Arm+fKanrf+Homologous Arm.

The PCR product was separated by agarose gel electrophoresis, and purified and recovered to obtain 100 ng/μL linear DNA full-length PCR segment for Red recombination targeting.

(2) Red Recombination Operation

First, pKD46 carrier was introduced into the AT-002-02 strain of *Escherichia coli*. Then, the prepared linear DNA segment for targeting was electrotransformed, and positive clones were screened. Finally, the resistance genes were removed.

1) Transformation of pKD46 Plasmid

① Preparation of Competence:

First, inoculated the bacterial suspension of *Escherichia coli* AT-002-02 (AT-001, ΔmanXYZ) stored at −20° C. into 10 mL of LB broth medium in a ratio of 1:50-100, and shake-cultured at 37° C. and 225 rpm for 2-3 h. then added the culture solution to a 10-mL centrifuge tube, centrifuged at 4000 g×5 min, discarded the supernatant, and suspended with 5 mL 0.1M $CaCl_2$ on an ice bath for 5 min. Finally, centrifuged at 4000 g×5 min, discarded the supernatant, and suspended with 5 mL of 0.1M $CaCl_2$ on an ice bath. Allowed to stand at −4° C. for 12 h for natural sedimentation.

② Plasmid Transformation:

Transferred 250 μL of naturally settled bacterial solution, added 5 μL of pKD46 plasmid, and cultured at −4° C. for 30 min. Then heated on a water bath at 42° C. for 1.5 min, added 0.7 mL of SOC medium, and shook at 30° C. for 2 h. Transferred 0.2 mL of the bacterial suspension, and smeared on a penicillin plate. Cultured overnight (for 12-16 h) at 30° C. Monoclone was picked up, added 5 mL of LB broth medium and cultured, and plasmid was extracted for identification. Stored the positive strain for use.

2) Electrotransform Linear DNA Segment for Targeting, and Screen Positive Clone

① Preparation of Electrotransform Competence:

Inoculated the AT-002-02 strain of *Escherichia coli*, containing pKD46, into a test tube of LB medium containing Ampicillin (Amp), and shake-cultured at 250 rpm. On the next day, inoculated in a ratio of 1% into LB medium containing Amp, and cultured at 30° C.; when $OD_{600}$ reached about 0.2, added 0.2% L-Arabinose, and induced at 30° C. for 35 min until $OD_{600}$ reached about 0.4. Cooled on an ice bath. Washed once with ultrapure water, washed twice with 10% glycerin, and finally resuspended with 10% glycerin; the amount of glyerin used was to produce a final concentration of the bacterial soluion concentrated by 500-1000 folds.

② Transformation by Electric Shock:

Took out a 2-mm electrotransformation cup from 70% ethanol, washed twice with sterilized ultrapure water, and irradiated by UV lamp for 30 min. Precooled at 4° C. for 30 min. Transferred 90 μL of finally resuspended cells to a precooled centrifuge tube, added 5 μL (more than 100 ng) of the full-length PCR segement (linear DNA) obtained in Step (1), gently suction mixed with a gun, and maintained on an ice bath for 30 min. Electrotransformation Parameters: 2500V, 200Ω, 25 μF.

③ Resuscitate and Screen Positive Clones:

added 1 mL of LB broth medium, and cultured at 37° C. and 100 rpm for 1 h. Then smeared one kanamycin (Kan) plate with every 200 μL, 5 plates in total. Smeared evenly and allowed to dry. Cultured at 30° C. for 24 h. Picked up clones grown under kanamycin resistance, and carried out PCR identification to screen positive clones.

The obtained strain number: AT-003-01 (AT-002-02, ΔnanA::fKanrf).

(3) Removal of the Resistance Gene

Introduced pCP20 into the above kanamycin-resistant clones, cultured at 30° C. for 8 h, then increases to 42° C. and cultured overnight, and thermally induced to express FLP recombinase; the plasmids were lost gradually. Streaked the plate of antibiotics-free culture medium by an inoculating loop dipped in the bacterial suspension, picked up grown monoclones and dotted on the kanamycin-resistant plate; those that did not grow were clones of which the kanamycin resistance gene had been removed by FLP recombination. Carried out PCR with identification primer to identify clones losing kanamycin resistance.

The obtained strain number: AT-003-02 (AT-002-02, ΔnanA).

3. Deletion of nagA Gene Sequence

N-acetyl-D-glucosamine-6-phosphate deacetylase (NagA) can transform N-acetyl-D-glucosamine-6-phosphate (GlcNAc-6-P) in microorganism into D-glucosamine-6-phosphate (GlcN-6-P). Deletion of nagA gene sequence in nag operon (nagE-nagBACD) may block transformation of N-acetyl-D-glucosamine-6-phosphate (GlcNAc-6-P) into D-Glucosamine-6-phosphate (GlcN-6-P).

(1) Preparation of Linear DNA Full-length PCR Segment for Red Recombination Targeting Design of Homologous Arm Primers: From NCBI, looked up NC_000913, nagA sequence SEQ ID No: 10 for N-acetyl-D-glucosamine-6-phosphate deacetylase, *Escherichia coli* str.K-12, designed the homologous arm primers for deletion of nagA sequence: Forward primer (nagAKO-F) SEQ ID No: 11 and reverse primer (nagAKO-R) SEQ ID No: 12.

Template: Amplification of fKanrfPCR Segment.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product: Homologous Arm+fKanf+Homologous Arm.

The PCR product is separated by agarose gel electrophoresis, and purified and recovered to obtain 100 ng/μL linear DNA full-length PCR segment for targeting of Red recombination.

(2) Red Recombination Operation

First, pKD46 carrier was introduced into the AT-003-02 strain of *Escherichia coli*. Then, the prepared linear DNA segment for targeting was electrotransformed, and positive clones were screened. Finally, the resistance genes were removed.

1) Transformation of pKD46 Plasmid

① Preparation of Competence:

First, inoculateed the bacterial suspension of *Escherichia coli* AT-003-02 (AT-002-02, ΔnanA) stored at −20° C. into 10 mL of LB broth medium in a ratio of 1:50-100, and shake-cultured at 37° C. and 225 rpm for 2-3 h. then added the culture solution to a 10-mL centrifuge tube, centrifuged at 4000 g×5 min, discarded the supernatant, and suspended with 5 mL 0.1M $CaC_2$ on an ice bath for 5 min. Finally, centrifuged at 4000 g×5 min, discarded the supernatant, and suspended with 5 mL of 0.1M $CaCl_2$ on an ice bath. Allowed to stand at −4° C. for 12 h for natural edimentation.

② Plasmid Transformation:

Transferred 250 μL of naturally settled bacterial solution, add 5 μL of pKD46 plasmid, and cultured at −4° C. for 30 min. Then heated on a water bath at 42° C. for 1.5 min, added 0.7 mL of SOC medium, and shook at 30° C. for 2 h. Transferred 0.2 mL of the bacterial suspension, and smeared on a penicillin plate. Cultured overnight (for 12-16 h) at 30° C. Picked up monoclone, added 5 mL of LB broth medium and cultured, and plasmid was extracted for identification. Storeed the positive strain for use.

2) Electrotransform Linear DNA Segment for Targeting, and Screen Positive Clone

① Preparation of Electrotransform Competence:

Inoculated the AT-003-02 strain of *Escherichia coli*, containing pKD46, into a test tube of LB medium containing Ampicillin (Amp), and shake-cultured at 250 rpm, on the next day, inoculated in a ratio of 1% into LB medium containing Amp, and cultured at 30° C.; when $OD_{600}$ reached about 0.2, added 0.2% L-Arabinose, and induced at 30° C. for 35 min until $OD_{600}$ reached about 0.4. Cooled on an ice bath. Washed once with ultrapure water, washed twice with 10% glycerin, and finally resuspended with 10% glycerin; the amount of glycerin used is to produce a final concentration of the bacterial solution concentrated by 500-1000 folds.

② Transformation by Electric Shock:

Took out a 2-mm electrotransformation cup from 70% ethanol, washed twice with sterilized ultrapure water, and irradiated by UV lamp for 30 min. Precooled at 4° C. for 30 min. Transferred 90 μL of finally resuspended cells to a precooled centrifuge tube, added 5 μL (more than 100 ng) of the full-length PCR segement (linear DNA) obtained in Step (1), gently suction mixed with a gun, and maintained on an ice bath for 30 min. Electrotransformation Parameters: 2500V, 200Ω, 25 μF.

③ Resuscitate and Screen Positive Clones:

added 1 mL of LB broth medium, and cultured at 37° C. and 100 rpm for 1 h. Then smeared one kanamycin (Kan) plate with every 200 μL, 5 plates in total. Smeared evenly and allowed to dry. Cultured at 30° C. for 24 h. Picked up clones grown under kanamycin resistance, and carried out PCR identification to screen positive clones.

The obtained strain number: AT-004-01 (AT-003-02, ΔnagA::fKanrf).

(3) Removal of the Resistance Gene

Introduced pCP20 into the above kanamycin-resistant clones, cultured at 30° C. for 8 h, then increased to 42° C. and cultured overnight, and thermally induced to express FLP recombinase; the plasmids were lost gradually. Streaked the plate of antibiotics-free culture medium by an inoculating loop dipped in the bacterial suspension, picked up grown monoclones and dotted on the kanamycin-resistant plate; those that did not grow were clones of which the kanamycin resistance gene had been removed by FLP recombination. Carried out PCR with identification primer to identify clones losing kanamycin resistance.

The obtained strain number: AT-004-02 (AT-003-02, ΔnagA).

4. Deletion of nagE Gene Sequence

Deletion of the gene sequence nagE for N-acetyl-D-glucosamine specific enzyme II$^{Nag}$ (NagE) may block transport of extracellular GlcNAc into cells for degradation.

(1) Preparation of Linear DNA Full-length PCR Segment for Red Recombination Targeting Design of Homologous Arm Primers: From NCBI, looked up NC_000913, nagB promoter and nagA gene sequence SEQ ID No: 13, *Escherichia coli* str.K-12, designed the homologous arm primers for deletion of nagA sequence: Forward primer (nagEKO-F1) SEQ ID No:14 and reverse primer (nagEKO-R1) SEQ ID No:15.

Template: Amplification of fKanrfPCR Segment.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product: Homologous Arm+fKanrf+Homologous Arm.

The PCR product was separated by agarose gel electrophoresis, and purified and recovered to obtain 100 ng/L linear DNA full-length PCR segment for Red recombination targeting.

(2) Red Recombination Operation

First, pKD46 carrier was introduced into the AT-004-02 strain of *Escherichia coli*. Then, the prepared linear DNA segment for targeting was electrotransformed, and positive clones were screened. Finally, the resistance genes were removed.

1) Transformation of pKD46 Plasmid

① Preparation of Competence:

First, inoculated the bacterial suspension of *Escherichia coli* AT-004-02 (AT-003-02, ΔnagA) stored at −20° C. into 10 mL of LB broth medium in a ratio of 1:50-100, and shake-cultured at 37° C. and 225 rpm for 2-3 h. then added the culture solution to a 10-mL centrifuge tube, centrifuged at 4000 g×5 min, discarded the supernatant, and suspended with 5 mL 0.1M CaCl$_2$ on an ice bath for 5 min. Finally, centrifuged at 4000 g×5 min, discarded the supernatant, and suspended with 5 mL of 0.1M CaCl$_2$ on an ice bath. Allowed to stand at −4° C. for 12 h for natural sedimentation.

② Plasmid Transformation: Transferred 250 µL of naturally settled bacterial solution, add 5ed µL of pKD46 plasmid, and cultured at −4° C. for 30 min. Then heated on a water bath at 42° C. for 1.5 min, added 0.7 mL of SOC medium, and shook at 30° C. for 2 h. Transferred 0.2 mL of the bacterial suspension, and smeared on a penicillin plate. Cultured overnight (for 12-16 h) at 30° C. Picked up monoclones, added 5 mL of LB broth medium and cultured, and plasmid was extracted for identification. Stored the positive strain for use.

2) Electrotransform Linear DNA Segment for Targeting, and Screen Positive Clone

① Preparation of Electrotransform Competence: Inoculated the AT-004-02 strain of *Escherichia coli*, containing pKD46, into a test tube of LB medium containing Ampicillin (Amp), and shake-cultured at 250 rpm. On the next day, inoculated in a ratio of 1% into LB medium containing Amp, and cultured at 30° C.; when OD$_{600}$ reached about 0.2, added 0.2% L-Arabinose, and induced at 30° C. for 35 min until OD$_{600}$ reached about 0.4. Cooled on an ice bath. Washed once with ultrapure water, washed twice with 10% glycerin, and finally resuspended with 10% glycerin; the amount of glycerin used was to produce a final concentration of the bacterial solution concentrated by 500-1000 folds.

② Transformation by Electric Shock:

Took out a 2-mm electrotransformation cup from 70% ethanol, washed twice with sterilized ultrapure water, and irradiated by UV lamp for 30 min. Precooled at 4° C. for 30 min. Transferred 90 µL of finally resuspended cells to a precooled centrifuge tube, added 5 µL (more than 100 ng) of the full-length PCR segment (linear DNA) obtained in Step (1), gently suction mixed with a gun, and maintained on an ice bath for 30 min. Electrotransformation Parameters: 2500V, 200Ω, 25 µF.

③ Resuscitate and Screen Positive Clones: added 1 mL of LB broth medium, and cultured at 37° C. and 100 rpm for 1 h. Then smeared one kanamycin (Kan) plate with every 200 µL, 5 plates in total. Smeared evenly and allowed to dry. Cultured at 30° C. for 24 h. Picked up clones grown under kanamycin resistance, and carried out PCR identification to screen positive clones.

The obtained strain number: AT-005-01 (AT-004-02, ΔnagE::fKanrf).

(3) Removal of the Resistance Gene

Introduced pCP20 into the above kanamycin-resistant clones, cultured at 30° C. for 8 h, then increased to 42° C. and cultured overnight, and thermally induced to express FLP recombinase; the plasmids were lost gradually. Streaked the plate of antibiotics-free culture medium by an inoculating loop dipped in the bacterial suspension, picked up grown monoclones and dotted on the kanamycin-resistant plate; those that did not grow were clones of which the kanamycin resistance gene had been removed by FLP recombination. Carried out PCR with identification primer to identify clones losing kanamycin resistance.

The obtained strain number: AT-005-02 (AT-004-02, ΔnagE).

Example 2

This example describes the gene NanE cloning of N-acetyl-D-aminomannose-6-phosphate epimerase (NanE), and transformed nanE/pTrc99A plasmids in *Escherichia coli*, as well as integration of ptrc-nanE gene cassette into the chromosome of *Escherichia coli*.

1. nanE Gene Cloning, Transformation of nanE/pTrc99A plasmid in *Escherichia coli*, and its Influence on Output of N-acetyl-D-glucosamine Amplification of the gene nanE of *Escherichia coli* NanE (N-acetyl-D-aminomannose-6-phosphate epimerase), that is controlled by Trc promoter to transform the strain for overexpression of the enzyme, may strengthen the conversion of N-acetyl-D-mannosamine-6-phosphate (ManNAc-6-P) into N-acetyl-D-glucosamine-6-phosphate (GlcNAc-6-P).

1) Cloning of *Escherichia coli* nanE Gene

From NCBI, looked up U00096, to obtain the nucleotide sequence SEQ ID No: 16 of the nanE gene of *Escherichia coli*, whose amino acid sequence is SEQ ID No: 17.

Primer Design: Forward primer (nanE-F) SEQ ID No: 18 and reverse primer (nanE-R) SEQ ID No:19.

Template: AT-001 (*Escherichia coli* ATCC 27325) genome

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product Size: 690 bp.

The PCR product was separated by 1% agarose gel electrophoresis, and purified to recover the segment.

Connected the obtained PCR amplification segment with pUC57-T carrier, and carried out sequencing for identification, to obtain nanE/pUC57.

) Construction and Transformation of Plasmid in which nanE Gene is Controlled by Trc Promoter.

① Plasmid Construction:

Amplified plasmid nanE/pUC57, digested enzymatically nanE/pUC57 and carrier pTrc99A with Nco I and Hind III, respectively, separated by agarose gel electrophoresis, purified to recover nanE segment and pTrc99A segment, connected overnight with T4 DNA ligase at 16° C., and carried out identification to obtain nanE/pTrc99A plasmid.

② Preparation of Competence:

First, inoculated the bacterial suspension of AT-005-02 stored at −20° C. into 10 mL of LB broth medium in a ratio of 1:50-100, and shake-cultured at 37° C. and 225 rpm for 2-3 h. then added the culture solution to a 10-mL centrifuge tube, centrifuged at 4000 g×5 min, discarded the supernatant, and suspended with 5 mL 0.1M $CaCl_2$ on an ice bath for 5 min. Finally, centrifuged at 4000 g×5 min, discarded the supernatant, and suspended with 5 mL of 0.1M $CaCl_2$ on an ice bath. Allowed to stand at −4° C. for 12 h for natural sedimentation.

③ Plasmid Transformation:

Transferred 250 μL of naturally settled bacterial solution, added 5 μL of nanE/pTrc99A plasmid, and cultured at −4° C. for 30 min. Then heated on a water bath at 42° C. for 1.5 min, added 0.7 mL of SOC medium, and shook at 30° C. for 2 h. Transferred 0.2 mL of the bacterial suspension, and smeared on a penicillin plate. Cultured overnight (for 12-16 h) at 30° C. Picked up monoclone, added 5 mL of LB broth medium and cultured, and plasmids were extracted for identification. Storeed the positive strain for use. Obtained Recombinant Strain nanE/pTrc99A (AT-005-02)

3) Influence of nanE/pTrc99A Plasmid Transformation on the Output of N-Acetyl-D-Glucosamine Comparing the recombinant nanE/pTrc99A (AT-005-02) strain with reference strain using shake-flask fermentation trial. Transferred the monoclonal strain freshly cultured in culture medium of the LB plate, inoculated into a test tube (13×150 mm) containing 3 mL of the LB broth culture medium, and shake-cultured at 30° C. for 8 h. Components of LB Broth Medium: 5 g/L yeast powder, 10 g/L peptone, and 10 g/L NaCl. Then transferred the seed culture solution, inoculated 3% into a 250-mL shake-flask containing 50 mL of the fermentation culture solution (M9 culture solution). The initial $OD_{600}$ was about 0.5; shake-cultured at 37° C. and 225 rpm. The fermentation cycle was 72 h. At 24 h and 48 h, adjusted the pH value of the fermentation solution to pH 7.0 with 10M NaOH. According to glucose consumption in the fermentation broth, added 65% glucose solution to maintain a glucose concentration of 20 g/L. After completion of fermentation, transferred 1 mL of the fermentation broth and centrifuged. Measured the content of N-acetyl-D-glucosamine by HPLC method.

① HPLC Method to Measure the Content of N-acetyl-D-glucosamine

Buffer: Added 3.5 g of dipotassium hydrogen phosphate to 1-L volumetric flask, added water to dissolve, added 0.25 mL of 0.25 mL of ammonia water, then diluted with water and mixed well, adjusted to pH 7.5, and added water to volume.

1 Mobile Phase: Acetonitrile: Buffer (75:25).

Diluent: Acetonitrile and water (50:50).

Standard Solution: Dissolved 1.0 mg/mL USP N-acetyl-D-glucosamine

Reference Substance (RS) in the diluent.

Sample Solution: Dissolved 1.0 mg/mL N-acetyl-D-glucosamine sample in the diluent.

Liquid Phase Conditions:

Model: LC

Detector: UV 195 nm

Chromatographic Column: 4.6-mm×15-cm; 3-μm packing L8

Flow Rate: 1.5 mL/min

Column Temperature: 35° C.

Injection Volume: 10 μL

⊖ Preparation of M9 Culture Solution

First prepared 5×M9 culture medium: added into approximately 800 mL of double distilled water ($ddH_2O$) 64 g of $Na_2HPO_4 \cdot 7H_2O$, 15 g of $KH_2PO_4$, 2.5 g of NaCl, and 5.0 g of $NH_4Cl$, and after dissolution, added water to 1000 mL. Sterilized at 121° C. for 30 min. Then prepared 1M $MgSO_4$, 1M $CaCl_2$, and 20% glucose, respectively, and sterilized them separately. Then prepared M9 culture solution according to Table 1, while 1000× microelement solution was prepared according to Table 2.

TABLE 1

| 2) Components of M9 Culture Solution | |
|---|---|
| Ingredients | Amount (mL/L) |
| 5 × M9 | 200 |
| 1M $MgSO_4$ | 2 |
| 1M $CaCl_2$ | 0.1 |
| 20% Glucose | 20 |
| 1000 × Microelement Solution | 1 |
| $ddH_2O$ | to 1000 |
| pH | 6.9 |

TABLE 2

| 3) Components of 1000× Microelement Solution | |
|---|---|
| Ingredients | Amount (g/L) |
| $CoCl_2 \cdot 6H_2O$ | 0.01 |
| $CuSO_4 \cdot 5H_2O$ | 0.01 |
| $MnSO_4 \cdot H_2O$ | 0.033 |
| $FeSO_4 \cdot 7H_2O$ | 0.50 |
| $ZnSO_4 \cdot 7H_2O$ | 0.38 |
| $H_3BO_3$ | 0.01 |
| $NaMoO_4 \cdot 2H_2O$ | 0.01 |
| pH | 3 |

③ Influence of nanE/pTrc99A Plasmid Transformation on the Output of N-Acetyl-D-Glucosamine from Shake-Flask Fermentation See Table 3 for the output from shake-flask fermentation. The results show that: The output by the reference strain AT-005-02 was very low and was not detected, while the output from overexpressed recombinant nanE/pTrc99A (AT-005-02), by nanE gene controlled by Trc promoter, increased significantly.

TABLE 3

Output from Shake-flask Fermentation by the
Recombinant nanE/pTrc99A (AT-005-02)

| Strains | Output of N-acetyl-D-glucosamine (g/L) |
|---|---|
| AT-005-02 (AT-004-02, ΔnagE) (Reference) | Not detected |
| NanE/pTrc99A (AT-005-02) | 1.3 ± 0.3 |

2. Integration of pTrc-nanE Gene Cassette into the Chromosome of *Escherichia Coli*

The nagE gene site was used as integration site of pTrc-nanE gene cassette into the chromosome. To achieve integration of pTrc-nanE gene cassette into the chromosome of *Escherichia coli*, first the nanE segment containing Trc promoter pTrc-nanE was amplified, as well as the kanamycin resistance gene segment with FLP recognition site (FRT site) at its both ends: FRT-Kanr-FRT (fXanrf), and they were spliced. Then homologous arm primers for deletion of the nagE gene sequence was designed, and using the spliced segment of pTrc-nanK and fKanrf as template, amplified the linear DNA full-length segment for Red recombination targeting.

The specific operation process is provided below:

(1) PCR Amplification of pTrc-nanE segment
Template: nanE/pTrc99A.
Primer Design: Forward primer (Treff-F) SEQ ID No:20, and reverse primer (Treff-R) SEQ ID No:21.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
Produce Size: 0.86 kb.
The PCR product was separated by 1% agarose gel electrophoresis, and purified to recover the segment.

(2) fKanrf Segment Amplified by PCR
Primer Design: Forward primer (mfKanf-F) SEQ ID No:1, and reverse primer (mfKanf-R) SEQ ID No:2.
Template: pPic9K.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
fKanrf size: 1.28 kb. Its nucleotide sequence is SEQ ID No:3.
The PCR product was separated by 1% agarose gel electrophoresis, and purified to recover the segment.

(3) Amplification of fKanrf Spliced with pTrc-nanE
Primer Design: Forward primer (fKanf-F) SEQ ID No: 22, and reverse primer (fKanf-R) SEQ ID No: 23.
Template: fKanrf.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
fKanrf size from secondary amplification: 1.3 kb.
The PCR product was separated by 1% agarose gel electrophoresis, and purified to recover the segment.

(4) Preparation of Linear DNA Full-Length PCR Segment for Red Recombination Targeting
Design of Homologous Arm Primers: Design again homologous arm primers for deletion of the nagE gene sequence: Forward primer (nagEKO-F2) SEQ ID No: 24, and reverse primer (nagEKO-R2) SEQ ID No: 25.
Template: PTrc-nanE PCR segment and fKanrfPCR segment from secondary amplification mixed in the ratio of 1:1.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
Amplification Product: Homologous Arm+pTrc-nanE-fKanrf+Homologous Arm
The PCR product was separated by agarose gel electrophoresis, and purified and recovered to obtain 100 ng/μL linear DNA full-length PCR segment for Red recombination targeting.

(5) Red Recombination Operation
First, pKD46 carrier was introduced into the AT-004-02 strain of *Escherichia coli*. Then, the prepared linear DNA segment for targeting was electrotransformed, and positive clones were screened. Finally, the resistance genes were removed.

1) Transformation of pKD46 Plasmid
① Preparation of Competence:
First, inoculated the bacterial suspension of *Escherichia coli* AT-004-02 stored at −20° C. into 10 mL of LB broth medium in a ratio of 1:50-100, and shake-cultured at 37° C. and 225 rpm for 2-3 h. then added the culture solution to a 10-mL centrifuge tube, centrifuged at 4000 g×5 min, discarded the supernatant, and suspended with 5 mL 0.1M $CaC_2$ on an ice bath for 5 min. Finally, centrifuged at 4000 g×5 min, discarded the supernatant, and suspended with 5 mL of 0.1M $CaCl_2$ on an ice bath. Allowed to stand at −4° C. for 12 h for natural sedimentation.

② Plasmid Transformation:
Transferred 250 μL of naturally settled bacterial solution, added 5 μL of pKD46 plasmid, and cultured at −4° C. for 30 min. Then heated on a water bath at 42° C. for 1.5 min, added 0.7 mL of SOC medium, and shook at 30° C. for 2 h. Transferred 0.2 mL of the bacterial suspension, and smeared on a penicillin plate. Cultured overnight (for 12-16 h) at 30° C. Picked up monoclone, added 5 mL of LB broth medium and cultured, and plasmids were extracted for identification. Storeed the positive strain for use.

2) Electrotransform Linear DNA Segment for Targeting, and Screen Positive Clone
① Preparation of Electrotransform Competence: Inoculated the AT-004-02 strain of *Escherichia coli*, containing pKD46, into a test tube of LB medium containing Ampicillin (Amp), and shake-cultured at 250 rpm. On the next day, inoculated in a ratio of 1% into LB medium containing Amp, and cultured at 30° C.; when $OD_{600}$ reached about 0.2, added 0.2% L-Arabinose, and induced at 30° C. for 35 min until $OD_{600}$ reached about 0.4. Cooled on an ice bath. Washed once with ultrapure water, washed twice with 10% glycerin, and finally resuspended with 10% glycerin; the amount of glycerin used was to produce a final concentration of the bacterial solution concentrated by 500-1000 folds.

② Transformation by Electric Shock:
Took out a 2-mm electrotransformation cup from 70% ethanol, washed twice with sterilized ultrapure water, and irradiated by UV lamp for 30 min. Precooled at 4° C. for 30 min. Transferred 90 μL of finally resuspended cells to a precooled centrifuge tube, added 5 μL (more than 100 ng) of the full-length PCR segment (linear DNA) obtained in Step (4), gently suction mixed with a gun, and maintained on an ice bath for 30 min. Electrotransformation Parameters: 2500V, 200Ω, 25 μF.

③ Resuscitate and Screen Positive Clones:
added 1 mL of LB broth medium, and cultured at 37° C. and 100 rpm for 1 h. Then smeared one kanamycin (Kan)

plate with every 200 µL, 5 plates in total. Smeared evenly and allowed to dry. Cultured at 30° C. for 24 h. Picked up clones grown under kanamycin resistance, and carried out PCR identification to screen positive clones.

The obtained strain number: AT-030-01 (AT-004-02, ΔnagE::pTrc-nanE-fKanrf).

(6) Removal of the Resistance Gene

Introduced pCP20 into the above kanamycin-resistant clones, cultured at 30° C. for 8 h, then increased to 42° C. and cultured overnight, and thermally induced to express FLP recombinase; the plasmids were lost gradually. Streaked the plate of antibiotics-free culture medium by an inoculating loop dipped in the bacterial suspension, picked up grown monoclones and dotted on the kanamycin-resistant plate; those that did not grow were clones of which the kanamycin resistance gene had been removed by FLP recombination. Carried out PCR with identification primer to identify clones losing kanamycin resistance.

The obtained strain number: AT-030-02 (AT-004-02, ΔnagE::pTrc-nanE).

3) Influence of pTrc-nanE Gene Cassette Integration on the Output of N-Acetyl-D-Glucosamine Carried out a shake-flask fermentation trial with the recombinant strain AT-030-02 of which the nagE gene site in the chromosome was integrated with pTrc-nanE gene cassette, and the reference strain. Transferred the monoclonal strain freshly cultured in culture medium of the LB plate, inoculated into a test tube (13×150 mm) containing 3 mL of the LB broth culture medium, and shake-cultured at 30° C. for 8 h. Then transferred the seed culture solution, inoculated 3% into a 250-mL shake-flask containing 50 mL of the fermentation culture solution (M9 culture solution). The initial $OD_{600}$ was about 0.5; shake-cultured at 37° C. and 225 rpm. The fermentation cycle was 72 h. At 24 h and 48 h, adjusted the pH of the fermentation broth to pH 7.0 with 10M NaOH. According to glucose consumption in the fermentation broth, added 65% glucose solution to maintain a glucose concentration of 20 g/L. After completion of fermentation, transferred 1 mL of the fermentation broth and centrifuged. Measured the content of N-cetyl-D-glucosamine by HPLC method.

See Table 4 for the output from shake-flask fermentation. The results show that: The outputs by the reference strains AT-001 and AT-005-02 were very low and were not detected, while the output by the recombinant strain integrated with pTrc-nanE gene cassette increased significantly, and also increased significantly than that by the not integrated recombinant strain nanE/pTrc99A (AT-005-02).

TABLE 4

Output from Shake-flask Fermentation by the Recombinant Strain integrated with pTrc-nanE Gene Cassette

| Strains | Output of N-acetyl-D-glucosamine (g/L) |
| --- | --- |
| AT-001 (Reference) | Not detected |
| AT-005-02 (AT-004-02, Δ nagE) (Reference) | Not detected |
| nanE/pTrc99A(AT-005-02) | 1.2 ± 0.3 |
| AT-030-02 (AT-004-02, Δ nagE::pTrc-nanE) | 2.5 ± 0.5 |

Example 3

This example describes screening for a gene mutant of N-acetyl-D-aminomannose-6-phosphate epimerase (NanE); said gene encodes N-acetyl-D-aminomannose-6-phosphate epimerase (NanE) with increased enzyme activities.

To further increase synthetic quantity of N-acetyl-D-glucosamine by the production strain, screening a gene mutant encoding N-acetyl-D-aminomannose-6-phosphate epimerase (NanE) with increased enzyme activities. To achieve the purpose, error-prone PCR technology was used to amplify the cloned gene; through DNA polymerase used for amplification, amplified said gene under conditions leading to high-frequency mismatch, so as to obtain a high-frequency mutation in PCR products.

The specific operating process is provided below:

1. Amplification of the Gene nanE of N-Acetyl-D-Aminomannose-6-Phosphate Epimerasein Escherichia coli by Error-Prone PCR By means of Taq DNA polymerase without the property of 3'-5' proofreading function, controlled the frequency of random mutation under high magnesium ion concentration (8 mmol/L) and different dNTP concentrations (where, the concentration of dATP and dGTP was 1.5 mmol/L; and the concentration of dTTP and dCTP was 3.0 mmol/L), introduced random mutations into the target gene, and constructed a mutation library; the template concentration A260 value was 1000 ng/mL, the enzyme concentration was 5 U/µL, and the primer concentration was 100 µM.

Error-prone PCR reaction system (50 µL): 10×PCR reaction buffer 5 µl, dNTP (22.5 mM) 5 µL, $MgCl_2$ (2.5 mM) 5 µL, Forward primer (nanE-F, SEQ ID No:18) 1 µL, reverse primer (nanE-R, SEQ ID No: 19) 1 µL, DNA template (nanE/pUC57) 0.1 µL, Taq DNA polymerase 0.5 µL, and $ddH_2O$ 32.4 µL.

PCR procedure: Pre-degeneration at 96° C. for 4 min; degeneration at 94° C. for 1 min, annealing at 56° C. for 1 min, extension at 75° C. for 2 min, and repeated for 45 cycles; finally extended at 75° C. for 15 min, recovered PCR product (product size: 0.7 kb) by gel recovery method; transferred 5 µL of the product and tested with 1% agarose gel electrophoresis; the product was store at −20° C. for use.

2. Construction of the Gene Mutation Library of N-Acetyl-D-Aminomannose-6-Phosphate Epimerase Digested the above PCR product by two enzymes of restriction endonuclease, Nco I and Hind III, carried out a ligation reaction with pTrc99A digested by Nco I and Hind III, then transformed Escherichia coli AT-005-02 with the mixture of the ligated products to obtain a large amount of cloned transformants, and constructed a mutation library of transformed strains.

3. Screening for Mutants with High Enzyme Activities

Using the wild type NanE/pTrc99A (AT-005-02) as reference, randomly picked up 350 mutant clones from the mutation library of transformed strains, inoculated into 5 mL of LB medium containing 50 µg/mL Ampicillin (Amp), shake-cultured at 37° C. and 150 rpm for 18 h, and then centrifuged at 10000 rpm for 5 mim and collected bacterial solution. Discarded the supernatant, then resuspended at 4° C. in 1 mL of PBS solution (pH 7.5, 10 mmol/L), carried out ultrasonicate at a voltage of 300 V for 10 min (ultrasonicated for 3 s and paused for 6 s), centrifuged, transferred the supernatant as crude extract of enzyme for determination of enzyme activity.

Determination of N-acetyl-D-aminomannose-6-phosphate epimerase (NanE) Activity: Based on the amount of N-Acetyl-D-Mannosamine-6-phosphate (ManNAc-6-p) converted to N-acetyl-D-glucosamine-6-phosphate (GlcNAc-6-P), that is, using the reduced amount of N-Acetyl-D-Mannosamine-6-phosphate as test marker. Definition of Enzyme Activity Unit: Under the enzymatic reaction conditions, the enzyme amount needed to reduce equivalent to 1 μmol of N-Acetyl-D-Mannosamine-6-phosphate per minute is defined as one enzyme activity unit (IU). The specific procedure is provided as follows: isotope-labeled ManNAc-6-P was prepared as a substrate. Prepared a total volume of 225 ul of reaction solution containing ManNAc kinase (NanK) crude enzyme solution (containing 1-5 mg protein), 20 mM ATP disodium salt, 60 mM Tris-HCl, pH 8.1, 20 mM MgCl2 and 5 mM ManNAc, 50 nCi$^{[14C]}$ManNAc. Incubated at 37° C. for 30 min. The reaction was terminated by the addition of 350 ul of ethanol. The product was eluted with water and lyophilized. Next, a total volume of 26.5 ul of the reaction solution was prepared as an enzyme activity assay system containing 1 mM isotope-labeled ManNAc-6-P, 37 mM Tris-HCl, pH 8.0 and 19 mM MgCl2. After incubation at 37° C. for 30 min, the reaction was boiled for 3 min, then 0.1 volume of alkaline phosphatase buffer was added to adjust the pH and 20 units of alkaline phosphatase. After incubation at 37° C. for 1 hour, samples were taken onto dry chromatography paper and pre-soaked with 1% sodium tetraborate. The solvent system used was ethyl acetate:isopropanol:pyridine:water (50:22:14:14). The radioactive compound was separated by paper chromatography. The radioactivity was measured by a liquid scintillation counter, and the activity unit of N-acetyl-D-aminomannose-6-P epimerase was calculated based the amount of ManNAc-6-P converted to GlcNAc-6-P.

The results show that: The enzyme activity of the mutant strain with maximum activity was 72 IU/mL, and the enzyme activity of the reference control was 9.5 IU/mL. Through transforming NanE by error-prone PCR, a mutant strain with significantly increased enzyme activity was obtained. The mutant strain with maximum enzyme activity was picked up and plasmids were extracted for sequencing. The results showed that: The gene sequence of the mutant of N-acetyl-D-aminomannose-6-P epimerase is shown as SEQ ID No: 26, and the corresponding amino acid is shown as SEQ ID No: 27. By sequence alignment with the gene sequence of wild type N-acetyl-D-aminomannose-6-P epimerase, 3 base point mutations occurred in total: 198C/T, 397T/C, and 559T/C; and caused two amino acid missense mutation, the mutation points are: C133R (the 133th cysteine to arginine), Y187H (the 187th tyrosine to histidine). The mutant gene was named nanEM.

4. Integration of pTrc-nanE Gene Cassette into the nagE Gene Site in the Chromosome of *Escherichia Coli*

The nagE gene site was used as integration site of pTrc-nanEM gene cassette into the chromosome. To achieve integration of pTrc-nanEM gene cassette into the chromosome of *Escherichia coli*, first the nanEM segment containing Trc promoter pTrc-nanEM was amplified, as well as the kanamycin resistance gene segment with FLP recognition site (FRT site) at its both ends: FRT-Kanr-FRT (fXanrf), and they were spliced. Then homologous arm primers were designed for deletion of the nagE gene sequence, and using the spliced segment of pTrc-nanEM and fKanrf as template, amplified the linear DNA full-length segment for Red recombination targeting.

The specific operating process is provided below:

(1) PCR Amplification of pTrc-nanEM Segment
Template: nanEM/pTrc99A.
Primer Design: Forward primer (Treff-F) SEQ ID No: 20, and reverse primer (Treff-R) SEQ ID No: 21.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Produce Size: 0.86 kb.
The PCR product was separated by 1% agarose gel electrophoresis, and purified to recover the segment.

(2) fKanrf Segment Amplified by PCR
Primer Design: Forward primer (mfKanf-F) SEQ ID No:1, and reverse primer (mfKanf-R) SEQ ID No: 2.
Template: pPic9K.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
fKanrf size: 1.28 kb. Its nucleotide sequence is SEQ ID No: 3.
The PCR product was separated by 1% agarose gel electrophoresis, and purified to recover the segment.

(3) Amplification of fKanrf Spliced with pTrc-nanEM
Primer Design: Forward primer (fKanf-F) SEQ ID No: 22, and reverse primer (fKanf-R) SEQ ID No: 23.
Template: fKanrf.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
fKanrf size from secondary amplification: 1.3 kb.
The PCR product was separated by 1% agarose gel electrophoresis, and purified to recover the segment.

(4) Preparation of Linear DNA Full-Length PCR Segment for Red Recombination Targeting
Design of Homologous Arm Primers: Designed again homologous arm primers for deletion of the nagE gene sequence: Forward primer (nagEKO-F2) SEQ ID No: 24, and reverse primer (nagEKO-R2) SEQ ID No: 25.
Template: pTrc-nanEM PCR segment and fKanrf PCR segment from secondary amplification were mixed in the ratio of 1:1.
PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.
Amplification Product: Homologous Arm+pTrc-nanEM-fKanrf+Homologous Arm
The PCR product was separated by agarose gel electrophoresis, and purified and recovered to obtain 100 ng/μL linear DNA full-length PCR segment for Red recombination targeting.

(5) Red Recombination Operation
First, pKD46 carrier was introduced into the AT-004-02 strain of *Escherichia coli*. Then, the prepared linear DNA segment for targeting was electrotransformed, and positive clones were screened. Finally, the resistance genes were removed.

1) Transformation of pKD46 Plasmid
① Preparation of Competence:
First, inoculated the bacterial suspension of *Escherichia coli* AT-004-02 stored at −20° C. into 10 mL of LB broth medium in a ratio of 1:50-100, and shake-cultured at 37° C. and 225 rpm for 2-3 h. Then added the culture solution to a 10 mL centrifuge tube, centrifuged at 4000 g×5 min, discarded the supernatant, and suspended with 5 mL 0.1M CaCl$_2$ on an ice bath for 5 min. Finally, centrifuged at 4000 g×5 min, discarded the supernatant, and suspended with 5 mL of 0.1M CaC$_2$ on an ice bath. Allowed to stand at −4° C. for 12 h for natural sedimentation.
② Plasmid Transformation:
Transferred 250 μL of naturally settled bacterial solution, added 5 μL of pKD46 plasmid, and cultured at −4° C. for 30 min. Then heated on a water bath at 42° C. for 1.5 min, added 0.7 mL of SOC medium, and shook at 30° C. for 2 h. Transferred 0.2 mL of the bacterial suspension, and smeared on a penicillin plate. Cultured overnight (for 12-16 h) at 30° C. Picked up monoclone, added 5 mL of LB broth medium and cultured, and plasmids were extracted for identification. Stored the positive strain for use.

2) Electrotransform Linear DNA Segment for Targeting, and Screen Positive Clone

① Preparation of Electrotransform Competence:

Inoculated the AT-004-02 strain of *Escherichia coli*, containing pKD46, into a test tube of LB medium containing Ampicillin (Amp), and shake-cultured at 250 rpm, on the next day, inoculated in a ratio of 1% into LB medium containing Amp, and cultured at 30° C.; when $OD_{600}$ reached about 0.2, added 0.2% L-Arabinose, and induced at 30° C. for 35 min until $OD_{600}$ reached about 0.4. Cooled on an ice bath. Washed once with ultrapure water, washed twice with 10% glycerin, and finally resuspended with 10% glycerin; the amount of glycerin used was to produce a final concentration of the bacterial solution concentrated by 500-1000 folds.

② Transformation by Electric Shock:

Took out a 2-mm electrotransformation cup from 70% ethanol, washed twice with sterilized ultrapure water, and irradiated by UV lamp for 30 min. Precooled at 4° C. for 30 min. Transferred 90 μL of finally resuspended cells to a precooled centrifuge tube, added 5 μL (more than 100 ng) of the full-length PCR segment (linear DNA) obtained in Step (4), gently suction mixed with a gun, and maintained on an ice bath for 30 min. Electrotransformation Parameters: 2500V, 200Ω, 25 μF.

③ Resuscitate and screen positive clones: added 1 mL of LB broth medium, and cultured at 37° C. and 100 rpm for 1 h. Then smeared one kanamycin (Kan) plate with every 200 μL, 5 plates in total. Smeared evenly and allowed to dry. Cultured at 30° C. for 24 h. Picked up clones grown under kanamycin resistance, and carried out PCR identification to screen positive clones.

The obtained strain number: AT-031-01 (AT-004-02, ΔnagE::pTrc-nanEM-fKanrf).

(6) Removal of the Resistance Gene

Introduced pCP20 into the above kanamycin-resistant clones, cultured at 30° C. for 8 h, then increased to 42° C. and cultured overnight, and thermally induced to express FLP recombinase; the plasmids were lost gradually. Streaked the plate of antibiotics-free culture medium by an inoculating loop dipped in the bacterial suspension, picked up grown monoclones and dotted on the kanamycin-resistant plate; those that did not grow were clones of which the kanamycin resistance gene had been removed by FLP recombination. Carried out PCR with identification primer to identify clones that had lost kanamycin resistance.

The obtained strain number: AT-031-02 (AT-004-02, ΔnagE::pTrc-nanEM).

5. Influence of pTrc-nanEM Gene Cassette Integration on the Output of N-Acetyl-D-Glucosamine Carrying out a shake-flask fermentation trial comparing the recombinant strain AT-031-02 of which the nagE gene site in the chromosome was integrated with pTrc-nanEM gene cassette, with the reference strain. Transferred the monoclonal strain freshly cultured in culture medium of the LB plate, inoculated into a test tube (13×150 mm) containing 3 mL of the LB broth culture medium, and shake-cultured at 30° C. for 8 h. Then transferred the seed culture solution, inoculated 3% into a 250-mL shake-flask containing 50 mL of the fermentation culture solution (M9 culture solution). The initial $OD_{600}$ was about 0.5; shake-cultured at 37° C. and 225 rpm. The fermentation cycle was 72 h. At 24 h and 48 h, adjusted the pH value to pH 7.0 with 10M NaOH. According to glucose consumption in the fermentation broth, added 65% glucose solution to maintain a glucose concentration of 20 g/L. After completion of fermentation, transferred 1 mL of the fermentation broth and centrifuged. Measured the content of N-acetyl-D-glucosamine by HPLC method.

See Table 5 for the output from shake-flask fermentation. The results show that: The output by the reference strain AT-005-02 was very low and was not detected, while the output by the recombinant strain AT-031-02 integrated with pTrc-nanEM gene cassette increased significantly, and also increased significantly than that by the reference strain (AT-030-02) without mutation.

TABLE 5

Output from Shake-flask Fermentation by the Recombinant Strain integrated with pTrc-nanEM Gene Cassette

| Strains | Output of N-acetyl-D-glucosamine (g/L) |
|---|---|
| AT-005-02 (AT-004-02, ΔnagE) (Reference) | Not detected |
| AT-030-02 (AT-004-02, ΔnagE::pTrc-nanE) | 2.6 ± 0.5 |
| AT-031-02 (AT-004-02, ΔnagE::pTrc-nanEM) | 5.9 ± 0.8 |

The above results show that: The output of N-acetyl-D-glucosamine may be increased significantly by overexpression of N-acetyl-mannosamine-6-phosphate epimerase; moreover, the output of N-acetyl-D-glucosamine may also be greatly increased by the mutant screened by error-prone PCR technology, due to the increased enzyme activities of the obtained mutant of the enzyme.

Example 4

This example describes *Escherichia coli* strains integrated with pTrc-nanEM cassette, and wherein the effect on N-acetyl-D-glucosamine production yield of replacing and/or removing the endogenous natural promoter of the glucosamine-6-phosphate synthase (GlmS) gene glmS and/or D-Glucosamine-6-phosphate deaminase (NagB) gene nagB 1. Replacing the endogenous natural promoter of nagB gene with the Trc promoter, and further deleting the endogenous natural promoter of glmS gene, and the effect on N-acetyl-D-glucosamine production yield by *Escherichia coli* strains integrated with pTrc-NanEM gene cassette.

(1) The natural endogenous promoter of the nagB gene was replaced by Trc promoter The gene promoter of D-Glucosamine-6-Phosphate Deaminase (NagB) is nag regulon (nagE-nagBACD) was replaced by Trc promoter. The reaction catalyzed by D-Glucosamine-6-phosphate Deaminase (NagB) is reversible; overexpression of nagB may accelerate the forward catalytic reaction by NagB, to achieve the purpose of increasing D-Glucosamine-6-Phosphate (GlcN-6-P).

First, amplified Trc promoter segment and fKanrf segment, and spliced them together. Then designed homologous arm primers, and amplified linear DNA full-length segment for Red recombination targeting.

1. Amplifying the Trc Promoter Sequence

Based on published information, obtained Trc promoter sequence: SEQ ID No: 28.

Primers design: forward primer (KanTrcRed-F) SEQ ID No: 29, reverse primer (KanTrcRed-R) SEQ ID No: 30.

Template: pTrc99A

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

Product size: 166 bp.

The PCR product was separated by 1% agarose gel electrophoresis and purified to recover segment.

2. Amplifying the Kanamycin Resistance Gene with FLP Recombinase Recognition Site (FRT Site) on Both Sides: fKanrf Primers design: forward primer (mfKanf-F) SEQ ID No: 1, reverse primer (mfKanf-R) SEQ ID No: 2.

Template: pPic9K.

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

fKanrf size: 1.28 kb. Its nucleotide sequence is SEQ ID No: 3.

The PCR product was separated by 1% agarose gel electrophoresis and purified to recover segment.

3. Amplifying fKanrf Docked with the Trc Promoter

Primers design: forward primer (fKanfRed-F1) SEQ ID No: 31, reverse primer (fKanfRed-R1) SEQ ID No: 32.

Template: fKanrf.

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

The size of the second amplified fKanrf: 1.3 kb.

The PCR product was separated by 1% agarose gel electrophoresis and purified to recover segment.

4. Preparation of a Linear DNA Full-Length PCR Fragment for Red Recombinant Targeting Homology arm primers design: According to NCBI, found NC_000913, *Escherichia coli* str. K-12 nagB promoter sequence and nagE gene sequence SEQ ID No: 13, designed homology arm primer for deletion of nagB promoter gene sequence: forward primer (nagBKO-F1) SEQ ID No: 33, reverse primer (nagBKO-R1) SEQ ID No: 34.

Template: mixed Trc promoter PCR fragment and secondary amplified fKanrfPCR fragment at a ratio of 1:1.

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

Amplification product: homology arm+fKanrf+Trc promoter+homology arm.

The PCR product was separated by agarose gel electrophoresis, purified and recovered to obtain a 100 ng/μl linear DNA full-length PCR fragment for Red recombinant targeting.

5, Red Recombination Operation

First, the pKD46 vector was transferred into the *E. coli* AT-031-02 strain. Then, a linear DNA fragment for targeting was prepared by electrotransformation, and positive clones were selected. Finally, the resistance genes were eliminated.

The obtained strain number: AT-032 (AT-031-02, ΔnagB promotor::Trc promoter).

(2) Deletion of the glmS Gene Endogenous Natural Promoter

The Glucosamine-6-phosphate synthase (glmS) gene promoter sequence was deleted. Glucosamine-6-phosphate synthase (GlmS), also known as L-glutamine-6-phosphate aminotransferase (L-glutamine; D-fructose-6-phosphate aminotransferase), catalyzes the amination of glucose-6-phosphate (Glc-6)-P) to D-glucosamine-6-phosphate (GlcN-6-P), but it has serious product inhibition problems. With the deletion of its promoter sequence, expression of the enzyme is lost, and GlcN-6-P product inhibition is eliminated.

First, the fKanrf fragment was amplified, and then the homology arm primer was designed to amplify the full-length linear DNA fragment of Red recombination targeting.

1) Amplification of the kanamycin resistance gene with FLP recombinase recognition site (FRT site) on both sides: fKanrf Primers design: forward primer (mfKanf-F) SEQ ID No:1, reverse primer (mfKanf-R) SEQ ID No:2.

Template: pPic9K.

PCR reaction conditions: first step: denaturation at 94° C. for 1 min; second step: incubation at 94° C. for 30 s, 55° C. for 30 s, 72° C. for 40 s, carrying out 30 cycles; third step: extension at 72° C. for 10 min.

fKanrf size: 1.28 kb. Its nucleotide sequence is SEQ ID No: 3.

The PCR product was separated by 1% agarose gel electrophoresis and purified to recover segment.

2) Preparation of a linear DNA full-length PCR fragment for Red recombination targeting Design of the homology arm primer: According to NCBI, found the NC_000913, *Escherichia coli* str. K-12 L-glutamine-6-phosphate fructose aminotransferase (GlmS) gene promoter sequence SEQ ID No: 35, designed homology arm primer for deletion of glmS gene promoter sequence: forward primer (Proglms KO-F) SEQ ID No: 36, reverse primer (Proglms KO-R) SEQ ID No: 37.

Template: fKanrfPCR fragment.

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

Amplification product: homology arm+fKanf+homology arm.

The PCR product was separated by agarose gel electrophoresis, purified and recovered to obtain 100 ng/μl linear DNA full-length PCR fragment for Red recombination targeting.

3) Red Recombination Operation

First, the pKD46 vector was transferred into *E. coli* AT-032 strain. Then, a linear DNA fragment for targeting was prepared by electrotransformation, and positive clones were selected. Finally, the resistance gene was eliminated.

The obtained strain number: AT-033 (AT-032, ΔglmS promotor).

(3) Effect of Replacing nagB Promoter with a Higher Expression Level Promoter and Further Deleting of glmS Promoter on N-Acetyl-D-Glucosamine Production.

For the strains in which the pTrc-nanEM cassette was integrated, the nagB promoter was replaced with a promoter of a higher expression level, and the glmS promoter was further deleted in the recombinant strain. The strains were subjected to a shake flask fermentation test. The monoclonal strain on the freshly cultured LB plate medium was inoculated into a 3 ml LB liquid medium test tube (13×150 mm), and shake-cultured at 30° C. at 225 rpm for about 8 hours. Then, the seed culture solution was taken, and 3% was inoculated into a 250 ml shake flask containing 50 ml of the fermentation broth (M9 medium). The initial $OD_{600}$ was about 0.5, shake-cultured at 225 rpm at 37° C., and the fermentation cycle was 72 hours. At 24 hours and 48 hours, the pH of the fermentation broth was adjusted to 7.0 with 10 M NaOH. According to the sugar consumption of the fermentation broth, 65% glucose solution was added in portions to maintain the glucose concentration at 20 g/L. At the end of the fermentation, 1 ml of the fermentation broth was taken and centrifuged. The N-acetyl-D-glucosamine content was determined by HPLC.

The yield of shake flask fermentation is shown in Table 6. The results showed that N-acetyl-D-glucosamine yield of the recombinant strain that replaced the nagB promoter with the Trc promoter increased significantly, and after further deleting glmS promoter, the yield of N-acetyl-D-glucosamine greatly improved.

TABLE 6

Output from Shake-flask Fermentation by the Recombinant Strain with replacement of nagB promoter and further removal of glmS promoter

| Strains | Output of N-acetyl-D-glucosamine (g/L) |
|---|---|
| AT-031-02 (reference) | 6.0 ± 0.9 |
| AT-032 (AT-031-02, ΔnagB promotor::Trc promoter) | 9.3 ± 0.9 |
| AT-033 (AT-032, ΔglmS promotor) | 12.0 ± 1.1 |

Replacing the endogenous natural promoter of glmS gene with the Trc promoter, and further deleting the endogenous natural promoter of nagB gene, and the effect on N-acetyl-D-glucosamine production yield by *Escherichia coli* strains integrated with pTrc-NanEM gene cassette.

(1) Replacing the glmS Gene Endogenous Natural Promoter with the Trc Promoter

The L-glutamine-6-phosphate aminotransferase (L-glutamine: D-fructose-6-phosphate aminotransferase) gene promoter sequence was replaced with a Trc promoter sequence. L-Glutamine-6-phosphate fructose aminotransferase, also known as Glucosamine-6-phosphate synthase (GlmS); its promoter sequence was replaced with the Trc promoter sequence and led to overexpression of gimS, and accelerated GlmS catalyzing function, and achieved the goal of increasing D-glucosamine-6-phosphate (GlcN-6-P).

First, the Trc promoter sequence fragment and the fKanrf fragment were amplified and spliced. Then, a homology arm primer was designed to amplify a full-length linear DNA fragment for Red recombination targeting.

1) Amplification of Full-Length PCR Fragments of Linear DNA for Red Recombination Targeting Homology arm primer design: according to glmS gene promoter sequence of SEQ ID No: 35, designed Trc promoter homologous arm primer: forward primer (Proglmsp-Trc-F) SEQ ID No: 38, reverse primer (ProglmspTrc-R), SEQ ID No: 39.

Template: Trc promoter PCR fragment and secondary amplified fKanrfPCR fragment were mixed at a ratio of 1:1.

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

Amplification product: homology arm+fKanrf+Trc promoter+homology arm.

The PCR product was separated by agarose gel electrophoresis, purified and recovered to obtain a 100 ng/μl linear DNA full-length PCR fragment for Red recombination targeting.

2) Red Recombination Operation

First, the pKD46 vector was transferred into the *E. coli* AT-031-02 strain. Then, a linear DNA fragment for targeting was prepared by electrotransformation, and positive clones were selected. Finally, the resistance gene was eliminated.

The obtained strain number: AT-034 (AT-031-02, ΔglmS promotor::Trc promoter).

(2) Deletion of the NagB Gene Endogenous Natural Promoter

Deletion of the D-glucosamine-6-phosphate deaminase (NagB) gene promoter sequence in nag regulon (nagE-nagBACD) caused the loss of function of nagB, and eliminated NagB reverse catalysis, and reduced the production of GlcN-6-P to Glc-6-P.

First, the fKanrf fragment was amplified, and then the homology arm primer was designed to prepare a full-length linear DNA fragment for Red recombination targeting.

1) Preparation of a Linear DNA Full-Length PCR Fragment for Red Recombination Targeting Homology arm primer design: according to the nagB promoter and nagE gene sequence SEQ ID NO: 13, desgiend the homology arm primer for deletion of nagB promoter gene sequence: forward primer (NagBKO-F2) SEQ ID No: 40, reverse primer (NagBKO-R2) SEQ ID No: 41.

Template: fKanrfPCR Fragment

PCR reaction conditions: first step: denaturation at 94° C. for 1 min; second step: incubation at 94° C. for 30 s, at 55° C. for 30 s, at 72° C. for 40 s, carrying out 30 cycles; third step: extension at 72° C. for 10 min.

Amplification product: homology arm+fKanrf+homology arm.

The PCR product was separated by agarose gel electrophoresis, purified and recovered to obtain a 100 ng/μl linear DNA full-length PCR fragment for Red recombination targeting.

2) Red Recombination Operation

First, the pKD46 vector was transferred into *E. coli* AT-034 strain. Then, a linear DNA fragment for targeting was prepared by electrotransformation, and positive clones were selected. Finally, the resistance gene was eliminated.

The obtained strain number: AT-035 (AT-034, ΔnagB promotor).

(3) The Effect of Replacing the glmS Promoter with a Promoter with a Higher Expression Level and Further Deleting the nagB Promoter on the Production of N-Acetyl-Glucosamine For the strains in which the pTrc-nanEM cassette was integrated, the glmS promoter was replaced with a promoter of a higher expression level, and the recombinant strains in which the nagB promoter was further deleted were subjected to a shake flask fermentation test. The monoclonal strain on the freshly cultured LB plate medium was inoculated into a 3 ml LB liquid medium test tube (13×150 mm), and shake-cultured at 30° C. at 225 rpm for about 8 hours. Then, the seed culture solution was taken, and 3% was inoculated into a 250 ml shake flask containing 50 ml of the fermentation broth (M9 medium). The initial $OD_{600}$ was about 0.5, shake-cultured at 225 rpm at 37° C., and the fermentation cycle was 72 hours. At 24 hours and 48 hours, the pH of the fermentation broth was adjusted to 7.0 with 10 M NaOH. According to the sugar consumption of the fermentation broth, 65% glucose solution was added in portions to maintain the glucose concentration at 20 g/L. At the end of the fermentation, 1 ml of the fermentation broth was taken and centrifuged. The N-acetyl-D-glucosamine content was determined by HPLC method.

The yield of shake flask fermentation is shown in Table 7. The results showed that the recombinant strain that replaced the glmS promoter with the Trc promoter had no obvious effect on the increase of N-acetyl-D-glucosamine production, but there is a significant improvement in N-acetyl-D-glucosamine production when simultaneously deleting the nagB promoter.

TABLE 7

Output from Shake-flask Fermentation by the Recombinant Strain with replacement of glmS promoter and further removal of nagB promoter

| Strains | Output of N-acetyl-D-glucosamine (g/L) |
|---|---|
| AT-031-02 (Reference) | 5.9 ± 1.0 |
| AT-034 (AT-031-02, ΔglmS promotor::Trc promoter) | 6.2 ± 1.1 |
| AT-035 (AT-034, ΔnagB promotor) | 9.9 ± 1.0 |

Example 5

This example describes *Escherichia coli* strains integrated with pTrc-nanEM gene cassette, and overexpression the gene wecB of UDP—N-Acetyl-D-Glucosamine-2-Epimerase, as well as its influence on the output of N-Acetyl-D-Glucosamine.

The gene wecB of UDP—N-AcetylGlucosamine-2-Epimerase (WecB) was controlled by Trc promoter to transform strains, or the natural endogenous promoter of the wecB gene was replaced by Trc promoter for overexpression of the enzyme, to strengthen production of ManNAc (N-Acetyl-D-mannosamine) from UDP-GlcNAc (UDP—N-Acetyl Glucosamine).

1. Transformation of *Escherichia Coli* Strains Integrated with pTrc-NanEM Gene Cassette by wecB/pTrc99A (1) Amplifying the wecB Gene of *Escherichia coli* and Inserting pTrc99A According to NCBI, looked up the nucleotide sequence SEQ ID No: 42 of the wecB gene of *Escherichia coli*, and its amino acid sequence is SEQ ID No43.

Primer Design: Forward primer (TrcwecB-F) SEQ ID No: 44, and reverse primer (TrcwecB-R) SEQ ID No:45.

Template: AT-001 (*Escherichia coli* ATCC 27325) Genome.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product Size: 1.13 kb.

The PCR product was separated by 1% agarose gel electrophoresis, and purified to recover the segment.

Digested enzymatically the obtained PCR amplification segment and carrier pTrc99A with Nco I and Hind III, separated by agarose gel electrophoresis, purified to recover wecB segment and pTrc99A segment, connected with T4 DNA ligase at 16° C. overnight, and identified to obtain wecB/pTrc99A plasmid.

(2) Transformation of *Escherichia Coli* Strains Integrated with pTrc-NanEM Gene Cassette by wecB/pTrc99A (1) Preparation of Competence:

First, inoculated the bacterial suspension of AT-031-02 stored at −20° C. into 10 mL of LB broth medium in a ratio of 1:50-100, and shake-cultured at 37° C. and 225 rpm for 2-3 h. Then added the culture solution to a 10-mL centrifuge tube, centrifuged at 4000 g×5 min, discarded the supernatant, and suspended with 5 mL 0.1M CaCl$_2$ on an ice bath for 5 min. Finally, centrifuged at 4000 g×5 min, discarded the supernatant, and suspended with 5 mL of 0.1M CaCl$_2$ on an ice bath. Allowed to stand at −4° C. for 12 h for natural sedimentation.

(2) Plasmid Transformation:

Took 250 μL of naturally settled bacterial solution, added 5 μL of wecB/pTrc99A plasmid, and cultured at −4° C. for 30 min. Then heated on a water bath at 42° C. for 1.5 min, added 0.7 mL of SOC medium, and shook at 30° C. for 2 h. Took 0.2 mL of the bacterial suspension, and smeared on a penicillin plate. Cultured overnight (for 12-16 h) at 30° C. Picked up monoclone, added 5 mL of LB broth medium and cultured, and plasmids were extracted for identification. Positive clones were stored for use.

No of the obtained strain: AT-036 (AT-031-02, wecB/pTrc99A).

2. The Natural Endogenous Promoter of the wecB Gene of *Escherichia coli* Strains Integrated with pTrc-nanEM Cassette was Replaced with Trc Promoter First, amplified Trc promoter sequence segment and fKanrf segment, and spliced them together. Then designed homologous primers, and amplified linear DNA full-length segment for Red recombination targeting.

(1) Preparation of Linear DNA Full-Length PCR Segment for Red Recombination Targeting Design of Homologous Arm Primers: According to NCBI, looked up the nucleotide sequence SEQ ID No: 46 of the gene promoter of *Escherichia coli* UDP—N-AcetylGlucosamine-2-Epimerase (wecB), designed homologous arm primers with the promoter replaced by Trc promoter: Forward primer (ProwecBpTrc-F) SEQ ID No: 47, and reverse primer (Pro wecBpTrc-R) SEQ ID No:48.

Template: Mixed Trc promoter PCR segment and fKanrf PCR segment from secondary amplification at a ratio of 1:1.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product: Homologous Arm+fKanrf+Trc Promoter+Homologous Arm.

The PCR product was separated by agarose gel electrophoresis, and purified and recovered to obtain 100 ng/μL linear DNA full-length PCR segment for Red recombination targeting.

(2) Red Recombination Operation

First, pKD46 carrier was introduced into the AT-007-02 strain of *Escherichia coli*. Then, the prepared linear DNA segment for targeting was electrotransformed, and positive clones were screened. Finally, the resistance gene was removed.

No of the obtained strain: AT-037 (AT-031-02, ΔwecB promotor::Trc promoter).

3. The Effect of Recombinant Strain Integrated with pTrc-nanEM Gene Cassette, Strains Transformed with wecB/pTrc99A Plasmid, and Strains Having wecB Promoter Replaced by Trc Promoter on the Output of N-Acetyl-D-Glucosamine.

Carrying out a shake-flask fermentation trial with the strain integrated with pTrc-nanEM gene cassette, and the recombinant strain produced for overexpression of wecB (including the strain with transformed wecB/pTrc99A and the strain with wecB promoter replaced by Trc promoter). Transferred the monoclonal strain freshly cultivated in culture medium of the LB plate, inoculated into a test tube (13×150 mm) containing 3 mL of the LB broth culture medium, and shake-cultured at 30° C. for 8 h. Then transferred the seed culture solution, inoculated 3% into a 250-mL shake-flask containing 50 mL of M9 culture solution. The initial OD$_{600}$ was about 0.5; shake-cultured at 37° C. and 225 rpm. The fermentation cycle was 72 h. At 24 h and 48 h, adjusted the pH value to pH 7.0 with 10M NaOH. According to glucose consumption in the fermentation broth, added 65% glucose solution in portions to maintain a glucose concentration of 20 g/L. After completion of fermentation, transferred 1 mL of the fermentation broth and centrifuged. Measured the content of N-Acetyl-D-Glucosamine by HPLC method.

See Table 8 for the output from shake-flask fermentation. The results show that: Compared with the reference strain AT-031-02, the output of N-Acetyl-D-Glucosamine increased significantly in recombinant strain with transformed wecB/pTrc99A, and increased more greatly in recombinant strain with wecB promoter replaced by Trc promoter.

TABLE 8

Output from Shake-flask Fermentation by Recombinant Strains with Transformed wecB/pTrc99A Plasmid or with wecB promoter replaced by Trc Promoter

| Strains | Output of N-Acetyl-D-Glucosamine (g/L) |
|---|---|
| AT-031-02 (Reference) | 6.0 ± 1.0 |
| AT-036 (AT-031-02, wecB/pTrc99A) | 10.3 ± 1.1 |
| AT-037 (AT-031-02, ΔwecB promotor::Trc promoter) | 13.2 ± 1.1 |

Example 6

This example describes influences of the *Escherichia coli* strains integrated with pTrc-nanEM gene cassette on the output of N-Acetyl-D-Glucosamine, of which the natural endogenous promoter of the glmS gene and nagB gene was replaced and/or deleted, transformed wecB/pTrc99A plasmid or replaced the natural endogenous promoter of the wecB gene by Trc promoter 1. *Escherichia coli* strains integrated with pTrc-nanKM cassette were used to transform wecB/pTrc99A plasmid, of which the natural endogenous promoter of the nagB gene was replaced by Trc promoter, and meanwhile the natural endogenous promoter of the glmS gene was deleted Preparation of competence: Transformed wecB/pTrc99A plasmid with CaCl$_2$ into *Escherichia coli* strain AT-033 integrated with pTrc-NanEM gene cassette, of which the natural endogenous promoter of the nagB gene was replaced by Trc promoter and meanwhile the natural endogenous promoter of the glmS gene was deleted; monoclones were picked up and cultured, and plasmids were extracted to identify positive clones.

No of the obtained strain: AT-038 (AT-033, wecB/pTrc99A).

2. In *Escherichia coli* strains integrated with pTrc-nanEM cassette, of which the natural endogenous promoter of the nagB gene was replaced by Trc promoter and meanwhile the natural endogenous promoter of the glmS gene was deleted, the natural endogenous promoter of the wecB gene was replaced by Trc promoter First, pKD46 carrier was introduced into the AT-033 strain of *Escherichia coli*. Then, the prepared linear DNA segment for targeting was electrotransformed, and positive clones were screened. Finally, the resistance gene was removed.

No of the obtained strain: AT-039(AT-033, ΔwecB promotor::Trc promoter).

3. *Escherichia coli* strains integrated with pTrc-nanEM cassette were used to transform wecB/pTrc99A plasmid, of which the natural endogenous promoter of the glmS gene was replaced by Trc promoter, and meanwhile the natural endogenous promoter of the nagB gene was deleted Preparation of competence: Transformed wecB/pTrc99A plasmid with CaCl$_2$ into *Escherichia coli* strain AT-035 integrated with pTrc-nanEM gene cassette, of which the natural endogenous promoter of the glmS gene was replaced by Trc promoter and meanwhile the natural endogenous promoter of the nagB gene was deleted, monoclones were picked up and cultured, and plasmids were extracted to identify positive clones.

No of the obtained strain: AT-040 (AT-035, wecB/pTrc99A).

4. In *Escherichia coli* strains integrated with pTrc-nanEM cassette, of which the natural endogenous promoter of the glmS gene was replaced by Trc promoter and meanwhile the natural endogenous promoter of the nagB gene was deleted, the natural endogenous promoter of the wecB gene was replaced by Trc promoter First, pKD46 carrier was introduced into the AT-035 strain of *Escherichia coli*. Then, the prepared linear DNA segment for targeting was electrotransformed, and positive clones were screened. Finally, the resistance gene was removed.

No of the obtained strain: AT-041 (AT-035, ΔwecB promotor::Trc promoter).

5. Influences of the *Escherichia coli* strains integrated with pTrc-nanEM gene cassette on the output of N-Acetyl-D-Glucosamine, of which the natural endogenous promoter of the nagB gene and glmS gene was replaced and/or deleted to transform wecB/pTrc99A plasmid, and the natural endogenous promoter of the wecB gene was replaced by Trc promoter Carrying out a shake-flask fermentation trial with the recombinant strains with different genotypes, obtained from the strains integrated with pTrc-nanEM gene cassette, of which the natural endogenous promoter of the glmS and nagB genes were replaced and/or deleted to transform wecB/pTrc99A plasmid, or the natural endogenous promoter of the wecB gene was replaced by Trc promoter. Transferred the monoclonal strain freshly cultiured in culture medium of the LB plate, inoculated into a test tube (13×150 mm) containing 3 mL of the LB broth culture medium, and shake-cultured at 30° C. for 8 h. Then transferred the seed culture solution, inoculate 3% into a 250-mL shake-flask containing 50 mL of the fermentation culture solution (M9 culture solution). The initial OD$_{600}$ was about 0.5; shake-cultured at 37° C. and 225 rpm. The fermentation cycle was 72 h. At 24 h and 48 h, adjusted the pH value to pH 7.0 with 10M NaOH. According to glucose consumption in the fermentation broth, added 65% glucose solution to maintain a glucose concentration of 20 g/L. After completion of fermentation, took 1 mL of the fermentation broth and centrifuged. Measured the content of N-Acetyl-D-Glucosamine by HPLC method.

See Table 9 for the output from shake-flask fermentation. The results show that: Compared with the reference strains AT-033 or AT-035, the output of N-Acetyl-D-Glucosamine increased significantly by recombinant strain with transformed wecB/pTrc99A, and increased more greatly by recombinant strain with wecB promoter replaced by Trc promoter.

TABLE 9

Output from Shake-flask Fermentation by Recombinant Strains with Transformed wecB/pTrc99A Plasmid or with wecB promoter replaced by Trc Promoter

| Strains | Output of N-Acetyl-D-Glucosamine (g/L) |
|---|---|
| AT-033 (Reference) | 12.1 ± 1.1 |
| AT-038 (AT-033, wecB/pTrc99A) | 17.3 ± 1.4 |
| AT-039(AT-033, ΔwecB promotor::Trc promoter) | 21.6 ± 1.8 |
| AT-035 (Reference) | 10.1 ± 1.1 |
| AT-040(AT-035, wecB/pTrc99A) | 16.8 ± 1.3 |
| AT-041(AT-035, ΔwecB promotor::Trc promoter) | 20.6 ± 1.5 |

Example 7

This example describes a fermentation experiment for production of N-acetyl-D-glucosamine by a 10-L fermentation tank A fermentation experiment was carried out for production of N-Acetyl-D-Glucosamine by a 10-L fermentation tank, using recombinant engineering strain AT-039 as production strain.

1. Seed Cultivation (1) Cultivation of Primary Seed: Picked monoclonal strain freshly cultured in the LB plate medium, inoculated into 8 mL of LB broth medium, and shake-cultured at 37° C. and 225 rpm for 8 h.
(2) Cultivation of Secondary Seed: Took 6 mL of the primary seed culture solution, inoculated into 1000-mL shake flask containing 200 mL of M9 culture solution, and shake-cultured at 37° C. and 225 rpm for 16 h, until $OD_{600}$ value was 6.0-10, approximately the medium stage of log growth.
(3) Preparation of the fermentation medium according to Table 10, where the microelement solution was prepared according to Table 11, and the complex vitamins solution was prepared according to Table 12.

TABLE 10

Fermentation Medium

| Ingredients | Amount (/L) |
|---|---|
| $K_2HPO_4$ | 1.30 g |
| $KH_2PO_4$ | 1.00 g |
| $MgSO_4 \cdot 7H_2O$ | 0.10 g |
| $NH_4Cl$ | 0.02 g |
| $(NH_4)_2SO_4$ | 0.20 g |
| $NaH_2PO_4$ | 0.60 g |
| Polyether Defoamer | 10 mL |
| Microelement Solution | 4 ml |
| Complex Vitamins Solution | 4 ml |
| Glucose | 6.00 g |

Note:
The microelement solution was sterilized separately and then added, and the vitamins solution was filtered and then added;
Glucose: Concentration of 65% (w/v); it was sterilized separately and added prior to inoculation. Amount to be added: 6.0 g/L;
The above solutions were combined, and then adjusted to pH 7.0 with 10M $NH_4OH$;

The fermentation medium was a basal medium prior to addition of glucose; initial loading amount of the basal medium (initial volume accounting for the total capacity of the fermentation tank): 50%.

TABLE 11

Microelement Solution

| Ingredients | Amount used (g/L) |
|---|---|
| $CaCl_2 \cdot 2H_2O$ | 10 |
| $FeCl_3 \cdot 6H_2O$ | 10 |
| $MnSO_4 \cdot 5H_2O$ | 2.5 |
| $AlCl_3 \cdot 6H_2O$ | 2.5 |
| $CoCl_2 \cdot 6H_2O$ | 1.75 |
| $ZnSO_4 \cdot 2H_2O$ | 0.5 |
| $NaMoO_4 \cdot 2H_2O$ | 0.5 |
| $CuSO_4 \cdot 5H_2O$ | 0.25 |
| $H_3BO_3$ | 0.125 |
| pH | 3 to 4 |

TABLE 12

Complex Vitamins Solution

| Ingredients | Amount (mg/L) |
|---|---|
| Folic Acid | 2 |
| Vitamin $B_2$ Riboflavin | 100 |
| Vitamin $B_1$ Thiamine HCl | 1500 |
| Nicotinic Acid | 500 |
| Vitamin $B_6$ Pyridoxine HCl | 500 |
| Calcium Pantothenate, Ca-panthothenate | 500 |
| Biotin | 1 |
| Vitamin $B_{12}$ | 10 |

2. Inoculation

Inoculated the secondary seed solution to the fermentation tank at a ratio of 40 mL/L; inoculation size: 2.5-5% (v/v); the initial $OD_{600}$ was 0.3-0.5.

3. Process Parameters

High-density fermentation was carried out by a 10-L self-controlled fermentation tank, data were collected by software equipped in the machine to realize online control by computer. The control parameters were: The air flow was 0.5-1 vvm.; dissolved oxygen is >=20%, to increase regulation of rotational speed and ventilation; temperature 37° C.; pH 7.0, the automatic flow was maintained stable by addition of saturated ammonia water. Supplemented glucose when glucose in the basal medium was consumed up, i.e. dissolved oxygen had risen again. Glucose was supplemented in a speed to control residual glucose concentration of no more than 0.45 g/L. The glucose-supplementing solution contained 65% (w/v) of glucose, was added with 2.5% Sodium Gluconate or 6% Ribose. The fermentation was stopped after 60-72 h. Total loading amount: 75%-80%.

4. Example (10-L Fermentation Tank)

(1) Strain No: AT-039. Batch No: 00123.
(2) Concentration of Seed Solution: $OD_{600}$ was 2.8.
(3) Base Stock: 4 L.
(4) Inoculation Size 200 mL.

(5) Glucose supplementation speed: The residual glucose concentration was controlled of no more than 0.45 g/L.
(6) Glucose-supplementing solution: The solution contains glucose in a concentration of 65% (w/v) and was added with 2.5% sodium gluconate.
(7) Track Indicators: Measured $OD_{600}$ and residual glucose content (residual glucose in the fermentation solution).
(8) Product: N-Acetyl-D-Glucosamine. Potency: 72 h, 127.0 g/L.

Example 8

This example describes the treatment process after separation and purification of N-Acetyl-D-Glucosamine and D-Glucosamine Hydrochloride 1. Refinement of N-Acetyl-D-Glucosamine
(1) Deactivation: The fermentation solution was placed at 80° C. for 30 min.
(2) Solid-liquid separation: Centrifuged at 4000-8000 rpm, discarded the bacterial residue and proteins, and transferred the fermentation solution. It may also be filtered via ceramic membrane.
(3) Decoloration: Product: Water: Activated Charcoal=1: (1.5-3): (0.01-0.1); stirred for 0.5-5 h.
(4) Desalt: Desalted by electroosmosis. Initial salt concentration of the fermentation loaded into the concentrated chamber tank: 0.01-0.05 mol/L. Flow rate of the dilute-chamber fermentation solution: 40-80 L/h; flow rate of the concentrated-chamber fermentation solution: 40-80 L/h; the voltage of single membrane pair was 0.5-1.4 V. It may also be desalted by anion or cation ion exchange resin.
(5) Concentration: The fermentation solution desalted was heated at 50-80° C. under vacuum conditions (0.095 MPa) for 8-15 h until oversaturation, by approximately 4-6 folds.
(6) Crystallization: The concentrated fermentation solution was cooled to 25-35° C. in water at 25° C., then cooled for 1-3 h to 0-10° C. in water at 0° C. Anhydrous alcohol was added (in an amount of approximately 5-20 times the product weight), and stirred at 700-1500 rpm for 15 min-1 h.
(7) Washing: Added anhydrous alcohol (same amount as that of the product) and stirred for 10-100 rpm, 0.5-2 h.
(8) Drying: 50-100° C., 3-10 h. Purity: 99.96%. The total yield was 91.5%.

2. Refinement of D-Glucosamine Hydrochloride
(1) Deactivation: The fermentation solution was placed at 80° C. for 30 min.
(2) Solid-liquid separation: Centrifuged at 4000-8000 rpm, discarded the bacterial residue and proteins, and transferred the fermentation solution. It may also be filtered via ceramic membrane.
(3) Decoloration: Product: Water: Activated Charcoal=1: (1.5-3): (0.01-0.1); stirred for 0.5-5 h.
(4) Desalt: Desalt by electroosmosis. Initial salt concentration of the fermentation loaded into the concentrated chamber tank: 0.01-0.05 mol/L. Flow rate of the dilute-chamber fermentation solution: 40-80 L/h; flow rate of the concentrated-chamber fermentation solution: 40-80 L/h; the voltage of single membrane pair was 0.5-1.4 V. It may also be desalted by anion or cation ion exchange resin.
(5) Concentration: The fermentation solution desalted was heated at 50-80° C. under vacuum conditions (0.095 MPa) for 8-15 h until oversaturation, by approximately 4-6 folds.
(6) Hydrolysis: Introduced the concentrated fermentation solution to an enamel or glass container, added concentrated hydrochloric acid (37%) to a final concentration of 12%-16%, stirred thoroughly, and maintained at 70° C. for 90 min. Hydrochloric Acid may be used in a recycling way.
(7) Crystallization: First cooled to 25-35° C. in water at 25° C., and then cooled to 4° C. in water at 0° C. for 1-3 h.
(8) Washing: Added anhydrous alcohol (same amount as that of the product) and stirred for 10-100 rpm, 0.5-2 h. Centrifuged at 700-1500 rpm for 15-60 min to obtain Glucosamine Hydrochloride; the conversion rate is 89.7%.
(9) Dissolution: Dissolve the washed product in water in a similar volume to that of the original fermentation solution.
(10) Decoloration: Added activated charcoal (in an amount of 1%). Mixed for 30 min. Then centrifuged at 700-1500 rpm for 15-60 min. Or filtered to obtain a colorless filtrate.
(11) Recrystallization: Evaporate at 50° C. and 55 cmHg vacuum until oversaturation. Added anhydrous alcohol (in an amount of approximately 5-20 times the product weight), and stirred at 700-1500 rpm for 15 min-1 h.
(12) Washing: Add anhydrous alcohol (same amount as that of the product) and stir for 10-100 rpm, 0.5-2 h. Then centrifuged at 700-1500 rpm for 15-60 min.
(13) Drying: 50-100° C., 3-10 h. Purity: 99.92%. The total yield is 84.3%.

Example 9

This example describes screening for a gene mutant of UDP-N-acetyl-D-glucosamine-2-epimerase (WecB), said gene UDP-N-acetyl-D-glucosamine-2-epimerase, WecB) with increased enzyme activities.

To further increase synthetic quantity of N-Acetyl-D-Glucosamine by the production strain, screen a gene mutant encoding the enzyme with increased enzyme activities. To achieve the purpose, amplifying the cloned gene by error-prone PCR technology, through DNA polymerase used for amplification, amplify said gene under conditions leading to high-frequency mismatch, so as to obtain a high-frequency mutation in PCR products.

The specific operating process is provided below:

1. Amplification of the Gene wecB of UDP-N-Acetyl-D-Glucosamine-2-Epimerase in *Escherichia coli* by Error-Prone PCR By means of Taq DNA polymerase without the property of 3'-5' proofreading function, controlled the frequency of random mutation under high magnesium ion concentration (8 mmol/L) and different dNTP concentrations (the concentration of dATP and dGTP was 1.5 mmol/L; and the concentration of dTTP and dCTP was 3.0 mmol/L), introduced random mutations into the target gene, and constructed a mutation library; the template concentration A260 value was 1000 ng/mL, the enzyme concentration was 5 U/μL, and the primer concentration was 100 μM.

Error-prone PCR reaction system (50 μL): 10×PCR reaction buffer 5 μl, dNTP (2.5 mM) 5 μL, $MgCl_2$ (2.5 mM) 5 μL, Forward primer (TrcwecB-F, SEQ ID No44) 1 μL, reverse primer (TrcwecB-R, SEQ ID No45) 1 μL, DNA template (wecB/pUC57) 0.1 μL, Taq DNA polymerase 0.5 μL, and ddH$_2$O 32.4 μL.

PCR procedure: Pre-degeneration at 96° C. for 4 min; degeneration at 94° C. for 1 min, annealing at 56° C. for 1 min, extension at 75° C. for 2 min, and repeated for 45 cycles; finally extension at 75° C. for 15 min, recovered PCR product (product size: 1.13 kb) by gel recovery method; took 5 μL of the product and carried out 1% agarose gel electrophoresis test; the product was store at −20° C. for use.

2. Construction of the Gene Mutation Library of UDP-N-Acetyl-D-Glucosamine-2-Epimerase Digested the above PCR product by two enzymes of restriction endonuclease Nco I and Hind III, carried out a ligation reaction with pTrc99A digested by Nco I and Hind III, then transformed Escherichia coli AT-005-02 with the mixture of the ligated products to obtain a large amount of cloned transformants, and constructed a mutation library of transformed strains.

3. Screening for Mutants with High Enzyme Activities

Using the wild type WecB/pTrc99A (AT-005-02) as reference, picked up randomly 640 mutant clones from the mutation library of transformed strains, inoculated into 5 mL of LB medium containing 50 μg/mL Ampicillin (Amp), shake-cultured at 37° C. and 150 rpm for 18 h, and then centrifuged at 10000 rpm for 5 mim and collect bacterial solution. Discarded the supernatant, then resuspended at 4° C. in 1 mL of PBS solution (pH 7.5, 10 mmol/L), carried out ultrasonicate at a voltage of 300 V for 10 min (ultrasonicate for 3 s and pause for 6 s), centrifuged, transferred the supernatant as crude extract of enzyme, and carried out a method for determination of enzyme activity.

3. Determination of UDP-N-acetyl-D-glucosamine-2-epimerase activity: Based on the amount of UDP-N-acetyl-D-glucosamine transformed into N-acetyl-D-aminomannose; that is, using the reduced amount of UDP-N-acetyl-D-glucosamine as test marker. Definition of Enzyme Activity Unit: Under the enzymatic reaction conditions, the enzyme amount reduced, equivalent to 1 μmol UDP-N-acetyl-D-glucosamine per minute, is defined as one enzyme activity unit (IU). The specific procedure is provided as follows: First, a 20 ml reaction system was used as an enzyme activity assay system containing 45 mmol/L phosphate buffer (pH 7.5), 10 mM MgCl$_2$ and 100 nCi of UDPGlcNAc and 5 mg of crude enzyme solution. The enzyme was incubated for 30 min in a 37° C. water bath. The reaction was terminated by the addition of ethanol. The radioactive compound was separated by paper chromatography. The radioactivity was measured by a liquid scintillation counter. The solvent system used was n-propanol: 1 M sodium acetate, pH 5.0: water (7:1:2). The activity unit of UDP-N-acetylglucosamine-2-epimerase was calculated based on how much UDPGlcNAc was converted to ManNAc.

The results show that: The enzyme activity of the mutant strain with maximum activity was 653 IU/mL, and the enzyme activity of the reference control was 21 IU/mL. Transforming WecB by error-prone PCR can obtain a mutant strain with increased greatly enzyme activity. Picked up the mutant strain with maximum enzyme activity and extracted plasmids for sequencing. The results show that: The mutant gene sequence of UDP-N-acetylglucosamine-2-epimerase is shown as SEQ ID No49, and the corresponding amino acid sequence is shown as SEQ ID No50. Through gene sequence alignment with the wild type of UDP-N-acetylglucosamine-2-epimerase, 5 base point mutations occurred in total: 101G/C, 433C/G, 677G/T, 734T/G, and 1038T/C. There occurred 4 missense mutations of amino acids, of which the mutation points are: C34S (cysteine at position 34 is changed to serine), H145D (histidine at position 145 is changed to aspartic acid), C226F (cysteine at position 226 is changed to phenylalanine), and V245G (valine at position 245 becomes glycine). The mutant gene is named as wecBM.

4. Integration of pTrc-wecBM Gene Cassette into the nagE Gene Site in the Chromosome of Escherichia Coli The nagE gene site was used as integration site of pTrc-wecBM gene cassette into the chromosome. To achieve integration of pTrc-wecBM gene cassette into the chromosome of Escherichia coli, first amplified the wecBM segment containing Trc promoter, i.e. pTrc-wecBM, as well as the kanamycin resistance gene segment with FLP recognition site (FRT site) at its both ends: FRT-Kanr-FRT (fKanrf), and spliced them. Then designed homology arm primers for deletion of the nagE gene sequence, and using the spliced segment of pTrc-wecBM and fKanrf as template, amplified the linear DNA full-length segment for Red recombination targeting.

The specific operating process is provided below:

(1) PCR Amplification of pTrc-wecBM Segment

Template: wecBM/pTrc99A.

Primer Design: Forward primer (Treff-F) SEQ ID No20, and reverse primer (Treff-R) SEQ ID No21.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Product Size: 1.3 kb.

The PCR product was separated by 1% agarose gel electrophoresis, and purified to recover the segment.

(2) PCR Amplification of fKanrf Segment

Primer Design: Forward primer (mfKanf-F) SEQ ID No1, and reverse primer (mfKanf-R) SEQ ID No2.

Template: pPic9K.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

fKanrf size: 1.28 kb. Its nucleotide sequence is SEQ ID No3.

The PCR product was separated by 1% agarose gel electrophoresis, and purified to recover the segment.

(3) Amplification of fKanrf Spliced with pTrc-wecBM

Primer Design: Forward primer (fKanf-F) SEQ ID No22, and reverse primer (fKanf-R) SEQ ID No23.

Template: fKanrf.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

fKanrf size from secondary amplification: 1.3 kb.

The PCR product was separated by 1% agarose gel electrophoresis, and purified to recover the segment.

(4) Preparation of Linear DNA Full-Length PCR Segment for Red Recombination Targeting Design of Homologous Arm Primers: Designed again homologous arm primers for deletion of the nagE gene sequence: Forward primer (nagEKO-F2) SEQ ID No24, and reverse primer (nagEKO-R2) SEQ ID No25.

Template: Mixed pTrc-wecBM PCR segment, and fKanrfPCR segment from secondary amplification at a ratio of 1:1.

PCR reaction conditions: Step 1: Degeneration at 94° C. for 1 min; Step 2: Incubation at 94° C. for 30 s, at 55° C. for 30 s, and at 72° C. for 40 s, and carrying out 30 cycles; Step 3: Extension at 72° C. for 10 min.

Amplification Product: Homologous Arm+pTrc-wecBM-fKanrf+Homologous Arm

The PCR product was separated by agarose gel electrophoresis, and purified and recovered to obtain 100 ng/μL linear DNA full-length PCR segment for Red recombination targeting.

(5) Red Recombination Operation

First, pKD46 carrier was introduced into the AT-004-02 strain of *Escherichia coli*. Then, the prepared linear DNA segment for targeting was electrotransformed, and positive clones were screened. Finally, the resistance gene was removed.

1) Transformation of pKD46 Plasmid
① Preparation of Competence:

First, inoculated the bacterial suspension of *Escherichia coli* AT-004-02 stored at −20° C. into 10 mL of LB broth medium in a ratio of 1:50-100, and shake-cultured at 37° C. and 225 rpm for 2-3 h. Then added the culture solution to a 10-mL centrifuge tube, centrifuged at 4000 g×5 min, discarded the supernatant, and suspended with 5 mL 0.1M $CaCl_2$ on an ice bath for 5 min. Finally, centrifuged at 4000 g×5 min, discarded the supernatant, and suspended with 5 mL of 0.1M $CaCl_2$ on an ice bath. Allowed to stand at −4° C. for 12 h for natural sedimentation.

⊖ Plasmid Transformation: Took 250 μL of naturally settled bacterial solution, added 5 μL of pKD46 plasmid, and cultured at −4° C. for 30 min. Then heated on a water bath at 42° C. for 1.5 min, added 0.7 mL of SOC medium, and shook at 30° C. for 2 h. Took 0.2 mL of the bacterial suspension, and smeared on a penicillin plate. Cultured overnight (for 12-16 h) at 30° C. Picked up monoclone, added 5 mL of LB broth medium and cultured, and plasmid was extracted for identification. Stored the positive strain for use.

2) Electrotransform Linear DNA Segment for Targeting, and Screen Positive Clone
① Preparation of Electrotransform Competence:

Inoculated the AT-004-02 strain of *Escherichia coli*, containing pKD46, into a test tube of LB medium containing Ampicillin (Amp), and shake-cultured at 250 rpm, on the next day, inoculated at a ratio of 1% into LB medium containing Amp, and cultured at 30° C.; when $OD_{600}$ reached about 0.2, added 0.2% L-Arabinose, and induced at 30° C. for 35 min until $OD_{600}$ reached about 0.4. Cooled on an ice bath. Washed once with ultrapure water, washed twice with 10% glycerin, and finally resuspended with 10% glycerin; the amount of glycerin used was to produce a final concentration of the bacterial solution concentrated by 500-1000 folds.

⊖ Transformation by electric shock: Took out a 2-mm electrotransformation cup from 70% ethanol, washed twice with sterilized ultrapure water, and irradiated by UV lamp for 30 min. Precooled at 4° C. for 30 min. Took 90 μL of finally resuspended cells to a precooled centrifuge tube, added 5 μL (more than 100 ng) of the full-length PCR segment (linear DNA) obtained in Step (4), gently suction mixed with a gun, and maintained on an ice bath for 30 min. Electrotransformation Parameters: 2500V, 20011, 25 μF.

③ Resuscitate and Screen Positive Clones:

added 1 mL of LB broth medium, and cultured at 37° C. and 100 rpm for 1 h. Then smeared one kanamycin (Kan) plate with every 200 μL, 5 plates in total. Smeared evenly and allowed to dry. Cultured at 30° C. for 24 h. Picked up clones grown under kanamycin resistance, and carried out PCR identification to screen positive clones.

No of the obtained strain: AT-043-01 (AT-004-02, ΔnagE::pTrc-wecBM-fKanrf).

As described above, prepared the strain AT-042-01 (AT-004-02, ΔnagE::pTrc-wecB-fKanrf).

(6) Removal of the Resistance Gene

Introduced pCP20 into the above kanamycin-resistant clones, cultured at 30° C. for 8 h, then increased to 42° C. and cultured overnight, and thermally induced to express FLP recombinase; the plasmids were lost gradually. Streaked the plate of antibiotics-free culture medium by an inoculating loop dipped in the bacterial suspension, picked up grown monoclones and dotted on the kanamycin-resistant plate; those that did not grow were clones of which the kanamycin resistance gene had been removed by FLP recombination. Carried out PCR with identification primer to identify clones that had lost kanamycin resistance.

No of the obtained strain: AT-043-02 (AT-004-02, ΔnagE::pTrc-wecEM).

As described above, prepared the strain AT-042-02 (AT-004-02, ΔnagE::pTrc-wecB).

5. Influence of the Integration of pTrc-wecB and pTrc-wecBM Gene Cassettes on the Output of N-Acetyl-D-Glucosamine Carrying out a shake-flask fermentation experiment with the recombinant strains AT-042-02 and AT-043-02, of which the nagE gene site in the chromosome was integrated with pTrc-wecB and pTrc-wecBM gene cassettes, and the reference strain. Transferred the monoclonal strain freshly cultivated in culture medium of the LB plate, inoculated into a test tube (13×150 mm) containing 3 mL of the LB broth culture medium, and shake-cultured at 30° C. for 8 h. Then transferred the seed culture solution, inoculated 3% into a 250-mL shake-flask containing 50 mL of the fermentation culture solution (M9 culture solution). The initial $OD_{600}$ was about 0.5; shake-cultured at 37° C. and 225 rpm. The fermentation cycle was 72 h. At 24 h and 48 h, adjusted the pH value to pH 7.0 with 10M NaOH. According to glucose consumption in the fermentation broth, added 65% glucose solution to maintain a glucose concentration of 20 g/L. After completion of fermentation, transferred 1 mL of the fermentation broth and centrifuged. Measured the content of N-Acetyl-D-Glucosamine by HPLC method.

See Table 13 for the output from shake-flask fermentation. The results show that: The output by the reference strain AT-005-02 was very low and was not detected, while the output by the recombinant strain AT-043-02 integrated with pTrc-wecBM gene cassette increased significantly, and also increased significantly than that by the unmutant reference strain AT-042-02.

TABLE 13

Output from Shake-flask Fermentation by the Recombinant Strain integrated with pTrc-wecBM Gene Cassette

| Strains | Output of N-Acetyl-D-Glucosamine (g/L) |
|---|---|
| AT-005-02 (AT-004-02, ΔnagE) (Reference) | Not detected |
| AT-042-02 (AT-004-02, ΔnagE::pTrc-nanE) | 7.1 ± 0.8 |
| AT-043-02 (AT-004-02, ΔnagE::pTrc-nanEM) | 10.9 ± 0.9 |

The above results show that: The output of N-Acetyl-D-Glucosamine may be increased significantly by overexpression of UDP-N-acetyl-d-glucosamine-2-epimerase; moreover, the output of N-Acetyl-D-Glucosamine may also be greatly increased by the mutant screened by error-prone PCR technology, due to increased activities of the obtained mutant of the epimerase.

The invention claimed is:

1. A method for producing N-Acetyl-D-Glucosamine and/or D-Glucosamine salt by microbial fermentation, comprising:

A) culturing a microorganism in a fermentation medium to produce said N-Acetyl-D-Glucosamine and/or D-Glucosamine salt, wherein said microorganism is transformed with at least one recombinant nucleic acid molecule comprising a nucleic acid sequence encoding N-acetyl-D-aminomannose-6-phosphate epimerase (NanE); said nucleic acid sequence encoding N-acetyl-D-aminomannose-6-phosphate epimerase (NanE) comprises at least one genetic modification that increases the activity of N-acetyl-D-aminomannose-6-phosphate epimerase (NanE) relative to a N-acetyl-D-aminomannose-6-phosphate epimerase without said genetic modification; wherein said N-acetyl-D-aminomannose-6-phosphate epimerase comprises an amino acid sequence having at least 95% sequence identity to the amino acid sequence of SEQ ID NO: 17 and the cysteine at position 133 of the amino acid sequence of SEQ ID NO: 17 is substituted with arginine and the tyrosine at position 187 of the amino acid sequence of SEQ ID NO: 17 is substituted with histidine ; and B) collecting N-Acetyl-D-Glucosamine and/or D-Glucosamine salt produced in the culturing step A).

2. The method of claim 1, wherein said nucleic acid sequence encoding N-acetyl-D-aminomannose-6-phosphate epimerase (NanE) comprises the nucleic acid sequence of SEQ ID NO: 26.

3. The method of claim 1, wherein said microorganism further comprises one or more of the following genetic modifications:
   (1) at least one genetic modification capable of enhancing the activity of D-glucosamine-6-phosphate deaminase in said microorganism relative to a microorganism without said genetic modification, and simultaneously comprising at least one genetic modification capable of reducing the activity of glucosamine-6-phosphate synthase relative to a microorganism without said genetic modification;
   (2) at least one genetic modification capable of increasing the activity of glucosamine-6-phosphate synthase in said microorganism relative to a microorganism without said genetic modification, and simultaneously comprising at least one genetic modification capable of reducing the activity of D-glucosamine-6-phosphate deaminase relative to a microorganism without said genetic modification;
   (3) at least one genetic modification capable of enhancing the activity of UDP-N-acetyl-D-glucosamine-2-epimerase (WecB) in said microorganism relative to a microorganism without said genetic modification.

4. The method of claim 3, wherein said genetic modification capable of enhancing the activity of UDP-N-acetyl-D-glucosamine-2-epimerase (WecB) in said microorganism is selected from the group consisting of a) increased activity of UDP-N-acetyl-D-glucose-2-epimerase; and/or b) overexpression of UDP-N-acetyl-D-glucosamine-2-epimerase in said microorganism.

5. The method of claim 4, wherein said microorganism is transformed with at least one recombinant nucleic acid molecule comprising a nucleic acid sequence encoding UDP-N-acetyl-D-glucosamine-2-epimerase; wherein said nucleic acid sequence encoding UDP-N-acetyl-D-glucosamine-2-epimerase comprises the nucleic acid sequence of SEQ ID NO: 49.

6. The method of claim 1, wherein said microorganism further comprises one or more of the following genetic modifications:
   (1) at least one genetic modification capable of reducing the activity of mannose transporter EIIM, P/III$^{man}$ (ManXYZ) in said microorganism relative to a microorganism without said genetic modification;
   (2) at least one genetic modification capable of reducing the activity of N-acetylneuraminic acid lyase (NanA) in said microorganism relative to a microorganism without said genetic modification;
   (3) at least one genetic modification capable of reducing the activity of N-acetyl-D-glucosamine-6-phosphate deacetylase (NagA) in said microorganism relative to a microorganism without said genetic modification;
   (4) at least one genetic modification capable of reducing the activity of N-acetyl-D-glucosamine specific enzyme II$^{Nag}$ (NagE) in said microorganism relative to a microorganism without said genetic modification;
   (5) at least one genetic modification capable of increasing the activity of a phosphoglucosamine mutase (GlmM) in said microorganism relative to a microorganism without said genetic modification; and
   (6) at least one genetic modification capable of enhancing the activity of bifunctional enzyme N-acetyl-D-glucosamine-1-phosphate uridine acyltransferase (GlmU) in said microorganism relative to a microorganism without said genetic modification.

7. The method of claim 1, wherein said culturing step A) is carried out at a temperature of from 20° C. to 45° C.; wherein said culturing step A) is carried out at a pH value of from pH 4.5 to pH 8.5; wherein said culturing step A) uses a sugar-retaining liquid fed fermentation process.

8. The method of claim 1, wherein said microorganism is a bacterium, a yeast or a fungus.

* * * * *

SEQUENCE LISTING

```
<160> NUMBER OF SEQ ID NOS: 50

<210> SEQ ID NO 1
<211> LENGTH: 70
<212> TYPE: DNA
<213> ORGANISM: Artificial Sequence
<220> FEATURE:
<223> OTHER INFORMATION: Product of the human mind.

<400> SEQUENCE: 1
gtaaaacgac ggccagtgga agttcctata ctttctagag aataggaact tcctcgtgaa    60
gaaggtgttg                                                          70

<210> SEQ ID NO 2
<211> LENGTH: 80
<212> TYPE: DNA
<213> ORGANISM: Artificial Sequence
<220> FEATURE:
<223> OTHER INFORMATION: Product of the human mind.

<400> SEQUENCE: 2
ggaaacagct atgaccatgc ctattccgaa gttcctattc tctagaaagt ataggaactt    60
ctgttacatt gcacaagata                                               80

<210> SEQ ID NO 3
<211> LENGTH: 1283
<212> TYPE: DNA
<213> ORGANISM: Artificial Sequence
<220> FEATURE:
<223> OTHER INFORMATION: Product of the human mind.

<400> SEQUENCE: 3
gtaaaacgac ggccagtgga agttcctata ctttctagag aataggaact tcctcgtgaa    60
gaaggtgttg ctgactcata ccaggcctga atcgccccat catccagcca gaaagtgagg   120
gagccacggt tgatgagagc tttgttgtag gtggaccagt tggtgatttt gaacttttgc   180
tttgccacgg aacggtctgc gttgtcggga agatgcgtga tctgatcctt caactcagca   240
aaagttcgat ttattcaaca aagccgccgt cccgtcaagt cagcgtaatg ctctgccagt   300
gttacaacca attaaccaat tctgattaga aaaactcatc gagcatcaaa tgaaactgca   360
atttattcat atcaggatta tcaataccat attttttgaaa aagccgtttc tgtaatgaag   420
gagaaaactc accgaggcag ttccatagga tggcaagatc ctggtatcgg tctgcgattc   480
cgactcgtcc aacatcaata caacctatta atttcccctc gtcaaaaata aggttatcaa   540
gtgagaaatc accatgagtg acgactgaat ccggtgagaa tggcaaaagc ttatgcattt   600 cttccagac ttgttcaaca ggccagccat tacgctcgtc atcaaaatca ctcgcatcaa   660
ccaaaccgtt attcattcgt gattgcgcct gagcgagacg aaatacgcga tcgctgttaa   720
aaggacaatt acaaacagga atcgaatgca accggcgcag gaacactgcc agcgcatcaa   780
caatattttc acctgaatca ggatattctt ctaatacctg gaatgctgtt ttcccgggga   840
tcgcagtggt gagtaaccat gcatcatcag gagtacggat aaaatgcttg atggtcggaa   900
gaggcataaa ttccgtcagc cagtttagtc tgaccatctc atctgtaaca tcattggcaa   960
cgctaccttt gccatgtttc agaaacaact ctggcgcatc gggcttccca tacaatcgat  1020
```

```
agattgtcgc acctgattgc ccgacattat cgcgagccca tttatacccca tataaatcag   1080 catccatgtt ggaatttaat cgcggcctcg agcaagacgt ttcccgttga atatggctca   1140
taacacccct tgtattactg tttatgtaag cagacagttt tattgttcat gatgatatat   1200
ttttatcttg tgcaatgtaa cagaagttcc tatactttct agagaatagg aacttcggaa   1260
taggcatggt catagctgtt tcc                                            1283

<210> SEQ ID NO 4
<211> LENGTH: 2699
<212> TYPE: DNA
<213> ORGANISM: Escherichia coli

<400> SEQUENCE: 4
gtgaccattg ctattgttat aggcacacat ggttgggctg cagagcagtt gcttaaaacg     60
gcagaaatgc tgttaggcga gcaggaaaac gtcggctgga tcgatttcgt tccaggtgaa    120
aatgccgaaa cgctgattga aaagtacaac gctcagttgg caaaactcga caccactaaa    180
ggcgtgctgt ttctcgttga tacatgggga ggcagcccgt tcaatgctgc cagccgcatt    240
gtcgtcgaca aagagcatta tgaagtcatt gcaggcgtta acattccaat gctcgtggaa    300
acgttaatgg cccgtgatga tgacccaagc tttgatgaac tggtggcact ggcagtagaa    360
acaggccgtg aaggcgtgaa agcactgaaa gccaaaccgg ttgaaaaagc gcgccagca    420 cccgctgccg cagcaccaaa agcggctcca actccggcaa aaccaatggg ccaaacgac    480 tacatggtta ttggccttgc gcgtatcgac gaccgtctga ttcacggtca ggtcgccacc    540
cgctggacca agaaaccaa tgtctcccgt attattgttg ttagtgatga agtggctgcg    600
gataccgttc gtaagacact gctcacccag gttgcacctc cgggcgtaac agcacacgta    660
gttgatgttg ccaaaatgat tcgcgtctac aacaacccga aatatgctgg cgaacgcgta    720
atgctgttat ttaccaaccc aacagatgta gagcgtctcg ttgaaggcgg cgtgaaaatc    780
acctctgtta acgtcggtgg tatggcattc cgtcagggta aaacccaggt gaataacgcg    840
gtttcggttg atgaaaaaga tatcgaggcg ttcaagaaac tgaatgcgcg cggtattgag    900
ctggaagtcc gtaaggtttc caccgatccg aaactgaaaa tgatggatct gatcagcaaa    960
atcgataagt aacgtattgt gttgattatc actcagtttt cacacttaag tcttacgtaa   1020
acaggagaag tacaatggag attaccactc ttcaaattgt gctggtattt atcgtagcct   1080
gtatcgcagg tatgggatca atcctcgatg aatttcagtt tcaccgtccg ctaatcgcgt   1140
gtaccctggt gggtatcgtt cttggggata tgaaaaccgg tattattatc ggtggtacgc   1200
tggaaatgat cgcgctgggc tggatgaaca tcggtgctgc agttgcgcct gacgccgctc   1260
tggcttctat catttctacc attctggtta tcgcaggtca tcagagcatt ggtgcaggta   1320
tcgcactggc aatccctctg ccgctgcggg gccaggtact gaccatcatc gttcgtacta   1380
ttaccgttgc tttccagcac gctgcggata aggctgctga taacggcaac tgcagacgca   1440
tttcctggat ccacgtttct tctctgttcc tgcaagcaat gcgtgtggct attccggccg   1500
tcatcgttgc gctgtctgtt ggtaccagcg aagtacagaa catgctgaat gcgattccgg   1560
aagtggtgac caatggtctg aatatcgccg gtggcatgat cgtggtggtt ggttatgcga   1620
tggttatcaa catgatgcgt gctggctacc tgatgccgtt cttctacctc ggcttcgtaa   1680
ccgcagcatt caccaacttt aacctggttg ctctgggtgt gattggtact gttatggcag   1740
tgctctacat ccaacttagc ccgaaataca accgcgtagc cggtgcgcct gctcaggcag   1800
ctggtaacaa cgatctcgat aacgaactgg actaacaggt gagcgaaatg gttgatacaa   1860
```

```
ctcaaactac caccgagaaa aaactcactc aaagtgatat tcgtggcgtc ttcctgcgtt      1920
ctaacctctt ccagggttca tggaacttcg aacgtatgca ggcactgggt ttctgcttct      1980
ctatggtacc ggcaattcgt cgcctctacc ctgagaacaa cgaagctcgt aaacaagcta      2040
ttcgccgtca cctggagttc tttaacaccc agccgttcgt ggctgcgccg attctcggcg      2100
taaccctggc gctggaagaa cagcgtgcta atggcgcaga gatcgacgac ggtgctatca      2160
acggtatcaa agtcggtttg atggggccac tggctggtgt aggcgacccg atcttctggg      2220
gaaccgtacg tccggtattt gcagcactgg gtgccggtat cgcgatgagc ggcagcctgt      2280
taggtccgct gctgttcttc atcctgttta acctggtgcg tctggcaacc cgttactacg      2340
gcgtagcgta tggttactcc aaaggtatcg atatcgttaa agatatgggt ggtggcttcc      2400
tgcaaaaact gacggaaggg gcgtctatcc tcggcctgtt tgtcatgggg gcattggtta      2460
acaagtggac acatgtcaac atcccgctgg ttgtctctcg cattactgac cagacgggca      2520
aagaacacgt tactactgtc cagactattc tggaccagtt aatgccaggc ctggtaccac      2580
tgctgctgac ctttgcttgt atgtggctac tgcgcaaaaa agttaacccg ctgtggatca      2640
tcgttggctt cttcgtcatc ggtatcgctg gttacgcttg cggcctgctg ggactgtaa       2699
```

<210> SEQ ID NO 5
<211> LENGTH: 68
<212> TYPE: DNA
<213> ORGANISM: Artificial Sequence
<220> FEATURE:
<223> OTHER INFORMATION: Product of the human mind.

<400> SEQUENCE: 5

```
gtgaccattg ctattgttat aggcacacat ggttgggctg cagagcagtt gtaaaacgac      60
ggccagtg                                                                68
```

<210> SEQ ID NO 6
<211> LENGTH: 69
<212> TYPE: DNA
<213> ORGANISM: Artificial Sequence
<220> FEATURE:
<223> OTHER INFORMATION: Product of the human mind.

<400> SEQUENCE: 6

```
ttacagtccc agcaggccgc aagcgtaacc agcgataccg atgacgaaga ggaaacagct      60
atgaccatg                                                               69
```

<210> SEQ ID NO 7
<211> LENGTH: 1030
<212> TYPE: DNA
<213> ORGANISM: Escherichia coli

<400> SEQUENCE: 7

```
cacgctttgg tatgaaaatt gtagggtaca gatgcgttta tttcccctca cccggtaggg      60
gcgagcgagg ggaaacaact cacccgcgct cttgcatcaa ctgctgggcc agcgccttca     120
gttctggcag atattttca tctaccggtc caaacggttt gcggcacagc ggcacagaaa     180
cgacatccat ataatggagg acagttttca ggccgcggaa tacgcccgtt ttgatcagta     240
aatcaatgac tttattgcat tcagtttgca gtttctgcgc ggtctggata tcgccttctt     300
tcagcgccct aacgatcccc tgatagcgcc agcccatgat gttgtaggta ctgccgatac     360
caccatcagc gcccgccagc agaccagagg cgaagatttc gtcgtaaccg ttatagagca     420
```

```
caagatcagg atgttcacga cggatctgct ccatctgata gagatcgcca gaggtctgtt    480
tcagcgcacc tacgccaggc aatgtaacaa gtgtgttgat ctgatccagg gtcagtttta   540
ccccactcag ggctggaatg ttgtacacca ccatcggcaa accatccgcc gaatcaataa   600
ttgcccgata gtgatcgcag tgttcttcaa agctgaaagg atagtagaac ggcgtgacgg   660
cggagacggc atcgaagcca taacgtttag ccgatgccgc aagttgttgg ctttcggcgg   720
tgctgacgca accgacgtgg gcgatgagtt taatcttacc tttcgcctct cggcgacga    780 tttccagtac ctgttcacgc tcggaaaggc tttgtacaaa ggcctcgccg gtcgaaccac   840
ccacgtataa accgtcgatg ccctgctgaa tattgaactg aaccaggcga cgcagactcg   900
ctttatccag tgcttgttgt tggtcaaaag gagtcaggag tgcagccatt acgccacgta   960
aattcgttgc cataaatacc tctgaagtga tgcttgtctg ataaacgata tacctttata  1020
cctgttatac                                                         1030
```

<210> SEQ ID NO 8
<211> LENGTH: 68
<212> TYPE: DNA
<213> ORGANISM: Artificial Sequence
<220> FEATURE:
<223> OTHER INFORMATION: Product of the human mind.

<400> SEQUENCE: 8

```
cacgctttgg tatgaaaatt gtagggtaca gatgcgttta tttcccctca gtaaaacgac    60
ggccagtg                                                            68
```

<210> SEQ ID NO 9
<211> LENGTH: 76
<212> TYPE: DNA
<213> ORGANISM: Artificial Sequence
<220> FEATURE:
<223> OTHER INFORMATION: Product of the human mind.

<400> SEQUENCE: 9

```
gtataacagg tataaaggta tatcgtttat cagacaagca tcacttcaga ggtatttgga    60
aacagctatg accatg                                                   76
```

<210> SEQ ID NO 10
<211> LENGTH: 1200
<212> TYPE: DNA
<213> ORGANISM: Escherichia coli

<400> SEQUENCE: 10

```
tttaaaatcg ggggtcagaa tgtatgcatt aacccagggc cggatcttta ccggccacga    60
atttcttgat gaccacgcgg ttgttatcgc tgatggcctg attaaaagcg tctgtccggt   120
agcggaactg ccgccagaga tcgaacaacg ttcactgaac ggggccattc tctcccccgg   180
ttttatcgat gtgcagttaa acggctgcgg cggcgtacag tttaacgaca ccgctgaagc   240
ggtcagcgtg gaaacgctgg aaatcatgca gaaagccaat gagaaatcag gctgtactaa   300
ctatctgccg acgcttatca ccaccagcga tgagctgatg aaacagggcg tgcgcgttat   360
gcgcgagtac ctggcaaaac atccgaatca ggcgttaggt ctgcatctgg aaggtccgtg   420
gctgaatctg gtaaaaaaag gcacccataa tccgaatttt gtgcgtaagc ctgatgccgc   480
gctggtcgat ttcctgtgtg aaacgccgga cgtcattacc aaagtgaccc tggcaccgga   540
aatggttcct gcggaagtca tcagcaaact ggcaaatgcc gggattgtgg tttctgccgg   600
tcactccaac gcgacgttga agaagcaaa agccggtttc cgcgcgggga ttacctttgc   660
```

```
cacccatctg tacaacgcga tgccgtatat taccggtcgt gaacctggcc tggcgggcgc    720
gatcctcgac gaagctgaca tttattgcgg tattattgct gatggcctgc atgttgatta    780
cgccaacatt cgcaacgcta aacgtctgaa aggcgacaaa ctgtgtctgg ttactgacgc    840
caccgcgcca gcaggtgcca acattgaaca gttcattttt gcgggtaaaa caatatacta    900
ccgtaacgga ctttgtgtgg atgagaacgg tacgttaagc ggttcatcct taaccatgat    960
tgaaggcgtg cgtaatctgg tcgaacattg cggtatcgca ctggatgaag tgctacgtat   1020
ggcgacgctc tatccggcgc gtgcgattgg cgttgagaaa cgtctcggca cactcgccgc   1080
aggtaaagta gccaacctga ctgcattcac acctgatttt aaaatcacca agaccatcgt   1140
taacggtaac gaggtcgtaa ctcaataaga gaaagtatga caccaggcgg acaagctcag   1200
```

<210> SEQ ID NO 11
<211> LENGTH: 68
<212> TYPE: DNA
<213> ORGANISM: Artificial Sequence
<220> FEATURE:
<223> OTHER INFORMATION: Product of the human mind.

<400> SEQUENCE: 11

```
tttaaaatcg ggggtcagaa tgtatgcatt aacccagggc cggatcttta gtaaaacgac     60
ggccagtg                                                              68
```

<210> SEQ ID NO 12
<211> LENGTH: 69
<212> TYPE: DNA
<213> ORGANISM: Artificial Sequence
<220> FEATURE:
<223> OTHER INFORMATION: Product of the human mind.

<400> SEQUENCE: 12

```
ctgagcttgt ccgcctggtg tcatactttc tcttattgag ttacgacctc ggaaacagct     60
atgaccatg                                                             69
```

<210> SEQ ID NO 13
<211> LENGTH: 2350
<212> TYPE: DNA
<213> ORGANISM: Escherichia coli

<400> SEQUENCE: 13

```
cgcatcaggc ataaagcaga ttacttttg atttcataca gcggtgtttg acccgccaca      60
atatggccct gagctttaat gatcaagcca ctgaaatcgt cgatattgct gcaaaccacc    120
gggctaatca tcgagcgggc gttagcgttc aggtaatcca gatccatttc cagaatcggt    180
tgccctgcgc ttacctgcgc accctcttcc accagacgtt taaagccttt accttccagc    240
gctacggtgt cgatacccat atggacgacg atctccgcgc cttttttcggt ttccaggcag    300 aacgcgtggt tggtgttgaa gattttcacg attgtccctg cggctggtga tacgacgatt    360
ttatctgtcg gtttcaccgc cacaccgtca cccaccgctt tgctggcgaa tgcttcgtca    420
ggaacctgat ccagtgccac gacatcaccg gtaatcggcg ataccagctc cgcgatagat    480
accgcgtttg gtacagcctg cggttttgct acaggcgcgg cagttgccgg agttgcttca    540
gctgacgcag cggctaccgg accacgggca acgactttct tcatcgcatc gccgatggat    600
tctgctttcg cgccaacaat cacctgaata gtctgtttgt tcagtttcac taccccagaa    660
gcacccagac gtttacacat cgtatcgtta acgcgggcag agtcagccac tgtaaggcgc    720
```

```
agacgggtga tacaggcgtc aatcgctttc aggttgtcag tgccgccaac cgcagcaata    780
tagttggttg ccagttgagt cagaccttct tcagtgttgc tgttggcttc ttcagtaacg    840
atctcgtctt ctttatcttc acgacccggc gttttcaggt tgaacatgcg gataaccaaa    900
ctgaacacca cgaagtagat agcgaagaag ataacgccca tcaccagcag catccagacg    960
ttctggctgg cggccggcag gttatacatc aacgcgtagt cgatagcccc cgcagagaaa   1020
gagaagcccg cgtggatacc cagcagcgtt gccacaaaca ggctgatacc ggtcagcagt   1080
gcgtgcagga ggtacagcag cggagcaagg aacatgaaca ggaattccag cggctcagtc   1140
acaccggtca ggaacgcagt aacagcaaca gaaagcagca taccgccaac catcggacga   1200 cgctcttcg gtgctgcgaa gtacatcgcc agcgccgcac ccggcagacc gaacatcatg     1260
atcgggaaga agccggacat gaacatcccc gcggtgccgt caccggcata gaagcggtta   1320
atgtcaccgt ggaaaaccgt acccgccgcg ttggtgaatt caccaatctg gaaccaggcg   1380
atggtgttca gtacctgatg cagaccggtt gggatcagca gacggttgat gaaaccaaag   1440
ataccggaac ccagcgcgcc cgcagaaacg atccactcgc cgcctgcatg gatagcgtgc   1500
tgtaccggcg gccagacgta accaaaaatg gccgccagca ccaggcagaa gaatccggtg   1560
gcaatcggca caaagcgttt gccgccgaag aagctcagga agtccggcag tttaatatcg   1620
gaccaacggt tataggctgc gccaccaacc agaccggtaa tgataccgc cagtacaccc     1680 atgttaattt ctgggttgat ggtcaccatc gctttggtta acacaaagta acctaccgca   1740
cccgccagcg ccgccgcacc agcgctgtct ttcgaccagc tggatgccac accgatggcg   1800
aagattaatg cgaggttatc aaaaatcgca ccgcccgcct gggcaataaa cgcaacgtta   1860
agtaaatctg gctgaccgaa tcgcagcaac agtgccgcca ccggcagcac cgcgataggg   1920
agctgtaacg ccctaccgag tcgctggaaa aaacctaaaa tattcatctt attccccta     1980 cgagaaccct atttggctcg tttcaagccg tatttttatt ttgctgcaaa ttgtactgcc   2040
gatgttctgt aatcagattg ttagatcatc tgctacagag tgtgtgaaaa tttaattcgt   2100
atcgcaaatt aaacgcgtgt cttttgtgag ttttgtcacc aaatatcgtt attatcactc   2160
ccttttactg gctaaaccag aaaacttatt ttatcattca aaaaatcagg tcggattgac   2220
gcctgtctgc gcaaatccag gttacgctta aagatgccta atccgccaac ggcttacatt   2280
ttacttattg aggtgaataa tgagactgat cccctgact accgctgaac aggtcggcaa     2340
atgggctgct                                                          2350

<210> SEQ ID NO 14
<211> LENGTH: 68
<212> TYPE: DNA
<213> ORGANISM: Artificial Sequence
<220> FEATURE:
<223> OTHER INFORMATION: Product of the human mind.

<400> SEQUENCE: 14
cgcatcaggc ataaagcaga ttacttttg atttcataca gcggtgtttg gtaaaacgac       60
ggccagtg                                                              68

<210> SEQ ID NO 15
<211> LENGTH: 68
<212> TYPE: DNA
<213> ORGANISM: Artificial Sequence
<220> FEATURE:
<223> OTHER INFORMATION: Product of the human mind.

<400> SEQUENCE: 15
```

-continued

```
agatgaatat tttaggtttt ttccagcgac tcggtagggc gttacagctg gaaacagcta      60
tgaccatg                                                                68
```

<210> SEQ ID NO 16
<211> LENGTH: 690
<212> TYPE: DNA
<213> ORGANISM: Escherichia coli

<400> SEQUENCE: 16

```
atgtcgttac ttgcacaact ggatcaaaaa atcgctgcta acggtggcct gattgtctcc      60
tgccagccgg ttccggacag cccgctcgat aaacccgaaa tcgtcgccgc catggcatta     120
gcggcagaac aggcgggcgc ggttgccatt cgcattgaag gtgtggcaaa tctgcaagcc     180
acgcgtgcgg tggtgagcgt gccgattatt ggaattgtga acgcgatct  ggaggattct     240 ccggtacgca tcacggccta tattgaagat gttgatgcgc tggcgcaggc gggcgcggac     300
attatcgcca ttgacggcac cgaccgcccg cgtccggtgc ctgttgaaac gctgctggca     360
cgtattcacc atcacggttt actggcgatg accgactgct caacgccgga agacggcctg     420
gcatgccaaa agctgggagc cgaaattatt ggcactacgc tttctggcta taccacgcct     480
gaaacgccag aagagccgga tctggcgctg gtgaaaacgt tgagcgacgc cggatgtcgg     540
gtgattgccg aagggcgtta caacacgcct gctcaggcgg cggatgcgat cgccacggc      600 gcgtgggcgg tgacggtcgg ttctgcaatc acgcgtcttg agcacatttg tcagtggtac     660
aacacagcga tgaaaaaggc ggtgctatga                                       690
```

<210> SEQ ID NO 17
<211> LENGTH: 229
<212> TYPE: PRT
<213> ORGANISM: Escherichia coli

<400> SEQUENCE: 17

```
Met Ser Leu Leu Ala Gln Leu Asp Gln Lys Ile Ala Ala Asn Gly Gly
1               5                   10                  15

Leu Ile Val Ser Cys Gln Pro Val Pro Asp Ser Pro Leu Asp Lys Pro
            20                  25                  30

Glu Ile Val Ala Ala Met Ala Leu Ala Ala Glu Gln Ala Gly Ala Val
        35                  40                  45

Ala Ile Arg Ile Glu Gly Val Ala Asn Leu Gln Ala Thr Arg Ala Val
    50                  55                  60

Val Ser Val Pro Ile Ile Gly Ile Val Lys Arg Asp Leu Glu Asp Ser
65                  70                  75                  80

Pro Val Arg Ile Thr Ala Tyr Ile Glu Asp Val Asp Ala Leu Ala Gln
                85                  90                  95

Ala Gly Ala Asp Ile Ile Ala Ile Asp Gly Thr Asp Arg Pro Arg Pro
            100                 105                 110

Val Pro Val Glu Thr Leu Leu Ala Arg Ile His His Gly Leu Leu
        115                 120                 125

Ala Met Thr Asp Cys Ser Thr Pro Glu Asp Gly Leu Ala Cys Gln Lys
    130                 135                 140

Leu Gly Ala Glu Ile Ile Gly Thr Thr Leu Ser Gly Tyr Thr Thr Pro
145                 150                 155                 160

Glu Thr Pro Glu Glu Pro Asp Leu Ala Leu Val Lys Thr Leu Ser Asp
                165                 170                 175

Ala Gly Cys Arg Val Ile Ala Glu Gly Arg Tyr Asn Thr Pro Ala Gln
```

180                 185                 190
Ala Ala Asp Ala Met Arg His Gly Ala Trp Ala Val Thr Val Gly Ser
                195                 200                 205

Ala Ile Thr Arg Leu Glu His Ile Cys Gln Trp Tyr Asn Thr Ala Met
            210                 215                 220

Lys Lys Ala Val Leu
225

<210> SEQ ID NO 18
<211> LENGTH: 29
<212> TYPE: DNA
<213> ORGANISM: Artificial Sequence
<220> FEATURE:
<223> OTHER INFORMATION: Product of the human mind.

<400> SEQUENCE: 18
catgccatgg cttcgttact tgcacaact                                   29

<210> SEQ ID NO 19
<211> LENGTH: 34
<212> TYPE: DNA
<213> ORGANISM: Artificial Sequence
<220> FEATURE:
<223> OTHER INFORMATION: Product of the human mind.

<400> SEQUENCE: 19
cccaagctta tcatagcacc gccttttca tcgc                              34

<210> SEQ ID NO 20
<211> LENGTH: 22
<212> TYPE: DNA
<213> ORGANISM: Artificial Sequence
<220> FEATURE:
<223> OTHER INFORMATION: Product of the human mind.

<400> SEQUENCE: 20
ttcgtgtcgc tcaaggcgca ct                                          22

<210> SEQ ID NO 21
<211> LENGTH: 36
<212> TYPE: DNA
<213> ORGANISM: Artificial Sequence
<220> FEATURE:
<223> OTHER INFORMATION: Product of the human mind.

<400> SEQUENCE: 21
cactggccgt cgttttacgc ttctgcgttc tgattt                           36

<210> SEQ ID NO 22
<211> LENGTH: 36
<212> TYPE: DNA
<213> ORGANISM: Artificial Sequence
<220> FEATURE:
<223> OTHER INFORMATION: Product of the human mind.

<400> SEQUENCE: 22
aaatcagaac gcagaagcgt aaaacgacgg ccagtg                           36

<210> SEQ ID NO 23
<211> LENGTH: 19
<212> TYPE: DNA
<213> ORGANISM: Artificial Sequence
<220> FEATURE:
<223> OTHER INFORMATION: Product of the human mind.

-continued

<400> SEQUENCE: 23
ggaaacagct atgaccatg    19

<210> SEQ ID NO 24
<211> LENGTH: 72
<212> TYPE: DNA
<213> ORGANISM: Artificial Sequence
<220> FEATURE:
<223> OTHER INFORMATION: Product of the human mind.

<400> SEQUENCE: 24
cgcatcaggc ataaagcaga ttacttttg atttcataca gcggtgtttg ttcgtgtcgc    60
tcaaggcgca ct    72

<210> SEQ ID NO 25
<211> LENGTH: 68
<212> TYPE: DNA
<213> ORGANISM: Artificial Sequence
<220> FEATURE:
<223> OTHER INFORMATION: Product of the human mind.

<400> SEQUENCE: 25
agatgaatat tttaggtttt ttccagcgac tcggtagggc gttacagctg gaaacagcta    60
tgaccatg    68

<210> SEQ ID NO 26
<211> LENGTH: 690
<212> TYPE: DNA
<213> ORGANISM: Escherichia coli

<400> SEQUENCE: 26
atgtcgttac ttgcacaact ggatcaaaaa atcgctgcta acggtggcct gattgtctcc    60
tgccagccgg ttccggacag cccgctcgat aaacccgaaa tcgtcgccgc catggcatta    120
gcggcagaac aggcgggcgc ggttgccatt cgcattgaag gtgtggcaaa tctgcaagcc    180
acgcgtgcgg tggtgagtgt gccgattatt gaattgtga acgcgatct ggaggattct    240
ccggtacgca tcacggccta tattgaagat gttgatgcgc tggcgcaggc gggcgcggac    300
attatcgcca ttgacggcac cgaccgcccg cgtccggtgc ctgttgaaac gctgctggca    360
cgtattcacc atcacggttt actggcgatg accgaccgct caacgccgga agacggcctg    420
gcatgccaaa agctgggagc cgaaattatt ggcactacgc tttctggcta ccacgccct    480
gaaacgccag aagagccgga tctggcgctg gtgaaaacgt tgagcgacgc cggatgtcgg    540
gtgattgccg aagggcgtca acacgcct gctcaggcgg cggatgcgat cgccacggc    600
gcgtgggcgg tgacggtcgg ttctgcaatc acgcgtcttg agcacatttg tcagtggtac    660
aacacagcga tgaaaaaggc ggtgctatga    690

<210> SEQ ID NO 27
<211> LENGTH: 229
<212> TYPE: PRT
<213> ORGANISM: Escherichia coli

<400> SEQUENCE: 27

Met Ser Leu Leu Ala Gln Leu Asp Gln Lys Ile Ala Ala Asn Gly Gly
 1               5                  10                  15

Leu Ile Val Ser Cys Gln Pro Val Pro Asp Ser Pro Leu Asp Lys Pro
                20                  25                  30

Glu Ile Val Ala Ala Met Ala Leu Ala Ala Glu Gln Ala Gly Ala Val

```
              35                  40                  45
Ala Ile Arg Ile Glu Gly Val Ala Asn Leu Gln Ala Thr Arg Ala Val
 50                  55                  60
Val Ser Val Pro Ile Ile Gly Ile Val Lys Arg Asp Leu Glu Asp Ser
 65                  70                  75                  80
Pro Val Arg Ile Thr Ala Tyr Ile Glu Asp Val Asp Ala Leu Ala Gln
                 85                  90                  95
Ala Gly Ala Asp Ile Ile Ala Ile Asp Gly Thr Asp Arg Pro Arg Pro
            100                 105                 110
Val Pro Val Glu Thr Leu Leu Ala Arg Ile His His His Gly Leu Leu
        115                 120                 125
Ala Met Thr Asp Arg Ser Thr Pro Glu Asp Gly Leu Ala Cys Gln Lys
    130                 135                 140
Leu Gly Ala Glu Ile Ile Gly Thr Thr Leu Ser Gly Tyr Thr Thr Pro
145                 150                 155                 160
Glu Thr Pro Glu Glu Pro Asp Leu Ala Leu Val Lys Thr Leu Ser Asp
                165                 170                 175
Ala Gly Cys Arg Val Ile Ala Glu Gly Arg His Asn Thr Pro Ala Gln
            180                 185                 190
Ala Ala Asp Ala Met Arg His Gly Ala Trp Ala Val Thr Val Gly Ser
        195                 200                 205
Ala Ile Thr Arg Leu Glu His Ile Cys Gln Trp Tyr Asn Thr Ala Met
    210                 215                 220
Lys Lys Ala Val Leu
225

<210> SEQ ID NO 28
<211> LENGTH: 166
<212> TYPE: DNA
<213> ORGANISM: Artificial Sequence
<220> FEATURE:
<223> OTHER INFORMATION: Product of the human mind.

<400> SEQUENCE: 28
ttcgtgtcgc tcaaggcgca ctcccgttct ggataatgtt ttttgcgccg acatcataac    60
ggttctggca atattctga aatgagctgt tgacaattaa tcatccggct cgtataatgt   120
gtggaattgt gagcggataa caatttcaca caggaaacag accatg                 166

<210> SEQ ID NO 29
<211> LENGTH: 41
<212> TYPE: DNA
<213> ORGANISM: Artificial Sequence
<220> FEATURE:
<223> OTHER INFORMATION: Product of the human mind.

<400> SEQUENCE: 29
catggtcata gctgtttcct tcgtgtcgct caaggcgcac t                       41

<210> SEQ ID NO 30
<211> LENGTH: 19
<212> TYPE: DNA
<213> ORGANISM: Artificial Sequence
<220> FEATURE:
<223> OTHER INFORMATION: Product of the human mind.

<400> SEQUENCE: 30
catggtctgt ttcctgtgt                                                19
```

```
<210> SEQ ID NO 31
<211> LENGTH: 41
<212> TYPE: DNA
<213> ORGANISM: Artificial Sequence
<220> FEATURE:
<223> OTHER INFORMATION: Product of the human mind.

<400> SEQUENCE: 31
agtgcgcctt gagcgacacg aaggaaacag ctatgaccat g          41

<210> SEQ ID NO 32
<211> LENGTH: 18
<212> TYPE: DNA
<213> ORGANISM: Artificial Sequence
<220> FEATURE:
<223> OTHER INFORMATION: Product of the human mind.

<400> SEQUENCE: 32
gtaaaacgac ggccagtg                                    18

<210> SEQ ID NO 33
<211> LENGTH: 69
<212> TYPE: DNA
<213> ORGANISM: Artificial Sequence
<220> FEATURE:
<223> OTHER INFORMATION: Product of the human mind.

<400> SEQUENCE: 33
cttattcccc ctacgagaac cctatttggc tcgtttcaag ccgtattttt agtaaaacga    60
cggccagtg                                              69

<210> SEQ ID NO 34
<211> LENGTH: 67
<212> TYPE: DNA
<213> ORGANISM: Artificial Sequence
<220> FEATURE:
<223> OTHER INFORMATION: Product of the human mind.

<400> SEQUENCE: 34
agcagcccat tgccgacct gttcagcggt agtcaggggg atcagtctca tggtctgttt    60
cctgtgt                                                67

<210> SEQ ID NO 35
<211> LENGTH: 190
<212> TYPE: DNA
<213> ORGANISM: Escherichia coli

<400> SEQUENCE: 35
tgaggagata acataatctc cctcccacaa gcagtaacta taaaaataac cccactctct    60
acaaggctcg gggcgcccga aaaacgggc atacaggttg accgacaacg atataaatcg   120
gaatcaaaaa ctatgtgtgg aattgttggc gcgatcgcgc aacgtgatgt agcagaaatc   180
cttcttgaag                                            190

<210> SEQ ID NO 36
<211> LENGTH: 71
<212> TYPE: DNA
<213> ORGANISM: Artificial Sequence
<220> FEATURE:
<223> OTHER INFORMATION: Product of the human mind.

<400> SEQUENCE: 36
tgaggagata acataatctc cctcccacaa gcagtaacta taaaaataac cccgtaaaac    60
```
gacggccagt g 71

<210> SEQ ID NO 37
<211> LENGTH: 75
<212> TYPE: DNA
<213> ORGANISM: Artificial Sequence
<220> FEATURE:
<223> OTHER INFORMATION: Product of the human mind.

<400> SEQUENCE: 37
cttcaagaag gatttctgct acatcacgtt gcgcgatcgc gccaacaatt ccacacggaa 60
acagctatga ccatg 75

<210> SEQ ID NO 38
<211> LENGTH: 68
<212> TYPE: DNA
<213> ORGANISM: Artificial Sequence
<220> FEATURE:
<223> OTHER INFORMATION: Product of the human mind.

<400> SEQUENCE: 38
tgaggagata acataatctc cctcccacaa gcagtaacta taaaaataac gtaaaacgac 60
ggccagtg 68

<210> SEQ ID NO 39
<211> LENGTH: 74
<212> TYPE: DNA
<213> ORGANISM: Artificial Sequence
<220> FEATURE:
<223> OTHER INFORMATION: Product of the human mind.

<400> SEQUENCE: 39
cttcaagaag gatttctgct acatcacgtt gcgcgatcgc gccaacaatt ccacacatgg 60
tctgtttcct gtgt 74

<210> SEQ ID NO 40
<211> LENGTH: 69
<212> TYPE: DNA
<213> ORGANISM: Artificial Sequence
<220> FEATURE:
<223> OTHER INFORMATION: Product of the human mind.

<400> SEQUENCE: 40
cttattcccc ctacgagaac cctatttggc tcgtttcaag ccgtattttt agtaaaacga 60
cggccagtg 69

<210> SEQ ID NO 41
<211> LENGTH: 70
<212> TYPE: DNA
<213> ORGANISM: Artificial Sequence
<220> FEATURE:
<223> OTHER INFORMATION: Product of the human mind.

<400> SEQUENCE: 41
agcagcccat tgccgacct gttcagcggt agtcaggggg atcagtctca tggaaacagc 60
tatgaccatg 70

<210> SEQ ID NO 42
<211> LENGTH: 1131
<212> TYPE: DNA
<213> ORGANISM: Escherichia coli

<400> SEQUENCE: 42

```
gtgaaagtac tgactgtatt tggtacgcgc ccggaagcca tcaagatggc gccgttggtg      60
catgcgttgg caaaagatcc ttttttgag gctaaagttt gcgtcactgc gcagcatcgg      120
gagatgctcg atcaggtgct gaaactcttt tccattgtac ctgactacga tctcaacata     180
atgcagccag acagggcct gacagagata acctgtcgga ttctggaagg ctaaaaccct      240
attcttgccg agttcaaacc agacgtcgtg ctggttcacg gcgatacgac gacgacgctg    300
gcaaccagcc tggcggcgtt ttatcagcgt attcctgttg gtcacgttga ggctggtctg   360
cgcacgggcg atctctattc gccgtggccg gaagaggcta accgtacatt gaccgggcat   420
ctggcgatgt atcacttctc tccaaccgaa acttcccggc aaaacttgct gcgtgaaaac   480
gttgcggata gccgaatctt cattaccggt aatacagtca ttgatgcact gttatgggtg   540
cgtgaccagg tgatgagcag cgacaagctg cgttcagaac tggcggcaaa ttacccgttt   600
atcgaccccg ataaaaagat gattctggtg accggtcaca ggcgtgagag tttcggtcgt   660
ggctttgaag aaatctgcca cgcgctggca gacatcgcca ccacgcacca ggacatccag   720
attgtctatc cggtgcatct caacccgaac gtcagagaac cggtcaatcg cattctgggg   780
catgtgaaaa atgtcattct gatcgatccc caggagtatt taccgtttgt ctggctgatg   840
aaccacgcct ggctgatttt gaccgactca ggcggcattc aggaagaagc gccttcgctg   900
gggaaacctg tgctggtgat gcgcgatacc actgagcgtc cggaagcggt gacggcgggt   960
acggtgcgtc tggtaggcac ggataagcag cgaattgtcg aggaagtgac gcgtctttta  1020
aaagacgaaa acgaatatca agctatgagc cgcgcccata accccgtatgg tgatggtcag 1080
gcatgctctc gcattctgga agcgttaaaa aataatcgga tatcactatg a           1131
```

<210> SEQ ID NO 43
<211> LENGTH: 376
<212> TYPE: PRT
<213> ORGANISM: Escherichia coli

<400> SEQUENCE: 43

Met Lys Val Leu Thr Val Phe Gly Thr Arg Pro Glu Ala Ile Lys Met
1               5                   10                  15
Ala Pro Leu Val His Ala Leu Ala Lys Asp Pro Phe Phe Glu Ala Lys
                20                  25                  30
Val Cys Val Thr Ala Gln His Arg Glu Met Leu Asp Gln Val Leu Lys
            35                  40                  45
Leu Phe Ser Ile Val Pro Asp Tyr Asp Leu Asn Ile Met Gln Pro Gly
        50                  55                  60
Gln Gly Leu Thr Glu Ile Thr Cys Arg Ile Leu Glu Gly Leu Lys Pro
65                  70                  75                  80
Ile Leu Ala Glu Phe Lys Pro Asp Val Val Leu Val His Gly Asp Thr
                85                  90                  95
Thr Thr Thr Leu Ala Thr Ser Leu Ala Ala Phe Tyr Gln Arg Ile Pro
            100                 105                 110
Val Gly His Val Glu Ala Gly Leu Arg Thr Gly Asp Leu Tyr Ser Pro
        115                 120                 125
Trp Pro Glu Glu Ala Asn Arg Thr Leu Thr Gly His Leu Ala Met Tyr
    130                 135                 140
His Phe Ser Pro Thr Glu Thr Ser Arg Gln Asn Leu Leu Arg Glu Asn
145                 150                 155                 160
Val Ala Asp Ser Arg Ile Phe Ile Thr Gly Asn Thr Val Ile Asp Ala
                165                 170                 175

-continued

Leu Leu Trp Val Arg Asp Gln Val Met Ser Ser Asp Lys Leu Arg Ser
            180                 185                 190

Glu Leu Ala Ala Asn Tyr Pro Phe Ile Asp Pro Asp Lys Lys Met Ile
        195                 200                 205

Leu Val Thr Gly His Arg Arg Glu Ser Phe Gly Arg Gly Phe Glu Glu
    210                 215                 220

Ile Cys His Ala Leu Ala Asp Ile Ala Thr Thr His Gln Asp Ile Gln
225                 230                 235                 240

Ile Val Tyr Pro Val His Leu Asn Pro Asn Val Arg Glu Pro Val Asn
                245                 250                 255

Arg Ile Leu Gly His Val Lys Asn Val Ile Leu Ile Asp Pro Gln Glu
            260                 265                 270

Tyr Leu Pro Phe Val Trp Leu Met Asn His Ala Trp Leu Ile Leu Thr
        275                 280                 285

Asp Ser Gly Gly Ile Gln Glu Glu Ala Pro Ser Leu Gly Lys Pro Val
    290                 295                 300

Leu Val Met Arg Asp Thr Thr Glu Arg Pro Glu Ala Val Thr Ala Gly
305                 310                 315                 320

Thr Val Arg Leu Val Gly Thr Asp Lys Gln Arg Ile Val Glu Glu Val
                325                 330                 335

Thr Arg Leu Leu Lys Asp Glu Asn Glu Tyr Gln Ala Met Ser Arg Ala
            340                 345                 350

His Asn Pro Tyr Gly Asp Gly Gln Ala Cys Ser Arg Ile Leu Glu Ala
        355                 360                 365

Leu Lys Asn Asn Arg Ile Ser Leu
    370                 375

<210> SEQ ID NO 44
<211> LENGTH: 30
<212> TYPE: DNA
<213> ORGANISM: Artificial Sequence
<220> FEATURE:
<223> OTHER INFORMATION: Product of the human mind.

<400> SEQUENCE: 44
catgccatgg tgaaagtact gactgtattt                                    30

<210> SEQ ID NO 45
<211> LENGTH: 31
<212> TYPE: DNA
<213> ORGANISM: Artificial Sequence
<220> FEATURE:
<223> OTHER INFORMATION: Product of the human mind.

<400> SEQUENCE: 45
cccaagctta ttatagtgat atccgattat t                                  31

<210> SEQ ID NO 46
<211> LENGTH: 110
<212> TYPE: DNA
<213> ORGANISM: Escherichia coli

<400> SEQUENCE: 46
tgtcgggggg ctgatcgggg ctggtgtcgc attaacccgc cgttgctcga aatagcaaca   60
ctgctgcggt gagcgcaaag gcgctcgccg cttattcgaa gagaatcgat              110

<210> SEQ ID NO 47
<211> LENGTH: 73

```
<212> TYPE: DNA
<213> ORGANISM: Artificial Sequence
<220> FEATURE:
<223> OTHER INFORMATION: Product of the human mind.

<400> SEQUENCE: 47
tgtcgggggg ctgatcgggg ctggtgtcgc attaacccgc cgttgctcga aataggtaaa      60
acgacggcca gtg                                                        73

<210> SEQ ID NO 48
<211> LENGTH: 69
<212> TYPE: DNA
<213> ORGANISM: Artificial Sequence
<220> FEATURE:
<223> OTHER INFORMATION: Product of the human mind.

<400> SEQUENCE: 48
atcgattctc ttcgaataag cggcgagcgc ctttgcgctc accgcagcag catggtctgt      60
ttcctgtgt                                                             69

<210> SEQ ID NO 49
<211> LENGTH: 1131
<212> TYPE: DNA
<213> ORGANISM: Escherichia coli

<400> SEQUENCE: 49
gtgaaagtac tgactgtatt tggtacgcgc ccggaagcca tcaagatggc gccgttggtg      60
catgcgttgg caaaagatcc ttttttgag gctaaagttt ccgtcactgc gcagcatcgg     120
gagatgctcg atcaggtgct gaaactcttt tccattgtac ctgactacga tctcaacata     180
atgcagccag acagggcct acagagata acctgtcgga ttctggaagg ctaaaacct       240 attcttgccg agttcaaacc agacgtcgtg ctggttcacg cgatacgac gacgcgctg       300 gcaaccagcc tggcggcgtt tatcagcgt attcctgttg gtcacgttga ggctggtctg     360
cgcacgggcg atctctattc gccgtggccg gaagaggcta accgtacatt gaccgggcat     420
ctggcgatgt atgacttctc tccaaccgaa acttcccggc aaaacttgct gcgtgaaaac     480
gttgcggata gccgaatctt cattaccggt aatacagtca ttgatgcact gttatgggtg     540
cgtgaccagg tgatgagcag cgacaagctg cgttcagaac tggcggcaaa ttacccgttt     600
atcgaccccg ataaaaagat gattctggtg accggtcaca ggcgtgagag tttcggtcgt     660
ggctttgaag aaatcttcca gcgctggca gacatcgcca ccacgcacca ggacatccag     720
attgtctatc cggggcatct caacccgaac gtcagagaac cggtcaatcg cattctgggg     780
catgtgaaaa atgtcattct gatcgatccc caggagtatt taccgtttgt ctggctgatg     840
aaccacgcct ggctgatttt gaccgactca ggcggcattc aggaagaagc gccttcgctg     900
gggaaacctg tgctggtgat gcgcgatacc actgagcgtc cggaagcggt gacggcgggt     960
acggtgcgtc tggtaggcac ggataagcag cgaattgtcg aggaagtgac gcgtcttttta    1020 aaagacgaaa acgaatacca agctatgagc cgcgcccata acccgtatgg tgatggtcag    1080
gcatgctctc gcattctgga agcgttaaaa aataatcgga tatcactatg a             1131

<210> SEQ ID NO 50
<211> LENGTH: 376
<212> TYPE: PRT
<213> ORGANISM: Escherichia coli

<400> SEQUENCE: 50
```

```
Met Lys Val Leu Thr Val Phe Gly Thr Arg Pro Glu Ala Ile Lys Met
1               5                   10                  15

Ala Pro Leu Val His Ala Leu Ala Lys Asp Pro Phe Phe Glu Ala Lys
            20                  25                  30

Val Ser Val Thr Ala Gln His Arg Glu Met Leu Asp Gln Val Leu Lys
        35                  40                  45

Leu Phe Ser Ile Val Pro Asp Tyr Asp Leu Asn Ile Met Gln Pro Gly
    50                  55                  60

Gln Gly Leu Thr Glu Ile Thr Cys Arg Ile Leu Glu Gly Leu Lys Pro
65              70                  75                  80

Ile Leu Ala Glu Phe Lys Pro Asp Val Val Leu Val His Gly Asp Thr
                85                  90                  95

Thr Thr Thr Leu Ala Thr Ser Leu Ala Ala Phe Tyr Gln Arg Ile Pro
            100                 105                 110

Val Gly His Val Glu Ala Gly Leu Arg Thr Gly Asp Leu Tyr Ser Pro
            115                 120                 125

Trp Pro Glu Glu Ala Asn Arg Thr Leu Thr Gly His Leu Ala Met Tyr
    130                 135                 140

Asp Phe Ser Pro Thr Glu Thr Ser Arg Gln Asn Leu Leu Arg Glu Asn
145                 150                 155                 160

Val Ala Asp Ser Arg Ile Phe Ile Thr Gly Asn Thr Val Ile Asp Ala
                165                 170                 175

Leu Leu Trp Val Arg Asp Gln Val Met Ser Ser Asp Lys Leu Arg Ser
            180                 185                 190

Glu Leu Ala Ala Asn Tyr Pro Phe Ile Asp Pro Asp Lys Lys Met Ile
        195                 200                 205

Leu Val Thr Gly His Arg Arg Glu Ser Phe Gly Arg Gly Phe Glu Glu
    210                 215                 220

Ile Phe His Ala Leu Ala Asp Ile Ala Thr Thr His Gln Asp Ile Gln
225                 230                 235                 240

Ile Val Tyr Pro Gly His Leu Asn Pro Asn Val Arg Glu Pro Val Asn
            245                 250                 255

Arg Ile Leu Gly His Val Lys Asn Val Ile Leu Ile Asp Pro Gln Glu
            260                 265                 270

Tyr Leu Pro Phe Val Trp Leu Met Asn His Ala Trp Leu Ile Leu Thr
        275                 280                 285

Asp Ser Gly Gly Ile Gln Glu Glu Ala Pro Ser Leu Gly Lys Pro Val
    290                 295                 300

Leu Val Met Arg Asp Thr Thr Glu Arg Pro Glu Ala Val Thr Ala Gly
305                 310                 315                 320

Thr Val Arg Leu Val Gly Thr Asp Lys Gln Arg Ile Val Glu Glu Val
            325                 330                 335

Thr Arg Leu Leu Lys Asp Glu Asn Glu Tyr Gln Ala Met Ser Arg Ala
            340                 345                 350

His Asn Pro Tyr Gly Asp Gly Gln Ala Cys Ser Arg Ile Leu Glu Ala
        355                 360                 365

Leu Lys Asn Asn Arg Ile Ser Leu
    370                 375
```